(12) United States Patent
Crooke et al.

(10) Patent No.: US 7,449,178 B2
(45) Date of Patent: Nov. 11, 2008

(54) ATTENUATED GRAM NEGATIVE BACTERIA

(75) Inventors: Helen Rachel Crooke, Winnersh Triangle (GB); Jacqueline Elizabeth Shea, Winnersh Triangle (GB); Robert Graham Feldman, Winnersh Triangle (GB); Sylvain Gabriel Goutebroze, Lyons (FR); Francois-Xavier Le Gros, Saint Genis Laval (FR)

(73) Assignee: Merial Limited, Duluth, GA (US)

( * ) Notice: Subject to any disclaimer, the term of this patent is extended or adjusted under 35 U.S.C. 154(b) by 281 days.

(21) Appl. No.: 10/406,686

(22) Filed: Apr. 3, 2003

(65) Prior Publication Data

US 2004/0033586 A1 Feb. 19, 2004

Related U.S. Application Data

(60) Provisional application No. 60/370,282, filed on Apr. 5, 2002.

(51) Int. Cl.
| | |
|---|---|
| A61K 48/00 | (2006.01) |
| A61K 39/00 | (2006.01) |
| A61K 39/38 | (2006.01) |
| A61K 39/02 | (2006.01) |
| A61K 39/102 | (2006.01) |
| A01N 63/00 | (2006.01) |
| A01N 65/00 | (2006.01) |
| C12P 21/06 | (2006.01) |
| C12P 21/04 | (2006.01) |
| C12N 1/20 | (2006.01) |
| C12N 15/00 | (2006.01) |
| C07H 21/02 | (2006.01) |
| C07H 21/04 | (2006.01) |

(52) U.S. Cl. ............ 424/93.2; 424/93.1; 424/93.4; 424/255.1; 424/234.1; 424/200.1; 424/184.1; 424/256.1; 435/320.1; 435/252.3; 435/69.1; 435/71.1; 536/23.1; 536/23.7

(58) Field of Classification Search ........ 424/255.1, 424/234.1, 200.1; 536/23.7; 435/320.1, 435/252.3, 172.1

See application file for complete search history.

(56) References Cited

U.S. PATENT DOCUMENTS

| 6,326,001 | B1 * | 12/2001 | Inzana et al. | 424/93.4 |
|---|---|---|---|---|
| 6,783,764 | B1 * | 8/2004 | Segers et al. | 424/236.1 |
| 6,790,950 | B2 * | 9/2004 | Lowery et al. | 536/23.7 |
| 6,793,927 | B1 * | 9/2004 | Briggs et al. | 424/255.1 |
| 7,306,805 | B2 * | 12/2007 | Bakaletz et al. | 424/190.1 |
| 7,341,860 | B2 * | 3/2008 | Curtiss et al. | 435/252.3 |
| 2001/0018055 | A1 * | 8/2001 | Briggs et al. | 424/190.1 |
| 2004/0029129 | A1 * | 2/2004 | Wang et al. | 435/6 |
| 2004/0033586 | A1 * | 2/2004 | Crooke et al. | 435/252.3 |

FOREIGN PATENT DOCUMENTS

| EP | 0889120 | | 1/1999 |
|---|---|---|---|
| EP | 1350796 | A1 * | 10/2003 |
| WO | WO 94/11024 | A1 * | 5/1994 |
| WO | WO 97/49416 | A1 * | 12/1997 |
| WO | 00/61724 | | 10/2000 |
| WO | 03/086277 | | 10/2003 |

OTHER PUBLICATIONS

May et al. Proc.Natl. Acad. Sci. USA. 98(6): 3460-3465. 2001.*
Rudinger et al. 1976. Peptide Hormones. Natl. Instit. For Med. Res. pp. 1-7).*
Adler et al, J. Biotechnology, 1996, 44:139-144.*
Fuller et al, Microbial Pathogenesis, 2000, 29:39-51.*
Lu et al, Infection and Immunity, Dec. 1981, 34/3:1018-1024.*
Thumbikat et al, Microbial Pathogeneseis, 2003, 34:217-226.*
Adler et al, J. Biotechnology, 1999, 73:83-90.*
Chung et al, Vaccine, 2005, 23:2751-2755.*
Homchampa et al, Vaccine, 1997, 15:203-208.*
Fuller et al, Microbial Pathogenesis, 2000, 29:25-38.*
Hensel et al, Science, 1995, 269:400-403.*
May et al, PNAS, 2001, 98/6:3460-3465.*
Fleischmann et al, Science, 1995, 269:496-512.*
Winston et al, Gene, 1996, 179:199-204.*
Townsend et al. Genetic organization of *Pasteurella multocida cap* loci and development of a multiplex capsular PCR typing system. *Journal of Clinical Microbiology* 39(3): 924-929, 2001.
Lee et al. Tn10 insertional mutagenesis in *Pasteurella multocida*. *Veterinary Microbiology* 50(1-2): 143-148, 1996.
Hensel. Whole genome scan for habitat-specific genes by signature-tagged mutagenesis. *Electrophoresis* 19(4): 608-612, 1998.

* cited by examiner

*Primary Examiner*—N. M Minnifield
(74) *Attorney, Agent, or Firm*—Judy Javecki-Black; Merial Limited; Thomas Kowalski, Esq.

(57) ABSTRACT

Disclosed and claimed are a mutant of a gram negative bacterium, wherein said bacterium has at least one mutation in a nucleotide sequence which codes for a polypeptide having an identity which is equal or more than 70%, 75%, 80%, 85%, 90%, 95%, 96%, 97%, 98%, or 99% with an amino acid sequence coded by a nucleotide sequence selected from the group consisting of nucleotide sequences identified SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93; said mutation resulting in attenuated virulence of the bacterium. Immunogenic compositions and vaccines containing such a mutant are also disclosed and claimed.

26 Claims, No Drawings

ATTENUATED GRAM NEGATIVE BACTERIA

RELATED APPLICATIONS/INCORPORATION BY REFERENCE

This application claims priority from U.S. provisional application Ser. No. 60/370,282, filed on Apr. 5, 2002, incorporated herein by reference. The foregoing application, and all documents cited therein or during its prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This invention relates to live attenuated gram negative bacteria. Attenuated gram negative bacteria can be used in immunogenic compositions or in vaccine compositions, e.g., for the prevention of bacterial infections, as well as in research, as attenuated strains present a greater degree of safety to researchers and those (e.g., animals, humans) with whom they may come in contact.

The invention accordingly relates to immunogenic or vaccine compositions comprising gram negative bacteria of the invention; e.g., live attenuated gram negative bacteria. The bacteria also could be inactivated in the compositions; but it may be advantageous that the bacteria are live attenuated gram negative bacteria. The invention therefore further relates to methods for preparing and/or formulating such compositions; e.g., culturing or growing or propagating the bacteria on or in suitable medium, harvesting the bacteria, optionally inactivating the bacteria, and admixing with a suitable veterinarily or pharmaceutically acceptable carrier, excipient, diluent or vehicle and/or an adjuvant and/or stabilizer; or, admixing the bacteria with a suitable veterinarily or pharmaceutically acceptable carrier, excipient, diluent or vehicle and/or an adjuvant and/or stabilizer. Thus, the invention also relates to the use of the bacteria in formulating such compositions.

The attenuated bacteria also can act as an expression or replication vector, e.g., for replicating and/or expressing a nucleic acid molecule heterologous to the attenuated bacteria, e.g., a nucleic acid molecule encoding an immunogen, antigen or epitope from a pathogenic agent, such as a pathogenic agent that is other than the attenuated bacteria. The use of attenuated bacteria as a vector also provides a greater degree of safety to researchers or technicians working with the attenuated vectors and those (e.g., animals, humans) with whom they may come in contact.

The invention therefore further relates to methods for preparing such vectors, e.g., transforming the bacteria so that the bacteria contains and optionally expresses a heterologous nucleic acid molecule.

The invention also relates to uses of such vectors; e.g., a method for producing a gene product, e.g., polypeptide such as an immunogen, epitope or antigen, heterologous to the bacteria comprising culturing, growing or propagating bacteria transformed to contain and express a heterologous nucleic acid molecule encoding the gene product under conditions suitable for expression, and optionally harvesting or isolating or separating the gene product; or, harvesting or isolating or separating the gene product from bacteria transformed to express it; or, a method for eliciting an immunological response or immunogenic response against a gene product and/or the bacteria or a protective immune response as to a pathogen from which the gene product is derived or obtained and/or the bacteria comprising administering to a subject, e.g., animal, such as an animal susceptible to infection by the pathogen and/or the bacteria, for instance, a bovine or turkey, bacteria transformed to express the gene product; or a method for preparing an immunogenic, immunological or vaccine composition comprising admixing the vector or transformed bacteria with a pharmaceutically or veterinarily acceptable carrier, diluent, vehicle or excipient and/or adjuvant and/or stabilizer.

The invention also relates to targets for attenuation of bacteria, e.g., mutated nucleotide sequences or genes encoding the targets for attenuation of bacteria, and methods for targeting polypeptides for attenuation of bacteria and methods for generating attenuated bacteria. The targets for attenuation can be used as immunogenic compounds, e.g., in immunogenic compositions or in vaccine compositions, or for generating epitopes for use in immunogenic or vaccine compositions. Thus, the invention relates to the use of targets for attenuation in preparing in compositions, e.g., admixing with a pharmaceutically or veterinarily acceptable carrier, diluent, excipient or vehicle and/or an adjuvant and/or a stabilizer.

The invention further relates to methods for inducing an immunological or immunogenic or protective immune response in a subject, e.g., an animal, such as an animal susceptible to infection by a gram negative bacteria, such as a *Pasteurella*, e.g., a turkey or bovine, comprising administering to the animal a vaccine or immunogenic composition of the invention.

Even further still the invention relates to preparing such attenuated bacteria, e.g., gram negative bacteria, such as *Pasteurella*; for instance, comprising introducing one or more transposable elements into the bacteria and isolating bacteria containing the transposable element that do not cause mortality in a target species (and are hence attenuated). One can further optionally identify the mutations in the bacteria, to thereby allow for alternative means for producing the attenuated bacteria.

The invention even further relates to such alternative means for producing attenuated bacteria. Since the mutations are identified or characterized, the mutations can be introduced into bacteria through techniques other than introducing one or more transposable elements into the bacteria, such as by homologous recombination, e.g., homologous recombination whereby a portion of the bacterial genome results in at least an addition thereto (insertion) or a deletion therefrom (two or more additions and/or deletions are also envisioned) or a substitution (such as a replacement of at least one nucleotide by another one). Accordingly, the invention relates to a method for producing an attenuated bacteria containing a known or previously identified modification or mutation, e.g., a modification or mutation herein identified, comprising introducing a deletion or insertion or replacement into the bacterial genome, advantageously through recombination, and optionally identifying and/or isolating the bacteria containing the modification or mutation.

Thus, the invention further relates to a mutant of a gram negative bacterium, wherein said bacterium has at least one mutation in a nucleotide sequence which codes for a polypeptide having an identity which is equal or more than 70%, 75%, 80%, 85%, 90%, 95%, 96%, 97%, 98%, or 99% with an amino acid sequence coded by a nucleotide sequence selected from the group consisting of nucleotide sequences identified SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93; said mutation resulting in attenuated virulence of the bacterium. And, the invention relates to uses, compositions and methods involving such bacterium as herein described.

BACKGROUND

It is well established that live attenuated micro-organisms can be highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. In addition, unlike killed or inactivated preparations, live vaccines are able to induce potent cell-mediated responses which may be connected with their ability to replicate in antigen-presenting cells, such as macrophages.

There has been a long history of the use of live attenuated vaccines in animals and humans, notably using chemical mutagenesis techniques. However, empirically attenuated vaccines can revert to virulence.

Modem molecular biology techniques, coupled with the increasing knowledge of bacterial pathogenesis, has led to the identification of several genes that are involved in the growth and survival of the micro-organisms in vivo. This has provided new gene targets for attenuation, and to the concept that future vaccine strains could be 'rationally' attenuated by introducing defined non-reverting mutations into selected genes known to be involved in virulence, see for example WO-A-00/61724, WO-A-00/68261 and EP-A-0889120.

Although many attenuated strains have been produced in laboratories, only a few have qualified as potential vaccine candidates for use in animals. This may be due in part to the need to balance the immunogenicity of the vaccine with the possibility of the micro-organism to revert, becoming reactive and pathogenic.

It is clear that the selection of appropriate genes for attenuation, which will result in a suitable vaccine candidate, is not straightforward and cannot easily be predicted. Many factors may influence the acceptability of an attenuated mutant as a vaccine, and consequently research effort is required to identify and select suitable attenuating genes. Many attenuation experiments were conducted only in vitro and their results cannot be extrapolated in vivo, notably in relation to residual pathogenicity of the resulting mutants for the vaccinated animals.

Mention is made of:

Kachlany S C, Planet P J, Bhattacharjee M K, Kollia E, DeSalle R, Fine D H, Figurski D H., Nonspecific adherence by *Actinobacillus actinomycetemcomitans* requires genes widespread in bacteria and archaea. J Bacteriol. 2000 November; 182(21):6169-76.

Fuller T E, Martin S, Teel J F, Alaniz G R, Kennedy M J, Lowery D E., Identification of *Actinobacillus pleuropneumoniae* virulence genes using signature-tagged mutagenesis in a swine infection model. Microb Pathog. 2000 July; 29(1):39-51.

Fuller T E, Kennedy M J, Lowery D E., Identification of *Pasteurella multocida* virulence genes in a septicemic mouse model using signature-tagged mutagenesis. Microb Pathog. 2000 July; 29(1):25-38.

Kehrenberg C, Werckenthin C, Schwarz S., Tn5706, a transposon-like element from *Pasteurella multocida* mediating tetracycline resistance. Antimicrob Agents Chemother. 1998 August; 42(8):2116-8.

DeAngelis P L., Transposon Tn916 insertional mutagenesis of *Pasteurella multocida* and direct sequencing of disruption site. Microb Pathog. 1998a April; 24(4):203-9.

DeAngelis P L, Jing W, Drake R R, Achyuthan A M., Identification and molecular cloning of a unique hyaluronan synthase from *Pasteurella multocida*. J Biol Chem. 1998b April 3; 273(14):8454-8.

Lee M D, Henk A D., Tn10 insertional mutagenesis in *Pasteurella multocida*. Vet Microbiol. 1996 May; 50(1-2):143-8.

Choi K H, Maheswaran S K, Choi C S., Colorimetric assay using XTT for assessing virulence of avian *Pasteurella multocida* strains. Vet Microbiol. 1995 July; 45(2-3): 191-200.

Nnalue NA. Tn7 inserts in both orientations at a single chromosomal location and apparently forms cointegrates in *Pasteurella multocida*. Mol Microbiol. 1990 January; 4(1):107-17.

Stocker U.S. Pat. Nos. 4,550,081, 4,837,151, 5,210,035 and 5,643,771.

Highlander U.S. Pat. No. 6,180,112.

Kachlany involved Tad genes. There is no relation between the Tad genes mutated in Kachlany and attenuation. There is no testing on animals in Kachlany and the Tad genes are not selected in the present invention. The Fuller papers involve sequences that are not selected in the present invention. Kehrenberg did not involve an attenuated mutant, or a Signature Tagged Mutagenesis or STM technique; but rather, Kehrenberg involved a directed insertion of a transposon (use of identical insertion element). DeAngelis 1998a provides only a general description of a STM technique, and nothing about mutants, per se. DeAngelis 1998b involved the use of a STM technique to insert a transposon in the HA biosynthesis locus (Genbank AF036004). This sequence is a homologue to the sequence Pm0775 of PM70. The sequence encoding Pm0775 is not selected in the present invention. Lee concerns the use of a STM technique with a Tn10 transposon; Lee fails to disclose or suggest any tests on animals or any searches for attenuated mutants; but rather, Lee involved only auxotrophic mutants. While Choi cites a *Pasteurella multocida* transposon insertion mutant, and there may have been no mortality induced by this mutant, Choi contains no details about the location of the transposon insertion and therefore cannot be said to be reproducible. Nnalue similarly fails to teach or suggest the instant invention. The Stocker patents involved the insertion of a Tn10 transposon in the aroA gene. AroA gene is not selected in the present invention. Highlander concerns the insertion of a Tn1545 transposon in the lktC gene to inactive leukotoxin. LktC gene is not selected in the instant invention. Accordingly, it is verily believed that the instant invention is not taught or suggested in the art.

Moreover, it is desirable to characterize genes or nucleic acid sequences involved in attenuation and on this basis develop attenuated bacteria, as well as attenuated vaccines or immunogenic compositions, such as those having a high degree of immunogenicity and which exhibit a good safety profile with limited or no side effects.

SUMMARY OF THE INVENTION

The invention provides a mutant of a gram negative bacterium having a mutation in a first nucleotide sequence that codes for a first polypeptide and results in the bacterium having attenuated virulence, wherein:

the first polypeptide has an amino acid sequence;

a second polypeptide has an amino acid sequence encoded by a nucleotide sequence identified as SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, or 93; and the amino acid sequence of the first polypeptide is the same as that of the second polypeptide, or the amino acid sequence of the first polypeptide has an identity which is equal to or more than 70%, 75%, 80%, 85%, 90%, 95%, 96%, 97%, 98%, or 99% with the amino acid sequence of the second polypeptide.

The mutant bacterium can be a Pasteurellaceae, e.g. the bacterium can be: *Pasteurella multocida, Pasteurella haemolytica, Pasteurella anatipestifer* or *Actinobacillus pleuropneumoniae*; advantageously *Pasteurella multocida*.

The mutation can be a deletion in the first nucleotide sequence, or an insertion into it or replacement of nucleic acids, such as a deletion of the whole first nucleotide sequence; or an insertion between: nucleotides 180-181 or nucleotides 182-183 or nucleotides 190-191 in SEQ ID NO: 2, nucleotides 77-78 or nucleotides 1026-1027 or nucleotides 1027-1028 in SEQ ID NO: 6, nucleotides 416-417 in SEQ ID NO: 9, nucleotides 389-390 in SEQ ID NO: 12, nucleotides 381-382 in SEQ ID NO: 16, nucleotides 219-220 in SEQ ID NO: 19, nucleotides 1353-1354 in SEQ ID NO: 22, nucleotides 136-137 in SEQ ID NO: 25, nucleotides 384-385 in SEQ ID NO: 28, nucleotides 222-223 or nucleotides 225-226 in SEQ ID NO: 31, nucleotides 217-218 in SEQ ID NO: 34, nucleotides 1411-1412 in SEQ ID NO: 37, nucleotides 943-944 in SEQ ID NO: 40, nucleotides 855-856 in SEQ ID NO: 43, nucleotides 369-370 in SEQ ID NO: 46, nucleotides 111-112 in SEQ ID NO: 49, nucleotides 443-444 in SEQ ID NO: 52, nucleotides 4-5 in SEQ ID NO: 55, nucleotides 573-574 in SEQ ID NO: 61, nucleotides 875-876 in SEQ ID NO: 64, nucleotides 218-219 in SEQ ID NO: 70, nucleotides 1072-1087 in SEQ ID NO: 75, nucleotides 64-65 in SEQ ID NO: 78, nucleotides 282-283 in SEQ ID NO: 81, nucleotides 1431-1432 in SEQ ID NO: 84, nucleotides 974-975 in SEQ ID NO: 87, nucleotides 802-803 in SEQ ID NO: 90, nucleotides 850-851 in SEQ ID NO: 92;or immediately upstream nucleotide 1 in SEQ ID NO: 58; or immediately upstream nucleotide 1 in SEQ ID NO: 67.

The mutant can comprises an heterologous nucleic acid sequence, such as an heterologous nucleic acid sequence that codes for an immunogen from a pathogenic viral, parasitic or bacterial agent, a therapeutic protein, an allergen, a growth factor or a cytokine.

The invention also provides an immunogenic composition or vaccine comprising a mutant according to the invention, and a pharmaceutically or veterinarily acceptable diluent, carrier, vehicle or excipient, and optionally further comprising an adjuvant.

The invention further provides an isolated first polypeptide having an amino acid sequence, wherein there is:

a second polypeptide having an amino acid sequence encoded by a nucleotide sequence identified as SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, or 93; and the amino acid sequence of the first polypeptide is the same as that of the second polypeptide, or the amino acid sequence of the first polypeptide has an identity which is equal to or more than 70%, 75%, 80%, 85%, 90%, 95%, 96%, 97%, 98%, or 99% with the amino acid sequence of the second polypeptide.

The invention envisions an immunogenic or vaccine composition containing the isolated first polypeptide, and a pharmaceutically or veterinarily acceptable diluent, carrier, vehicle or excipient, and optionally an adjuvant.

Further still, the invention envisions an antibody preparation comprising an antibody specific to the first isolated polypeptide.

The invention also involves a diagnostic method for detecting infection by a gram negative bacterium, comprising detecting in a sample the first isolated polypeptide or an antibody specific to that first isolated polypeptide.

The invention further concerns a passive immunization method comprising administering the antibody preparation.

The invention also provides an isolated nucleic acid molecule having a sequence identified as SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, or 93, or identified as SEQ ID NO: 1, 4, 5, 8, 11, 14, 15, 18, 21, 24, 27, 30, 33, 36, 39, 42, 45, 48, 51, 54, 57, 60, 63, 66, 69, 72, 73, 77, 80, 83, 86, 89, 92, 95, 96, or 97, as well as a PCR primer for detecting gram negative bacteria comprising an isolated nucleic acid molecule having a sequence that is at least 10 contiguous nucleic acids of a nucleotide sequence identified as SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, or 93, or identified as SEQ ID NO: 1, 4, 5, 8, 11, 14, 15, 18, 21, 24, 27, 30, 33, 36, 39, 42, 45, 48, 51, 54, 57, 60, 63, 66, 69, 72, 73, 77, 80, 83, 86, 89, 92, 95, 96, or 97. A probe or primer can be any stretch of at least 8, preferably at least 10, more preferably at least 12, 13, 14, or 15, such as at least 20, e.g., at least 23 or 25, for instance at least 27 or 30 nucleotides which are unique to the sequence desired to be amplified or which are in the sequence desired to be amplified and are least conserved, e.g., conserved among the gram negative bacteria or among a particular family or species of gram negative bacteria, such as among *Pasteurella*, or among any one of *Pasteurella multocida, Pasteurella haemolytica, Pasteurella anatipestifer* or *Actinobacillus pleuropneumoniae*; advantageously *Pasteurella multocida*. As to PCR or hybridization primers or probes and optimal lengths therefor, reference is also made to Kajimura et al., GATA 7(4):71-79 (1990).

The terms "immunogenic composition" and "immunological composition" and "immunogenic or immunological composition" cover any composition that elicits an immune response against the targeted pathogen; for instance, after administration or injection into the animal (such as an avian, e.g., turkey or bovine, e.g. cow), elicits an immune response against the targeted pathogen (e.g., *Pasteurella multocida*). The terms "vaccinal composition" and "vaccine" and "vaccine composition" covers any composition that induces a protective immune response against the targeted pathogen or which efficaciously protects against the pathogen; for instance, after administration or injection into the animal (e.g., avian such as turkey or bovine such as cow), elicits a protective immune response against the targeted pathogen or provides efficacious protection against the pathogen (e.g., *P. multocida*). A subunit of a pathogen, e.g. an antigen or immunogen or epitope isolated from the pathogen, e.g., bacteria such as a gram negative bacteria, for instance, *P. multocida*; and, a subunit composition comprises or consists essentially of one or more antigens, immunogens or epitopes isolated from the pathogen, e.g., bacteria, such as a gram negative bacteria, for instance *P. multocida*.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

The present invention provides nucleotide sequences and genes involved in the attenuation of a micro-organism, such as bacteria, for instance, gram negative bacteria, e.g., *Pasteurella multocida*, products (e.g., proteins, antigens, immunogens, epitopes) encoded by the nucleotide sequences, methods for producing such nucleotide sequences, products, micro-organisms, and uses therefor, such as for preparing vaccine or immunogenic compositions or for eliciting an immunological or immune response or as a vector, e.g., as an expression vector (for instance, an in vitro or in vivo expression vector).

Mutations introduced into nucleotide sequences and genes of micro-organisms produce novel and nonobvious attenuated mutants. These mutants are useful for the production of live attenuated immunogenic compositions or live attenuated vaccines having a high degree of immunogenicity.

These mutants are also useful as vectors which can be useful for expression in vitro of expression products, as well as for reproduction or replication of nucleotide sequences (e.g., replication of DNA), and for in vivo expression products.

Identification of the mutations provides novel and nonobvious nucleotide sequences and genes, as well as novel and nonobvious gene products encoded by the nucleotide sequences and genes.

Such gene products provide antigens, immunogens and epitopes, and are useful as isolated gene products.

Such isolated gene products, as well as epitopes thereof, are also useful for generating antibodies, which are useful in diagnostic applications.

Such gene products, which can provide or generate epitopes, antigens or immunogens, are also useful for immunogenic or immunological compositions, as well as vaccines.

In an aspect, the invention provides bacteria containing an attenuating mutation in a nucleotide sequence or a gene wherein the mutation modifies, reduces or abolishes the expression and/or the biological activity of a polypeptide or protein encoded by a gene, resulting in attenuated virulence of the bacterium.

The mutation is not necessarily located within a coding sequence or gene to disrupt its function, leading to attenuation. The mutation can also be made in nucleotide sequences involved in the regulation of the expression of the gene, for instance, in regions that regulate transcription initiation, translation and transcription termination. Thus also included are promoters and ribosome binding regions (in general these regulatory elements lie approximately between 60 and 250 nucleotides upstream of the start codon of the coding sequence or gene; Doree S M et al., J. Bacteriol. 2001, 183(6): 1983-9; Pandher K et al., Infect. Imm. 1998, 66(12): 5613-9; Chung J Y et al., FEMS Microbiol letters 1998, 166: 289-296), transcription terminators (in general the terminator is located within approximately 50 nucleotides downstream of the stop codon of the coding sequence or gene; Ward C K et al., Infect. Imm. 1998, 66(7): 3326-36). In the case of an operon, such regulatory regions may be located in a greater distance upstream of the gene or coding sequence. A mutation in an intergenic region can also lead to attenuation.

A mutation within such regulatory sequences associated with the coding sequence or gene so that the mutation of this nucleotide sequence modifies, inhibits or abolishes the expression and/or the biological activity of the polypeptide or the protein encoded by the gene, resulting in attenuated virulence of the bacterium would be an equivalent to a mutation within a gene or coding sequence identified in the present invention Attenuation reduces or abolishes the pathogenicity of the bacteria and the gravity of the clinical signs or lesions, decreases the growth rate of the bacteria, and prevents the death from the bacteria.

The invention concerns micro-organisms, such as bacteria, e.g., gram negative bacteria, such as bacteria of the Pasteurellaceae family, for instance, *Pasteurella multocida, Pasteurella haemolytica, Pasteurella anatipestifer* and *Actinobacillus pleuropneumoniae*. Advantageously the bacteria are *Pasteurella multocida*.

*Pasteurella multocida* is a gram negative bacterium, which is the causative agent of various diseases of production animals and an opportunistic human pathogen. It is the aetiologic agent of severe pasteurellosis, such as fowl cholera in domestic and wild birds, bovine haemorrhagic septicaemia and porcine atrophic rhinitis (Hunt M L et al., Vet Microbiol 2000, 72(1-2): 3-25). Isolates may be grouped serologically based on the capsular antigens into serogroups (A, B, D, E and F) or into 16 serotypes based on somatic LPS antigens.

Potential nucleotide sequences involved in attenuation of bacteria have been identified using Signature Tagged Mutagenesis (STM). This method is discussed in documents cited herein and mention is also made of WO-A-96/17951.

STM involves the insertion of a unique, signature-tagged, transposon into the genome of a micro-organism.

At the locus of insertion, the genome nucleotide sequence is disrupted. In the instant invention, the resulting mutation (and hence mutant carrying the mutation) is analyzed for attenuation.

The sequence of the disrupted region (e.g. gene or coding sequence or open reading frame (ORF)) for each attenuated mutant is determined by PCR-amplification (polymerase chain reaction), cloning and sequencing of the DNA regions flanking the transposon.

In an embodiment of the instant invention, the STM method described in WO-A-96/17951 was adapted to be functional in *Pasteurella multocida*. These adaptations notably include the use of the Tn10 transposon rather than Tn5, and the use for selection of a CDM medium without leucine rather than a streptomycin resistance selection. More details are given in the examples.

A further selection of genes or nucleotide sequences involved in attenuation from the potential genes identified by the STM method is based on absence of mortality after inoculation of the mutant bacteria to animals.

For veterinary applications, one advantageous aspect of the invention comprises the implementation of an experimental selection directly in the target animal, rather than in an animal model. This method allows a more accurate selection for appropriate mutations of the mutant bacteria. For *Pasteurella multocida*, experiments are done directly in turkeys, one of the natural target hosts of *Pasteurella multocida*.

Turkeys are inoculated intramuscularly with a sufficient amount of pools of signature-tagged *P. multocida* mutants (e.g. 0.5 ml, $10^7$ CFU per animal). The mutants that are not re-isolated at a certain time after inoculation are considered as potentially attenuated. The mutants which are not re-isolated are distinguished from those in the pool that are re-isolated by PCR amplification and analysis of the signature tags.

Each potentially attenuated mutant is then injected by the intramuscular route into turkeys (e.g. 0.5 ml, $10^4$ CFU per animal). The mortality of the turkeys is recorded daily for 7 days after the inoculation. The mutants not leading to death are considered as attenuated.

The specific method has been carried out on *Pasteurella multocida* strain P-1059 and a number of attenuated mutants have been obtained. Five of them have been deposited on the Apr. 1, 2003 in the CNCM (Collection Nationale de Cultures de Microorganismes) of the Pasteur Institute, Paris, France. The 4G11 mutant is available under the accession number CNCM I-2999. The 5D5 mutant is available under the accession number CNCM I-3000. The 9C8 mutant is available under the accession number CNCM I-3001. The 9H4 mutant is available under the accession number CNCM I-3002. The 13E1 mutant is available under the accession number CNCM I-3003.

The nucleotide sequences flanking the locus of the transposon insertion are designated SEQ ID NO: 1, 4, 5, 8, 11, 14, 15, 18, 21, 24, 27, 30, 33, 36, 39, 42, 45, 48, 51, 54, 57, 60, 63, 66, 69, 72, 73, 77, 80, 83, 86, 89, 92, 95, 96, 97.

The transposons were inserted in *Pasteurella multocida* strain P-1059 immediately at the 5' end of the sequences 1, 8, 11, 14, 15, 27, 33, 42, 54, 57, 66, 72, 73, 77, 80, 95 and 97, and immediately at the 3' end of the sequences 4, 5, 18, 21, 24, 30, 36, 39, 45, 48, 51, 60, 63, 69, 83, 86, 89 and 96. For the mutant 9H4, the transposon was inserted between the nucleotides at positions 850-851 of the sequence SEQ ID NO: 92.

A particular aspect of the invention is attenuated mutants of *Pasteurella multocida* strain P-1059 having an attenuating mutation in the gene or ORF and/or their regulatory regions comprising a sequence selected from the sequences SEQ ID NO: 1, 4, 5, 8, 11, 14, 15, 18, 21, 24, 27, 30, 33, 36, 39, 42, 45, 48, 51, 54, 57, 60, 63, 66, 69, 72, 73, 77, 80, 83, 86, 89, 92, 95, 96, and 97.

Further particular embodiments of the invention include attenuated mutants according to the invention such as the attenuated mutants herein-mentioned as deposited in the CNCM under the terms of the Budapest Treaty.

Attenuated P-1059 mutants may be obtained, for example, by transposon insertion or by directed mutagenesis (deletion, insertion, replacement). The attenuating mutation can be made within these nucleotide sequences or genes as well as in the complementary sequences thereof. The attenuating mutation can also be made in nucleotide sequences involved in the regulatory region of the said genes or nucleotide sequences.

The above sequences or parts thereof (such as at least 10, 15 or 20 nucleotides thereof, for instance, at least 10 contiguous nucleotides thereof, or at least 15 contiguous nucleotides thereof and more advantageously at least 20 contiguous nucleotides thereof, up to the full length of the sequences) may be used as PCR primers to detect and select the transposon insertion mutants. PCR can involve a pair of primers, for instance, one specific to the transposon, and the other specific to the gene or nucleotide sequence to be mutated. Based on the expected size of PCR amplified products, the method allows for amplification and/or detection of the PCR fragments The knowledge of the corresponding gene or ORF and/or their regulatory regions in the organism, e.g., gram negative bacteria, such as *Pasteurella*, e.g., *Pasteurella multocida*, for instance *Pasteurella multocida* strain PM70 or P-1059 (see, e.g., infra); for example the size of the corresponding gene or ORF and/or their regulatory regions may be used to design PCR primers, to screen the amplified PCR fragments and to detect those having a right size allowing the selection of the mutants.

The whole genome of *Pasteurella multocida* strain PM70 is available in the EMBL database and in May B J et al., Proc. Natl. Acad. Sci. USA, 2001, 98(6): 3460-5. Blasts done with the sequences SEQ ID NO: 1, 4, 5, 8, 11, 14, 15, 18, 21, 24, 27, 30, 33, 36, 39, 42, 45, 48, 51, 54, 57, 60, 63, 66, 69, 72, 73, 77, 80, 83, 86, 89, 92, 95, 96, 97 allowed to localise the homologous sequences on PM70 genome and then to determine the corresponding genes or ORFs in PM70.

These nucleotide sequence in *Pasteurella multocida* strain PM70 are designated SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90.

For the mutant 9H4 of the P-1059 strain, no homologous sequence was found in PM70. The P-1059 ORF has been sequenced and designated SEQ ID NO: 93.

Another aspect of the invention is attenuated mutants of strain PM70 having at least one attenuating mutation in a gene or ORF comprising a nucleotide sequence selected from SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87 and 90 and/or their regulatory regions.

The attenuating mutation can be made within these nucleotide sequences or genes as well as in the complementary sequences thereof. The attenuating mutation can also be made in nucleotide sequences involved in the regulatory region of the said genes. Attenuated mutants may be obtained, for example, by transposon insertion or by directed mutagenesis (deletion, insertion, replacement).

The term of "complementary" means herein the nucleotide sequence of the other strand in the double-stranded genome, so covers the anti-sense strand as complement of the sense strand, and conversely. The term "nucleotide" also encompasses deoxyribonucleotide (so constituted with deoxyribonucleic acids or DNA), ribonucleotide (so constituted with ribonucleic acids or RNA) and messenger ribonucleotide (mRNA).

More generally attenuating mutations can be introduced into the genome of a bacterium such as a gram negative bacterium, for instance a bacteria of the Pasteurellacaea family, e.g. *P. multocida, P. haemolytica, P. anatipestifer, A. pleuropneumoniae*, advantageously a bacteria in the genome of any one of the various strains of *P. multocida* (e.g. P-1059 strain, PM70 strain), mutations in at least one nucleotide sequence which codes for an amino acid sequence that has at least about 70% identity, at least about 75% identity, at least about 80% identity, at least about 85%, at least about 90% identity, and advantageously at least about 95, 96, 97, 98, or 99% or more identity to one of the amino acid sequences coded by a nucleotide sequence identified as SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93. The attenuating mutation can be made within these nucleotide sequences or genes as well as in the complementary sequences thereof. The attenuating mutation can also be made in nucleotide sequences involved in the regulatory region of the said genes. Attenuated mutants may be obtained for example by transposon insertion or by directed mutagenesis (deletion, insertion, replacement). The attenuated mutants obtained are embodiments of the invention. Particular embodiments are the P-1059 attenuated mutants.

The percentage of identity between two amino acid sequences can be established by the NCBI (National Center for Biotechnology Information) pairwise blast and the blosum62 matrix, using the standard parameters (That is, note the BLAST or BLASTX algorithm available on the "National Center for Biotechnology Information" (NCBI, Bethesda, Md., USA) server, as well as in Altschul et al. J. Mol. Biol. 1990. 215. 403-410; and thus, this document speaks of using the algorithm or the BLAST or BLASTX and BLOSUM62 matrix by the term "blasts").

The verb "code" used herein does not mean that the nucleotide sequence is limited to an actual coding sequence but also encompasses the whole gene including its regulatory sequences which are non-coding sequences.

Sequence homology or identity such as nucleotide sequence homology also can be determined using the "Align" program of Myers and Miller, ("Optimal Alignments in Linear Space", CABIOS 4, 11-17, 1988, incorporated herein by reference) and available at NCBI, as well as the same or other programs available via the Internet at sites thereon such as the NCBI site.

Alternatively or additionally, the term "homology" or "identity", for instance, with respect to a nucleotide or amino acid sequence, can indicate a quantitative measure of homology between two sequences. The percent sequence homology can be calculated as $(N_{ref} - N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

Advantageously, sequence identity or homology such as amino acid sequence identity or homology can be determined using the BlastP program (Altschul et al., Nucl. Acids Res. 25, 3389-3402, incorporated herein by reference) and available at NCBI, as well as the same or other programs available via the Internet at sites thereon such as the NCBI site.

The following documents (each incorporated herein by reference) provide algorithms for comparing the relative identity or homology of sequences such as amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," J. Mol. Biol. 48:444-453 (1970); Smith T F and Waterman M S, "Comparison of Bio-sequences," Advances in Applied Mathematics 2:482-489 (1981); Smith T F, Waterman M S and Sadler J R, "Statistical characterization of nucleic acid sequence functional domains," Nucleic Acids Res., 11:2205-2220 (1983); Feng D F and Dolittle R F, "Progressive sequence alignment as a prerequisite to correct phylogenetic trees," J. of Molec. Evol., 25:351-360 (1987); Higgins D G and Sharp P M, "Fast and sensitive multiple sequence alignment on a microcomputer," CABIOS, 5: 151-153 (1989); Thompson J D, Higgins D G and Gibson T J, "ClusterW: improving the sensitivity of progressive multiple sequence alignment through sequence weighing, positions-specific gap penalties and weight matrix choice," Nucleic Acid Res., 22:4673-480 (1994); and, Devereux J, Haeberlie P and Smithies O, "A comprehensive set of sequence analysis program for the VAX," Nucl. Acids Res., 12: 387-395 (1984). And, without undue experimentation, the skilled artisan can consult with many other programs or references for determining percent homology.

The invention concerns the mutation of the nucleotide sequences or genes encoding polypeptides or proteins having the same biological function. The similarity of function may be analyzed or identified or determined or reviewed by the conservation of active sites. This can be done by a NCBI DART research (Domain Architecture Retrieval Tool).

The present invention thus provides attenuated mutants of a bacterium as described herein, comprising an attenuating mutation as defined herein.

The attenuated gram negative bacteria mutants include one mutation, wherein all or part of at least one specific gene or nucleic acid sequence is mutated as discussed herein. The specific gene or nucleic acid sequence includes those comprising, or homologous to (e.g., 70%, 75%, 80%, 85%, 90%, 95%, 96%, 97%, 98%, or 99% homologous to), sequence SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90 or 93, or their-regulatory regions. Advantageously, the specific gene or nucleic acid sequence includes those comprising, or homologous to, the sequence SEQ ID NO: 2, 6, 9, 12, 25, 31, 37, 40, 43, 46, 70, 75, 78, 81, 84, 87, 90 or 93, or their regulatory regions. More advantageously, the specific gene or nucleic acid sequence includes those comprising, or homologous to, the sequence SEQ ID NO: 6, 12, 25, 31, 37, 40, 46, 70, 75, 84, 87, 90 or 93, or their regulatory regions. And even more advantageously, the specific gene or nucleic acid sequence includes those comprising, or homologous to, sequence SEQ ID NO: 37, 40, 75, 90 or 93, or their homologous nucleotide sequences. Preferably the mutant is a *Pasteurella*, such as a *P. multocida*, for example P-1059 or PM70.

The mutations may be introduced into the micro-organism using any known technique, such as, for example, recombinant DNA-technology, in order to introduce a well-defined mutation in the selected gene or nucleic acid sequence (directed mutagenesis). Such a mutation may be an insertion of homologous or heterologous nucleic acid sequence, a deletion, a replacement, e.g., a replacement of at least one nucleotide by another or a combination thereof. In an embodiment, the mutation is a deletion mutation, where disruption of the gene or nucleic acid sequence is caused by the deletion of part, and advantageously by the deletion of the entire nucleic acid sequence or gene. Deletion of nucleic acids avoids reversion to pathogenicity. In another embodiment the mutation is an insertion into a locus that corresponds to the transposon insertion loci described herein, e.g., in the examples. These loci, with reference to the P-1059 strain, are advantageously located immediately at the 5' end of the sequences 1, 8, 11, 14, 15, 27, 33, 42, 54, 57, 66, 72, 73, 77, 80, 95 and 97, and immediately at the 3' end of the sequences 4, 5, 18, 21, 24, 30, 36, 39, 45, 48, 51, 60, 63, 69, 83, 86, 89 and 96. These loci are also those located in the PM70 strain between: nucleotides 180-181 or 182-183 or 190-191 in SEQ ID NO: 2, 77-78 or 1026-1027 or 1027-1028 in SEQ ID NO: 6, 416-417 in SEQ ID NO: 9, 389-390 in SEQ ID NO: 12, 381-382 in SEQ ID NO: 16, 219-220 in SEQ ID NO: 19, 1353-1354 in SEQ ID NO: 22, 136-137 in SEQ ID NO: 25, 384-385 in SEQ ID NO: 28, 222-223 or 225-226 in SEQ ID NO: 31, 217-218 in SEQ ID NO: 34, 1411-1412 in SEQ ID NO: 37, 943-944 in SEQ ID NO: 40, 855-856 in SEQ ID NO: 43, 369-370 in SEQ ID NO: 46, 111-112 in SEQ ID NO: 49, 443-444 in SEQ ID NO: 52, 4-5 in SEQ ID NO: 55, 573-574 in SEQ ID NO: 61, 875-876 in SEQ ID NO: 64, 218-219 in SEQ ID NO: 70, 1072-1087 in SEQ ID NO: 75, 64-65 in SEQ ID NO: 78, 282-283 in SEQ ID NO: 81, 1431-1432 in SEQ ID NO: 84, 974-975 in SEQ ID NO: 87, 802-803 in SEQ ID NO: 90, 850-851 in SEQ ID NO: 92; or, immediately upstream nucleotide 1 in SEQ ID NO: 58; or immediately upstream nucleotide 1 in SEQ ID NO: 67. These loci are also those located between similar pairs of nucleotides (than recited for PM70) in nucleotide sequences of another gram negative bacterium, such as a Pasteurellacaea family member, e.g. *P. multocida, P. haemolytica, P. anatipestifer, A. pleuropneumoniae*, encoding an homologous amino acid sequence as defined herein with its percentage of identity. Thus, mutants can be gram negative bacteria and are advantageously a *Pasteurella*, such as a *P. multocida, P. haemolytica, P. anatipestifer, A. pleuropneumoniae*, for example a *P. multocida*, such as P-1059 or PM70.

By definition, deletion mutants comprise at least one deletion of or in a nucleotide sequence according to the invention. These deletion mutants include those wherein all or part of a specific gene sequence or specific nucleotide sequence is deleted. In one aspect, the mutation results in deletion of at least one nucleic acid, of at least about 10%, at least about 20%, at least about 30%, at least about 40%, at least about 50%, at least about 60%, at least about 70%, at least about 80%, at least about 90%, at least about 95%, at least about 98%, or at least about 99% of the gene or specific nucleotide sequence. Preferably the entire gene or specific nucleotide sequence is deleted.

The mutants can comprise more than one mutation, which may result in additive or synergistic degrees of attenuation, and may result in a better prevention of the reversion of attenuation.

These multiple mutations may associate mutation(s) into nucleotide sequences or genes known for their attenuating properties such as aro genes, for example aroA (Homchampa P. et al., Veterinary Microbiology, 1994, 42: 35-44), and mutations into nucleotide sequences or genes according to the invention.

In one embodiment the mutants include at least two mutations, wherein for each mutation all or part of a specific gene or nucleic acid sequence is mutated as discussed herein. These specific genes or nucleic acid sequences include those comprising, or homologous to, sequences SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90 or 93, or their regulatory regions. Thus, mutants having two or more of the foregoing sequences mutated, e.g., deleted as discussed herein, are envisioned by the invention. Advantageously, mutants have two or more of the following sequences or sequences comprising, or homologous to, the following sequences mutated, e.g., deleted, as discussed herein: SEQ ID NO: 2, 6, 9, 12, 25, 31, 37, 40, 43, 46, 70, 75, 78, 81, 84, 87, 90 or 93, or their regulatory regions. More advantageously the specific genes or nucleic acid sequences that are mutated (e.g., the two or more that are mutated) include those comprising, or homologous to, the sequences SEQ ID NO: 6, 12, 25, 31, 37, 40, 46, 70, 75, 84, 87, 90 or 93, or their regulatory regions. The mutant can be a gram negative bacteria, and advantageously the mutant is a *Pasteurella*, such as a *P. multocida*, for example P-1059 or PM70.

Advantageously mutants having two or more of the following sequences, or their regulatory regions, mutated, e.g., deleted as discussed herein, are envisioned by the invention: SEQ ID NO: 37, 40, 75, 90 and 93, or their homologous nucleotide sequences.

Various embodiments include mutants having deletions of or in the genes or nucleic acid sequences comprising, or homologous to, sequences SEQ ID NO: 37 and 40; SEQ ID NO: 37 and 75; SEQ ID NO: 37 and 90; SEQ ID NO: 37 and 93; SEQ ID NO: 40 and 75; SEQ ID NO: 40 and 90; SEQ ID NO: 40 and 93; SEQ ID NO: 75 and 90; SEQ ID NO: 75 and 93; SEQ ID NO: 90 and 93, or their regulatory regions. The mutant can be a gram negative bacteria and advantageously the mutant is a *Pasteurella*, such as a *P. multocida*, for example P-1059 or PM70.

Methods to introduce the mutations into the specific genomic regions are known and will be apparent to the skilled person from this disclosure and the knowledge in the art. For instance, the whole gene or sequence to be mutated or a fragment is cloned into a vector and modified in order to abolish its expression and/or its biological activity. The vector is introduced into the bacteria, for example, by electroporation (e.g. Jablonski L. et al., Microbial Pathogenesis, 1992, 12, 63-68), or by conjugation (Lee M. D. et al., Vet. Microbiol., 1996, 50, 143-148). The modified DNA fragment is reintroduced into the bacterial genome by genetic recombination, advantageously by homologous recombination between the bacterial chromosome and the vector. As an example the vector can be a suicide plasmid as described in Cardenas (Cardenas M et al., Vet Microbiol 2001 May 3; 80(1): 53-61). Advantageously this vector additionally comprises, between the two flanking arms or regions (employed in homologous recombination) a polystop sequence (e.g., 6 stop codons, one in each reading frame) to block any possible translation.

The attenuated micro-organism of the invention, e.g. gram negative bacteria such as *P. multocida*, may further comprise at least one homologous or heterologous nucleic acid sequence inserted into its genome. This is useful for reproducing or replicating heterologous nucleic acid molecules and/or for expression of heterologous nucleic acid molecules, either in vivo or in vitro. The heterologous nucleic acid sequence advantageously codes for an immunogen, antigen or epitope from a pathogenic viral, parasitic or bacterial agent which is different from those naturally expressed by the attenuated micro-organism. This heterologous sequence may encode an immunogen, antigen or epitope from another strain of the micro-organism or bacteria, e.g., another *P. multocida* strain. An immunogen or antigen is a protein or polypeptide able to induce an immune response against the pathogenic agent or a secreted antigen of the pathogenic agent, and contains one or more epitopes; and epitope is a peptide or polypeptide which is able to induce an immune response against the pathogenic agent or a secreted antigen of the pathogenic agent.

Heterologous nucleic acid sequences which are suitable for this use in such a vector will be apparent to the skilled person (Fedorova N D and Highlander S K, Infect Immun 1997, 65(7): 2593-8) and include for example those coming from Pasteurellaceae family members (notably *Pasteurella multocida, Pasteurella haemolytica, Pasteurella anatipestifer, Actinobacillus pleuropneumoniae*), or from bacteria like *E. coli, Salmonella, Campylobacter*.

The heterologous sequence is advantageously inserted so as to be expressed by the microorganism in the host when administered in order to develop an immune response against both the attenuated micro-organism and said expressed immunogen. The heterologous sequence is advantageously inserted with or operably linked to or downstream from the regulatory elements allowing its expression, such as a promoter. Nucleotide sequences useful for the addressing and the secretion of the protein may also be added. Accordingly, leader or signal sequences may be included in expressed products to facilitate transport through the cell wall and/or secretion.

In one embodiment the homologous or heterologous sequence is inserted within the selected nucleotide sequence or the selected gene used for the attenuation; advantageously the homologous or heterologous sequence is inserted in one of the loci corresponding to the transposon insertion loci identified herein.

To improve the expression, the codon usage can be adapted to the bacterial vector used.

The attenuated mutants of the invention may also comprise a nucleic acid sequence encoding a therapeutic protein, an allergen, a growth factor or a cytokine or an immunomodulator or immunostimulator such as a GM-CSF, for instance a GM-CSF matched to the target species (e.g., if the attenuated vector is P. multocida, for administration to bovines, bovine GM-CSF could be expressed by the vector, for example with the expression by the vector of another heterologous protein, peptide, polypeptide, antigen, immunogen or epitope).

According to a further aspect of the invention attenuated micro-organisms are used to produce live attenuated immunogenic compositions or live attenuated vaccine compositions.

According to an advantageous aspect of the invention, the attenuated micro-organism is a gram negative bacteria, such as a Pasteurella, for instance, a P. multocida, for example P-1059 or PM70, mutated according to the invention.

Advantageously as described herein, the micro-organism may act as a recombinant vector to immunise and/or vaccinate animals or humans against infections caused by other agents than Pasteurella.

The immunogenic compositions or the vaccine compositions comprise the attenuated mutant and a pharmaceutically or veterinarily acceptable carrier, excipient, diluent or vehicle, and optionally a stabiliser and/or an adjuvant. The attenuated mutant can be a vector that additionally expresses nucleic acid molecules heterologous to the vector, such as a heterologous epitope, antigen, immunogen, and/or growth factor, cytokine, immunoregulator or immunostimulator.

The term of "immunogenic composition" covers herein any composition able, once it has been injected to animals or to a human to elicit an immune response against the targeted pathogen. The term of "vaccine composition" or "vaccine" covers herein any composition able, once it has been injected to animals or to a human to induce a protective immune response against the targeted pathogen.

The pharmaceutically or veterinarily acceptable vehicle may be water or saline, but it may, for example, also comprise bacteria culture medium.

The live attenuated bacteria according to the invention may be freeze-dried advantageously with a stabiliser. Freeze-drying can be done according to well-known standard freeze-drying procedures. The pharmaceutically or veterinarily acceptable stabilisers may be carbohydrates (e.g. sorbitol, mannitol, lactose, sucrose, glucose, dextran, trehalose), sodium glutamate (Tsvetkov T et al., Cryobiology 1983, 20(3): 318-23; Israeli E et al., Cryobiology 1993, 30(5): 519-23), proteins such as peptone, albumin, lactalbumin or casein, protein containing agents such as skimmed milk (Mills C K et al., Cryobiology 1988, 25(2): 148-52; Wolff E et al., Cryobiology 1990, 27(5): 569-75), and buffers (e.g. phosphate buffer, alkaline metal phosphate buffer).

An adjuvant may be used to make soluble the freeze-dried preparations.

Examples of adjuvants are oil-in-water, water-in-oil-in-water emulsions based on mineral oil and/or vegetable oil and non ionic surfactants such as block copolymers, Tween®, Span®. Other suitable adjuvants are for example vitamin E, saponins, and Carbopol®, aluminium hydroxide or aluminium phosphate ("Vaccine Design, The subunit and adjuvant approach", Pharmaceutical Biotechnology, vol. 6, Edited by Michael F. Powell and Mark J. Newman, 1995, Plenum Press New York).

The live attenuated bacteria may be stored at −70° C. in a medium containing glycerol.

Optionally, the immunogenic composition or vaccine can be combined with one or more immunogens, antigens or epitopes selected from other pathogenic micro-organisms or viruses in an inactivated or live form.

Another aspect of the invention is the nucleotide sequences or genes according to the invention, such as the nucleotide sequences or genes according to the invention designated SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90 and 93, and advantageously those designated SEQ ID NO: 1, 4, 5, 8, 11, 14, 15, 18, 21, 24, 27, 30, 33, 36, 39, 42, 45, 48, 51, 54, 57, 60, 63, 66, 69, 72, 73, 77, 80, 83, 86, 89, 92, 95, 96, 97.

Another aspect of the invention is the use of the nucleotide sequences or genes according to the invention, for the expression and the production of peptides, polypeptides or proteins, or more generally, expression products, e.g., immunogens, antigens or epitopes. In an embodiment, the polypeptides or peptides or proteins encoded by these nucleotide sequences or genes may be used as subunit immunogens or antigens or epitopes in immunogenic compositions or vaccines. Epitope determination procedures, such as, generating overlapping peptide libraries (Hemmer B. et al., Immunology Today, 1998, 19 (4), 163-168), Pepscan (Geysen H. M. et al., Proc. Nat. Acad. Sci. USA, 1984, 81 (13), 3998-4002; Geysen H. M. et al., Proc. Nat. Acad. Sci. USA, 1985, 82 (1), 178-182; Van der Zee R. et al., Eur. J. Immunol., 1989, 19 (1), 43-47; Geysen H. M., Southeast Asian J. Trop. Med. Public Health, 1990, 21 (4), 523-533; Multipin® Peptide Synthesis Kits de Chiron) and algorithms (De Groot A. et al., Nature Biotechnology, 1999, 17, 533-561), can be used in the practice of the invention, without undue experimentation.

Advantageous polypeptides are those having the amino acid sequences identified as SEQ ID NO: 3, 7, 10, 13, 17, 20, 23, 26, 29, 32, 35, 38, 41, 44, 47, 50, 53, 56, 59, 62, 65, 68, 71, 76, 79, 82, 85, 88, 91, 94, or those encoded by the nucleotide sequences SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93. Epitopes from these polypeptides can also be used advantageously.

The invention encompasses the equivalent polypeptides from another bacterium, such as a gram negative bacterium, advantageously a Pasteurellacaea family member, e.g. P. multocida, P. haemolytica, P. anatipestifer, A. pleuropneumoniae, and more advantageously in the genome of any one of the various strains of P. multocida are thus included by equivalence polypeptides whose amino acid sequences have at least about 70%, at least about 75%, at least about 80%, at least about 85%, at least about 90%, at least about 95%, and at least about 96, 97, 98 or 99% identity to one of the amino acid sequences identified as SEQ ID NO: 3, 7, 10, 13, 17, 20, 23, 26, 29, 32, 35, 38, 41, 44, 47, 50, 53, 56, 59, 62, 65, 68, 71, 76, 79, 82, 85, 88, 91, 94 and/or polypeptides that have the same biological function(s) than the polypeptides identified above with SEQ. The criteria for establishing the identity or the same biological function have been described above.

The invention also embraces the immunogenic fragments of these polypeptides, having at least a chain of 10 amino acids of the polypeptide, at least 20, such as at least 30, advantageously at least 50 and more advantageously at least 70, e.g., fragments of the polypeptides containing at least 10 contiguous amino acids of the polypeptide, advantageously at least 20 contiguous amino acids of the polypeptide, such as at least 30 and more advantageously at least 50 contiguous amino acids of the polypeptide, and even more advantageously at least 70 contiguous amino acids of the polypeptide. Of course, a fragment is less than the entire polypeptide. A fragment can be combined with other polypeptides, e.g., in fusion polypeptides; for instance, a polypeptide of the invention or fragment thereof can be a portion of a fusion polypeptide which includes another portion (another polypeptide), e.g., an immunogenicity-enhancing portion and/or a secretion-enhancing portion such as a lipoprotein portion that enhances immunogenicity or a signal or leader sequence portion. Accordingly, the invention envisions the expression of polypeptides, proteins, antigens, immunogens or epitopes— whether herein identified sequences or fragments thereof or those that are heterologous to the vectors of the invention—as fusions, e.g., as a portion of a fusion polypeptide, e.g., a fusion polypeptide that advantageously includes an immuogenicity enhancing portion such as a lipoprotein portion and/ or a secretion-enhancing portion such as a signal or leader sequence portion.

The polypeptides or fragments are produced advantageously by in vitro expression. The nucleotide sequences according to the invention (e.g. SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93) or fragments thereof are inserted into a vector, operably linked to regulatory elements such as promoter, ribosome binding region and terminator, and start codon and stop codon. Advantageous vectors are plasmids useful for in vitro expression in bacteria i.e. *Escherichia coli* (Mahona F et al., Biochimie 1994, 46(1): 9-14; Watt M A et al., Cell Stress Chaperones 1997, 2(3): 180-90; Frey J Res. Microbiol. 1992, 143(3): 263-9).

These polypeptides can also be synthesised chemically (Luo Y et al., Vaccine 1999, 17(7-8): 821-31).

An aspect of the invention is thus an immunogenic composition or vaccine comprising at least one polypeptide or fragment according to the invention (sub-unit immunogenic composition or vaccine) or at least one in vivo expression vector as described herein (live recombinant immunogenic composition or vaccine), and a pharmaceutically or veterinarily acceptable carrier, excipient, diluent or vehicle, and optionally an adjuvant. Examples of such ingredients have been described herein in relation to the live vaccine.

In another embodiment, these nucleotide sequences or their fragments may be inserted into recombinant vectors to produce live recombinant immunogenic compositions or vaccines able to express in vivo in the host the polypeptide encoded by this nucleotide sequence or fragment.

The in vivo expression vector can be a polynucleotide vector or plasmid (EP-A2-1001025; Chaudhuri P Res. Vet. Sci. 2001, 70(3), 255-6), viruses (e.g. adenovirus, poxvirus such as fowlpox (U.S. Pat. Nos. 5,174,993, 5,505,941 and 5,766,599) or canarypox (U.S. Pat. No. 5,756,103)) or bacteria i.e. *Escherichia coli* or *Salmonella* sp.

Polypeptides and fragments of the invention may also be used in therapy.

The polypeptides and fragments may also be used as reagents in antibody-antigen reactions. Accordingly, another aspect of the invention is thus a diagnostic method and/or kit for detecting infection by the gram negative bacterium. Kits, e.g. ELISA, can include at least one polypeptide or fragment according to the invention (e.g., at least one polypeptide identified by sequence herein or a fragment thereof as herein discussed).

Antibodies against the herein polypeptides or fragments (e.g., polypeptides identified by sequence herein or fragments thereof as herein discussed) can be used as a diagnostic reagent or in passive immunization or vaccination or in therapy. The amounts of antibody administered in passive immunization can be the same as or analogous to amounts used in the art, such that from the knowledge in the art, the skilled artisan can practice passive immunization without undue experimentation.

Another aspect of the invention is an antibody preparation comprising an antibody specific to a polypeptide or a fragment according to the invention and methods of diagnosis using the same. With respect to an antibody specific to a polypeptide, it is meant that the antibody binds preferentially to the polypeptide, e.g., the antibody binds to the polypeptide and not to other polypeptides or has a specificity to the polypeptide that is acceptably particular to the polypeptide such that the antibody can be used to isolate the polypeptide from a sample or detect its presence in a sample with no more than 5% false positives, using techniques known in the art or discussed in documents cited herein, including Sambrook, infra.

Antibodies can be polyclonal or monoclonal.

Methods for producing antibodies are well-known to the skilled artisan.

If polyclonal antibodies are desired, a selected animal (e.g. mouse, rabbit, goat, horse, etc.) is immunized with a polypeptide or a fragment. Serum from the immunized animal is collected and treated according to known procedures and possibly purified. See, e.g. Jurgens et al. J. Chrom., 1985, 348: 363-370.

The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g. J. E. Liddell "A practical guide to monoclonal antibodies" ed. John Wiley and sons, 1991, p.188; S. J. de StGroth et al. J. Immunol. Methods, 1980, 35(1-2), 1-21.

The nucleotide sequences according to the invention and their fragments may be used as a probe for hybridisation, e.g. in a diagnostic method.

Stringent hybridisation conditions are advantageously used. One can refer to those described by Sambrook et al., Molecular Cloning, A Laboratory Manual, Cold Spring Harbor Laboratory Press (1989), 1.101-1.104. Hybridisation under stringent conditions means that a positive hybridisation signal is still observed after washing for 1 hour with 1×SSC buffer and 0.1% SDS at 55° C., advantageously at 62° C. and more advantageously at 68° C., e.g., for 1 hour in 0.2×SSC buffer and 0.1% SDS at 55° C., such as at 62° C. and advantageously at 68° C.

One can also characterize nucleotide sequences by their ability to bind under stringent hybridization conditions. Thus, the invention can envision herein identified nucleic acid sequences and nucleic acid molecules that bind thereto under stringent hybridization conditions.

The nucleotide sequences according to the invention and their fragments may be used as primers for PCR or in a similar method involving amplification and/or hybridization, e.g., for detection of gram negative bacteria in any media, for example tissue samples, biological fluids, water, food.

Advantageously use is made of nucleotide sequence fragments which have at least 20 contiguous, such as at least 30 contiguous, e.g., at least 50 contiguous, for instance at least 70 contiguous or more advantageously at least 100 contiguous nucleic acids of nucleotide sequences or genes according to the invention, e.g., of SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93.

Further, the present invention relates to methods to immunise against or to prevent bacterial infection or protect against bacterial infection in animals, advantageously animals susceptible thereto, such as avian, rabbit, bovine and porcine species, and more advantageously in avian species such as chicken, turkey and duck (including breeders, broilers and layers) or in a human.

According to these methods, (1) a live attenuated immunogenic composition or vaccine of the invention, or (2) a sub-unit immunogenic composition or vaccine of the invention, or (3) a live recombinant immunogenic composition or vaccine of the invention, or combinations thereof, are administered. Of course, embodiments of the invention may be employed with other vaccines or immunogenic compositions that are not of the invention, e.g., in prime-boost processes, such as where a vaccine or immunogenic composition of the invention is administered first and a different vaccine or immunogenic composition is administered thereafter, or vice versa.

The administration may be notably made by intramuscular (IM), intradermal (ID) or subcutaneous (SC) injection or via intranasal, intratracheal or oral administration. The immunogenic composition or the vaccine according to the invention is advantageously administered by syringe, needleless apparatus (like for example Pigjet, Avijet, Dermojet or Biojector (Bioject, Oregon, USA)), spray, drinking water, eye-drop.

Advantageous administrations for the live attenuated immunogenic composition or vaccine are in ovo, via the oral (e.g. drinking water, whole body spray), ocular (e.g. eye-drop, whole body spray), tracheal (e.g. spray), intradermal, subcutaneous (SC) or intramuscular (IM) routes.

The quantity of live attenuated micro-organisms can be determined and optimised by the skilled person, without undue experimentation from this disclosure and the knowledge in the art. Generally an animal (including a human) may be administered approximately $10^4$-$10^9$ CFUs, advantageously approximately $10^5$-$10^8$ CFUs and more advantageously approximately $10^6$-$10^7$ CFUs in a single dosage unit.

By intramuscular route an avian animal may be administered approximately $10^4$-$10^7$ CFUs, advantageously approximately $10^5$-$10^6$ CFUs in a single dosage unit. The volume of one single dosage unit can be between about 0.2 ml and about 0.5 ml and advantageously about 0.3 ml. By oral, tracheal or ocular route an avian animal may be administered approximately $10^5$-$10^8$ CFUs, advantageously approximately $10^6$-$10^7$ CFUs in a single dosage unit. For spray administration the volume is adjusted to the apparatus and the size of droplets, from about 30 to about 600 ml for about 1000 animals and advantageously about 0.2 ml per animal.

For bovine and porcine animals, the advantageous routes are IM and SC. The animal may be administered approximately $10^4$-$10^9$ CFUs, advantageously approximately $10^5$-$10^8$ CFUs in a single dosage unit. The volume of one single dosage unit can be between about 0.2 ml and about 5.0 ml and advantageously between about 0.5 ml and about 2.0 ml and more advantageously about 1.0 ml.

Rabbits may be administered via IM or SC route approximately $10^4$-$10^8$ CFUs, advantageously approximately $10^5$-$10^7$ CFUs in a single dosage unit. The volume of one single dosage unit can be between about 0.2 ml and about 0.5 ml and advantageously about 0.5 ml. They may also be administered via ID route approximately $10^4$-$10^8$ CFUs, advantageously approximately $10^5$-$10^7$ CFUs in a single dosage unit. The volume of one single dosage unit can be between about 0.1 ml and about 0.2 ml.

The invention will now be further described by way of the following non-limiting examples.

EXAMPLES

Example 1

Construction of a Library of Signature Tagged *P. multocida* Transposon Mutants (STM Screening)

Construction of the Tagged SM10λpir pLOF/km Transformants

Tags were produced as described in Hensel et. al., (Science, 1995, 269:400-403). Initially tagged-pUTminiTn5Km2 plasmids were selected that contain tags that hybridise well but do not cross hybridise with each other. The mini-Tn5 transposon in the tagged pUTminiTn5Km2 vector was found not to transpose in several strains of *Pasteurella multocida*. In contrast the transposon mini-Tn10 has been shown to function in *P. multocida* (Lee et. al., Vet Microbiol, 1996, 50:143-8). The pre-selected tags were therefore transferred from the pUTminiTn5 vectors into the miniTn-10 containing plasmid pLOF/Km (Herrero et al., J. Bacteriology, 1990, 172: 6557-6567). The tags were amplified by PCR using primers that bind to the pUTminiTn5Km2 vector, either side of the KpnI site into which the tags were cloned. These primers included sequences for the restriction enzyme SalI. The PCR products were then digested with SalI and cloned into the SalI site of a modified version of the pLOF/Km vector, in which a SalI site has replaced the unique SfiI cloning site. The tagged pLOF/Km plasmids were then transformed into the *E. coli* strain SM10Xλpir ($KM^r$, thi, thr, leu, tona, lacy, supE, recA::RP4-2-Tc::Muλpir) (Miller V. L. et al., J. Bacteriol., 1988, 170: 2575-83). This strain can mobilise plasmids such as pLOF/Km into recipient bacteria by conjugation.

Methods of Selecting and Counter-selecting

The conjugation process requires a method of selecting for the recipient *P. multocida*, which have acquired the plasmid pLOF/KM and a method of counter-selection against the *E. coli* SM10λpir donor.

In the method of selecting the recipient *P. multocida* are selected for using kanamycin, which is encoded by the mini-Tn10 transposon.

Initially for counter-selection against the *E. coli* donor in conjugations, a spontaneously streptomycin resistant mutant of *Pasteurella* strain P-1059 was used. However it appeared that this strain was attenuated in virulence for turkeys and thus was not usable here. *Pasteurella multocida* strains can grow on a chemically defined media (CDM) (Hu et. al., Infection and Immunity 1986, 804-810). A modified version of this chemically defined medium containing agar but not containing leucine was utilised to allow counter-selection against the E. coli donor. The Pasteurella strain was able to grow on this medium, the composition of which is given in table 1, whereas the E. coli SM10λpir strain, which is a leucine auxotrophe did not.

TABLE 1

| Component | Concentration g/litre |
| --- | --- |
| Noble Agar | 20 |
| $Na_2HPO_4.12H_2O$ | 32.31 |
| $KH_2PO_4$ | 1.368 |
| NaCl | 1.196 |
| Glucose | 6.0 |
| L-Arginine hydrochloride | 0.24 |
| L-cysteine Hydrochloride | 0.12 |
| L-Serine | 0.2 |
| L-glutamic acid | 0.15 |
| L-isoleucine | 0.064 |
| L-phenylalanine | 0.095 |
| L-Aspartic acid | 1.6 |
| L-tyrosine | 0.08 |
| Thiamine hydrochloride | 0.0002 |
| $MgSO_4.7H_2O$ | 0.246 |
| Calcium pantothenate | 0.004 |
| Nicotinamide | 0.01 |
| Orotic acid | 0.003 |

Passaging of P. multocida Strain on CDM Media

A lyophilised ampoule of P. multocida strain (USDA P-1059, available from the American Type Culture Collection, accession number ATCC 15742) was revived by the addition of 200 µl of BHI (brain-heart infusion) and an aliquot of the suspension streaked onto a BHI agar plate and the plate incubated at 37° C. overnight. Colony material from this plate was used to inoculate a BHI broth culture, which was incubated with shaking at 37° C. overnight. Glycerol was added to a final concentration of 15% v/v and aliquots were stored frozen at −80° C. A sample from of one of these frozen aliquots was streaked onto a BHI agar plate and incubated overnight. Colony material from this BHI plate was then streaked onto CDM agar plates with the composition given in table 1 and incubated at 37° C. for 3 days. Colony material from this CDM plate was inoculated into a BHI broth culture and incubated with shaking at 37° C. overnight. Glycerol was added to this culture to a final concentration of 15% v/v and aliquots frozen at −80° C. This strain was termed 16084 (CDM).

Construction of the Mutant Bank

The tagged SM10λpir pLOF/km transformants were conjugated with the 16084 (CDM) P. multocida strain. To minimise the isolation of sibling mutants (mutants with the transposon located in the same position that arise due to replication of the mutant during the conjugation procedure) each tagged SM10λpir transformant was conjugated with the P. multocida strain in at least three separate conjugations. Pasteurella transposon mutants were selected on CDM agar plates supplemented with 50 µg/ml kanamycin.

The kanamycin resistant mutants for each of the tagged transposons were then streaked to form single colonies twice on BHI kanamycin 50 µg/ml agar plates. Single colonies were then inoculated into BHI broth cultures, grown overnight at 37° C. with shaking. Glycerol was then added to a final concentration of 15% v/v and the mutants stored at −80° C. in individual vials.

Example 2

Screening of the Signature-Tagged Pasteurella Mutant Bank for Mutants Attenuated in Virulence for Turkeys Cultures of the P. multocida mutants were grown for inoculation of turkeys by mixing 20 µl of each of the glycerol stocks of the mutants obtained in example I with 200 µl of BHI culture medium, supplemented with 50 µg/ml of kanamycin, and placing in 96 well microtitre dishes. These microtitre dishes were incubated in static conditions for about 18 hours at 37° C. Then 10 µl aliquots of the 18 hour cultures of each mutant were mixed with 200 µl of BHI culture medium supplemented with 50 µg/ml of kanamycin in a fresh microtitre plate and the plate incubated at 37° C. for approximately 4 hours. The cultures were stopped in the exponential phase of growth and 100 µl of the cultures of each mutant were transferred to a fresh microtitre plate and used for determination of the optical density (OD) at 650 nm.

The inocula or input pools were formed by mixing the remaining 100 µl of the 4 hour cultures. Each input pool consisted of 48 different mutants. The titre of these pooled suspensions were determined by FACS (fluorescence activated cell sorter) analysis of 100 µl aliquots. Aliquots (1 ml) of the pooled suspension were then diluted in physiologically buffered water to obtain a suspension with a titre of $2.10^7$ cfu/ml. Groups of 5 three-week-old turkeys were then inoculated intramuscularly with 0.5 ml aliquots of this suspension ($10^7$ cfu per animal). The serological status of the turkeys prior to inoculation was determined by screening for the presence of antibodies to Pasteurella in blood samples taken one day before inoculation. The cells from the remainder of the input pools were harvested by centrifugation and chromosomal DNA extracted from the cell pellets.

Approximately 14 hours after inoculation 1 ml blood samples were taken from 3 of the 5 turkeys. Dilution series ($10^{-4}$ to $10^{-7}$) of the blood samples were plated onto Columbia agar plates supplemented with 5% sheeps blood. The plates were incubated at 37° C. for 24 hours after which time approximately 10000 Pasteurella colonies were resuspended in BHI medium. These suspensions, which are termed the output pool, were then centrifuged and chromosomal DNA extracted from the cell pellet.

Pasteurella mutants that were present in the input pool but were not re-isolated from the turkeys were identified by PCR amplification of the signature tags present in DNA samples from the input and output pools, and hybridisation of the amplified PCR products against dot blots loaded with DNA encoding the signature tags, as described in Hensel et al. (Science 1995, 269:400-403). These mutants were considered as potentially attenuated in virulence. This attenuation was confirmed by screening for a lack of mortality after single infections of the potentially mutants in turkeys.

Example 3

Confirmation of the Attenuation in Virulence for Turkeys of the P. multocida Mutants The transposon mutants identified as potentially attenuated in Example 2 or the mutants which have limited ability to grow in culture, were revived by mixing 20 µl of the glycerol stocks with 200 µl of BHI culture medium supplemented with 50 µg/ml of kanamycin in microtitre dishes. These microtitre dishes were incubated in static conditions for 18 hours at 37° C. Then 10 µl aliquots of each mutant of these cultures were taken and mixed with 200 µl of BHI medium, supplemented with 50 µg/ml of kanamycin in a fresh microtitre plate and this plate incubated in static conditions for about 4 hours. The cultures were stopped in the exponential phase of growth and 100 µl of the cultures of each mutant were transferred to a fresh microtitre plate and used for determination of the optical density (OD) at 650 nm. The cultures of each of the mutants were then diluted 1 in 10000 in physiologically buffered water to obtain a concentration of approximately $2.10^4$ cfu/ml. Aliquots (0.5 ml) of these dilutions were then inoculated intramuscularly into 2 five-week-old turkeys ($10^4$ cfu per animal). The serological status of a few animals from each group of turkeys was determined from blood samples taken the day before inoculation. The turkeys were monitored for the following 7 days for mortality. Of the mutants tested 72 did not result in mortality in either of the two birds inoculated. These 72 mutants were considered attenuated in virulence.

Example 4

Characterisation of Transposon Insertion Mutants Identified After Screening in Turkeys The transposon insertion sites in the genome of attenuated *P. multocida* mutants were identified by cloning the DNA flanking one side of the transposon insertion, either by Inverse PCR or by arbitrarily primed PCR.

These mutants were revived from the −80° C. glycerol stocks by streaking an aliquot onto BHI kanamycin 50 μg/ml agar plates. Single colonies were then used to inoculate BHI broth cultures from which chromosomal DNA was prepared.

For Inverse PCR the chromosomal DNA was digested with a restriction enzyme that has a 4 base pairs recognition site, such as Tsp509I, αTaqI or RsaI. The DNA is then ligated in a large volume to encourage intra-molecular ligation. The DNA flanking the transposon is then amplified from this ligated DNA template using outwardly facing primers that anneal to known sequence of the transposon, such as StipJ (SEQ ID NO: 98, 20 mer) (5' ATC TGA TCC TTC AAC TCA GC 3'), StipA (SEQ ID NO: 99, 19 mer) (5° CGC AGG GCT TTA TTG ATT C 3'), KTGRI (SEQ ID NO: 100, 27 mer) (5' GCG GAA TTC GAT GAA TGT TCC GTT GCG 3'), Tn10IR1 (SEQ ID NO: 101, 20 mer) (5' TTT ACC AAA ATC ATT AGG GG 3') and Tn10IR4 (SEQ ID NO: 102, 19 mer) (5' GAT CAT ATG ACA AGA TGT G 3'). These Inverse PCR products are then cloned and sequenced.

For arbitrarily primed PCR the chromosomal DNA was used as a template in a first round PCR reaction with one outwardly facing primer that anneals to the transposon, such as StipA, and an arbitrary primer, such as arb1 (SEQ ID NO: 103, 35 mer) (5' GGC CAC GCG TCG ACT AGT ACN NNN NNN NNN GAT AT 3') or arb6 (SEQ ID NO: 104, 35 mer) (5' GGC CAC GCG TCG ACT AGT ACN NNN NNN NNN CAG CC 3'). The annealing temperature of this first round PCR reaction is initially set very low, with the annealing temperature being raised in subsequent cycles. A portion of the products of this first round PCR is then used as a template in a second round PCR. This second round PCR utilises another outwardly facing primer, such as KTGRI, which anneals to the transposon at a position that is closer to the end of the transposon than the primer used in the first round PCR. The other primer used in this second round PCR has the same sequence as the 20 bases of known sequence at the 5' end of the arbitrary primer used in the first round PCR, such arb2 (SEQ ID NO: 105, 20 mer) (5' GGC CAC GCG TCG ACT AGT AC 3'). The PCR products of this second PCR are then cloned and sequenced.

The sequences obtained were then analysed to identify open reading frames (ORF), which may be disrupted by the transposon and were also used to search for similar sequences currently available in the EMBL database and in the genome sequence of the *Pasteurella multocida* strain PM70, determined by the University of Minnesota (May B J et al., Proc. Natl. Acad. Sci. USA, 2001, 98(6): 3460-5).

For information, in the following nucleotide sequences, N is corresponding to any nucleic acid (A or C or G or T).

Mutants 1G4, 3F4, 3G12, 12D6 and 14C10

The mutants 1G4, 3F4 and 12D6 have exactly the same transposon insertion site. The DNA sequence flanking the transposon insertion site is given in SEQ ID NO: 1 (775 mer). The transposon is inserted immediately at the 5' end of this sequence.

A start codon is located at positions 179-181 of the sequence SEQ ID NO: 1.

For the mutant 3G12, the DNA sequence flanking the transposon insertion site is given in SEQ ID NO: 95 (101 mer). The transposon is inserted immediately at the 5' end of this sequence.

For the mutant 14C10, the DNA sequence flanking the transposon insertion site is given in SEQ ID NO: 96 (220 mer). The transposon is inserted immediately at the 3' end of this sequence.

Four other Pasteurellaceae proteins and genes were identified by blasts done with a 60 amino acid sequence encoded by SEQ ID NO: 1.

| Strain | Gene (Genbank ref.) | Protein (Genbank ref.) | % of identity |
|---|---|---|---|
| *P. multocida* taxon 747 | PhyA (AF067175) | PhyA (AAC67248) | 100% over 60 amino acids |
| *P. multocida* PM70 | PM0773 (AE006115) | PhyA (AAK02857) | 98% over 60 amino acids |
| *P. multocida* P4218 | PhyA (AF302467) | PhyA (AAK17919) | 98% over 60 amino acids |
| *P. multocida* P934 | PhyA (AF302465) | PhyA (AAK17907) | 95% over 60 amino acids |

The location of the transposon in mutants 1G4, 3F4 and 12D6 corresponds to position 8507-8508 of the *Pasteurella multocida* PM70 genome sequence, Genbank Accession number AE006115. The location of the transposon in the mutant 3G12 corresponds to position 8609-8610 of the AE006115 sequence. The location of the transposon in the mutant 14C10 corresponds to position 8517-8518 of the AE006115 sequence. The transposon disrupts a homologue of the PM70 gene PM0773, PhyA. The PhyA gene is predicted to be involved in capsule synthesis. The nucleotide sequence of PM0773 is herein identified as SEQ ID NO: 2 and its amino acid sequence as SEQ ID NO: 3.

Mutants 1G8, 9D1 and 9D8

In mutant 1G8, the transposon is inserted immediately at the 3' end of the sequence SEQ ID NO: 4 (226 mer). This sequence has two open reading frames (+2 and 2) encoding potential longer proteins. The ORF according to the invention is in frame −2.

The transposon inserted in mutant 9D1 is immediately at the 3' end of the sequence SEQ ID NO: 5 (87 mer).

The transposon inserted in mutant 9D8 is after position 225 of the sequence SEQ ID NO: 4.

The transposons in mutants 1G8, 9D1 and 9D8 disrupt a homologue of the PM70 gene, PM0871. The locations of the transposons in these mutants correspond to positions 9849-9850 (mutant 1G8), 8899-8900 (mutant 9D1) or 9848-9849 (mutant 9D8) of the *Pasteurella multocida* PM70 genome sequence Genbank accession number AE006125. The nucleotide sequence of PM0871 is herein identified as SEQ ID NO: 6 and its amino acid sequence as SEQ ID NO: 7.

One other Pasteurellaceae gene/protein was identified by blasts done with SEQ ID NO: 7. This is Haemophilus influenzae HI1586 (Genbank accession numbers U32832 and AAC23234). We find an identity of 72% over 507 amino acids between PM0871 and HI1586.

Mutant 2F2

The DNA sequence flanking the transposon insertion site is given in SEQ ID NO: 8 (78 mer). The transposon is immediately at the 5' end of this sequence. This sequence has three open reading frames (+1, +2 and −1) encoding potential longer proteins. The ORF according to the invention is in frame +2.

The transposon in mutant 2F2 disrupts a homologue gene of PM70 gene PM1727. This transposon is located at a position which corresponds to 644-645 of the *Pasteurella multocida* PM70 sequence, Genbank accession number AE006210 (PM1727). The nucleotide sequence of PM1727 is herein identified as SEQ ID NO: 9 and its amino acid sequence as SEQ ID NO: 10.

One other Pasteurellaceae gene/protein was identified by blasts done with SEQ ID NO: 10. This is *Haemophilus influenzae* HI0621 (Genbank accession numbers U32744 and AAC22281). We find an identity of 77% over 183 amino acids between PM1727 and HI0621.

PM1727 is a member of a superfamily of hydrolases, in particular it is related to histidinol phosphate phosphatases.

Mutant 3A2

The DNA sequence flanking the transposon insertion site is given in SEQ ID NO: 11 (467 mer). The transposon is immediately at the 5' end of this sequence.

A stop codon is located at positions 428-430.

The transposon in mutant 3A2 is located at a position which correspond to 5103-5104 of the *Pasteurella multocida* PM70 sequence, Genbank accession number AE006094 (PM0586). The nucleotide sequence of PM0586 is herein identified as SEQ ID NO: 12 and its amino sequence as SEQ ID NO: 13.

Two other Pasteurellaceae genes and proteins were identified by blasts done with SEQ ID NO: 13. These genes and proteins are *Pasteurella haemolytica* A1 PlpD (Genbank accession numbers AF058703 and AAC32565) and *Haemophilus somnus* 31 kDa (Genbank accession numbers L07795 and AAA24941). We find an identity of 73% over 276 amino acids between PM0586 and *P. haemolytica* PlpD and of 71% over 273 amino acids between PM0586 and *H. somnus* 31 kDa.

PlpD and PM0586 are members of the ompA protein family.

Mutant 3D3

The DNA sequences flanking the both sides of the transposon insertion site are given in SEQ ID NO: 14 (204 mer, transposon at the 5' end) and SEQ ID NO: 15 (35 mer, transposon at the 5' end).

A stop codon is located at positions 7-9 of SEQ ID NO: 14 and at positions 33-35 of SEQ ID NO: 15.

One other Pasteurellaceae gene/protein was identified by blasts done with SEQ ID NO: 14 and its encoded amino acid sequence (65 amino acids). We find an identity of 100% over 65 amino acids with PM0064 protein. The location of the transposon in mutant 3D3 corresponds to positions 4778-4779 or 4787-4788 of the *Pasteurella multocida* PM70 genome sequence, Genbank accession number AE006042, positions deduced from SEQ ID NO: 14 and 15 respectively. This difference is likely to be due to insertion of the transposon resulting in the duplication of a few nucleotides at the transposon insertion site. Position 4788 is located in the PM0064 gene. Position 4778 is 6 bp downstream of the stop codon of PM0064. The nucleotide sequence of PM0064 is herein identified as SEQ ID NO: 16 and its amino acid sequence as SEQ ID NO: 17.

Other gram negative bacteria genes and proteins were identified by blasts done with SEQ ID NO: 17.

| Strain | Gene (Genbank ref.) | Protein (Genbank ref.) | % of identity |
|---|---|---|---|
| Haemophilus influenzae | HI0017 (U32687) | HI0017 (AAC21695) | 81% over 127 amino acids |
| Escherichia coli K12 | YfiD (AE000344) | yfiD (AAC75632) | 81% over 127 amino acids |
| Salmonella typhi | STY2839 (AL627275) | yfiD (CAD02795) | 81% over 127 amino acids |
| Salmonella typhimurium | STM2646 (AE008820) | yfiD (AAL21540) | 81% over 127 amino acids |
| Serratia liquefaciens | OrfX (X66505) | OrfX (CAA47136) | 79% over 127 amino acids |
| Yersinia pestis | YPO2705 (AJ414153) | YPO2705 (CAC92944) | 79% over 127 amino acids |
| Vibrio cholerae | VC2361 (AE004306) | VC2361 (AAF95504) | 73% over 127 amino acids |

Mutant 3D8

The DNA sequence flanking the transposon insertion site is given in SEQ ID NO: 18 (75 mer). The transposon is immediately at the 3' end of this sequence.

The location of the transposon in mutant 3D8 corresponds to between positions 7769-7770 of the *Pasteurella multocida* PM70 genome sequence, Genbank accession number AE006080. The transposon disrupts a homologue of the PM70 gene PM0445. The nucleotide sequence of PM0445 is herein identified as SEQ ID NO: 19 and its amino acid sequence as SEQ ID NO: 20.

Mutant 3E1

The DNA sequence flanking the transposon insertion site is given in SEQ ID NO: 21 (229 mer). The transposon is immediately at the 3' end of this sequence.

The location of the transposon in mutant 3E1 corresponds to between positions 9195-9196 of *Pasteurella multocida* PM70 genome sequence, Genbank accession number AE006133. The transposon disrupts a homologue of the PM70 gene PM0940. The nucleotide sequence of PM0940 is herein identified as SEQ ID NO: 22 and its amino acid sequence as SEQ ID NO: 23.

Other gram negative bacteria genes and proteins were identified by blasts done with SEQ ID NO: 17.

| Strain | Gene (Genbank ref.) | Protein (Genbank ref.) | % of identity |
|---|---|---|---|
| *Haemophilus influenzae* | HI0075 (U32693) | nrdD (AAC21751) | 87% over 713 amino acids |
| *Escherichia coli* K12 | nrdD (AE000495) | nrdD (AAC77195) | 76% over 709 amino acids |
| *Salmonella typhi* | STY4791 (AL627283) | nrdD (CAD06912) | 76% over 709 amino acids |
| *Salmonella typhimurium* | STM4452 (AE008908) | nrdD (AAL23272) | 76% over 709 amino acids |
| *Yersinia pestis* | YPO3464 (AJ414157) | nrdD (CAC92683) | 75% over 709 amino acids |
| *Vibrio cholerae* | VCA0511 (AE004381) | VCA0511 (AAF96414) | 74% over 709 amino acids |

Mutant 3H2

The DNA sequence flanking the transposon insertion site is given in SEQ ID NO: 24 (58 mer). The transposon is immediately at the 3' end of this sequence. This sequence has two open reading frames (+1 and −3) encoding potential longer proteins. The ORF according to the invention is in frame +1.

One other Pasteurellaceae gene was identified by blasts done with SEQ ID NO: 24 and with its encoded amino acid sequence (19 amino acids). We find an identity of 100% over 19 amino acids with PM1951 protein. The location of the transposon in mutant 3H2 corresponds to between positions 9418-9419 of the *Pasteurella multocida* PM70 sequence, Genbank accession number AE006231 (PM1951, uvrA). The nucleotide sequence of PM1951 is herein identified as SEQ ID NO: 25 and its amino acid sequence as SEQ ID NO: 26.

Other gram negative bacteria genes and proteins were identified by blasts done with SEQ ID NO: 26.

| Strain | Gene (Genbank ref.) | Protein (Genbank ref.) | % of identity |
|---|---|---|---|
| *Haemophilus influenzae* | UvrA (U32711) | UvrA (AAC21915) | 89% over 943 amino acids |
| *Escherichia coli* K12 | UvrA (AE000479) | UvrA (AAC77028) | 80% over 940 amino acids |
| *Yersinia pestis* | UvrA (AJ414142) | UvrA (CAC89185) | 80% over 943 amino acids |
| *Vibrio cholerae* | UvrA (AE004127) | UvrA (AAF93567) | 80% over 940 amino acids |
| *Salmonella typhi* | UvrA (AL627282) | UvrA (CAD09238) | 80% over 941 amino acids |
| *Salmonella typhimurium* | UvrA (AE008898) | UvrA (AAA27250) | 80% over 941 amino acids |
| *Pseudomonas aeruginosa* | UvrA (AE004840) | UvrA (AAG07622) | 75% over 943 amino acids |

UvrA is a DNA repair ABC excision nuclease.

Mutant 4D6

The DNA sequence flanking the transposon insertion site is given in SEQ ID NO: 27 (54 mer). The transposon is immediately at the 5' end of this sequence. This sequence has two open reading frames (+1 and −2) encoding potential longer proteins. The ORF according to the invention is in frame +1.

The location of the transposon in mutant 4D6 corresponds to between positions 6492-6493 of the *Pasteurella multocida* PM70 sequence, Genbank accession number AE006036. The transposon disrupts a homologue of the PM70 genePM0032 or hktE. The nucleotide sequence of PM0032 is herein identified as SEQ ID NO: 28 and its amino acid sequence as SEQ ID NO: 29. One other Pasteurellaceae gene/protein was identified by blasts done with SEQ ID NO: 29. This is *Actinobacillus actinomycetemcomitans* catalase (Genbank accession numbers AF162654 and AAF17882). We find an identity of 85% over 482 amino acids between PM0032 and *A. actinomycetemcomitans* catalase.

HktE is a catalase.

Mutant 4F4 and 12A5

For the mutant 4F4, the DNA sequence flanking the transposon insertion site is given in SEQ ID NO: 30 (172 mer). The transposon is immediately at the 3' end of this sequence. For the mutant 12A5, the DNA sequence flanking the transposon insertion site is given in SEQ ID NO: 97 (546 mer). The transposon is inserted immediately at the 5' end of this sequence.

Four other Pasteurellaceae genes and proteins were identified by blasts done with the 57 amino acid sequence encoded by SEQ ID NO: 30.

| Strain | Gene (Genbank ref.) | Protein (Genbank ref.) | % of identity |
|---|---|---|---|
| *P. multocida* taxon 747 | HyaC (AF067175) | HyaC (AAC67251) | 96% over 57 amino acids |
| *P. multocida* PM70 | PM0776 (AE006116) | AAK02860 | 96% over 57 amino acids |
| *P. multocida* P4218 | FcbC (AF302467) | FcbC (AAK17922) | 91% over 57 amino acids |
| *P. multocida* P934 | DcbC (AF302465) | DcbC (AAK17904) | 88% over 57 amino acids |

The location of the transposon in mutant 4F4 corresponds to between positions 5272-5273 of the *Pasteurella multocida* PM70 genome sequence, Genbank accession number AE006116. The location of the transposon in mutant 12A5 corresponds to between positions 5275-5276 of the AE006116 sequence. The transposon disrupts a homologue of the PM70 gene PM0776. The nucleotide sequence of PM0776 is herein identified as SEQ ID NO: 31 and its amino acid sequence as SEQ ID NO: 32. These proteins are UDP glucose dehydrogenases.

Mutant 4F 12

The DNA sequence flanking the transposon insertion site is given in SEQ ID NO: 33 (226 mer). The transposon is immediately at the 5' end of this sequence.

The location of the transposon in mutant 4F12 corresponds to between positions 9263-9264 of the *Pasteurella multocida* PM70 sequence, Genbank accession number AE006038. The transposon disrupts a homologue of the PM70 gene PM0048 or fadR. The nucleotide sequence of PM0048 is herein identified as SEQ ID NO: 34 and its amino acid sequence as SEQ ID NO: 35. FadR is a homologue of an *E. coli* protein which is a transcription regulator of fatty acid metabolism, affecting several fatty acid biosynthesis (fab) and fatty acid degradation (fad) genes.

Mutant 4G11

The DNA sequence flanking the transposon insertion site is given in SEQ ID NO: 36 (214 mer). The transposon is immediately at the 3' end of this sequence.

One other Pasteurellaceae gene was identified by blasts done with SEQ ID NO: 36 and its encoded amino acid sequence (70 amino acids). We find an identity of 100% over 70 amino acids with PM1024 protein. The location of the transposon in mutant 4G11 corresponds to between positions 3532-3533 of the *Pasteurella multocida* PM70 genome sequence, Genbank accession number AE006143. The transposon disrupts a homologue of the PM70 gene PM1024 or HtpG. The nucleotide sequence of PM1024 is herein identified as SEQ ID NO: 37 and its amino acid sequence as SEQ ID NO: 38.

Other gram negative bacteria genes and proteins were identified by blasts done with SEQ ID NO: 38.

HtpG is a heat shock protein.

Mutant 5D5

The DNA sequence flanking the transposon insertion site is given in SEQ ID NO: 39 (252 mer). The transposon is immediately at the 3' end of this sequence.

The location of the transposon in mutant 5D5 corresponds to between positions 5695-5696 of the *Pasteurella multocida* PM70 genome sequence, Genbank accession number AE006188. The transposon disrupts a homologue of the PM70 gene PM1517 or PlpE). The nucleotide sequence of PM1517 is herein identified as SEQ ID NO: 40 and its amino acid sequence as SEQ ID NO: 41.

PlpE is predicted to be a membrane lipoprotein.

The 5D5 mutant was deposited under Budapest Treaty in the Pasteur Institute Collection and is available under the accession number CNCM I-3000.

Mutant 5F11

The DNA sequence flanking the transposon insertion site is given in SEQ ID NO: 42 (546 mer). The transposon is immediately at the 5' end of this sequence.

A stop codon is located at positions 148-150.

The location of the transposon in mutant 5F11 corresponds to between positions 572-573 of the *Pasteurella multocida* PM70 genome, Genbank accession number AE006150. The transposon disrupts a homologue of the PM70 gene PM1087 or NifR3. The nucleotide sequence of PM1087 is herein identified as SEQ ID NO: 43 and its amino acid sequence as SEQ ID NO: 44.

One other Pasteurellaceae gene/protein was identified by blasts done with SEQ ID NO: 44. This is *Haemophilus influenzae* HI0979 (Genbank accession numbers U32778 and AAC22639). We find an identity of 78% over 332 amino acids between PM1087 and HI0979. NifR3 is a nitrogenase regulatory gene.

Mutant 5G9 he DNA sequence flanking the transposon insertion site is given in SEQ ID NO: 45 (43 mer). The transposon is immediately at the 3' end of this sequence. This sequence has three open reading frames (+2, +3 and −1) encoding potential longer proteins. The ORF according to the invention is in frame +2.

| Strain | Gene (Genbank ref.) | Protein (Genbank ref.) | % of identity |
| --- | --- | --- | --- |
| *Actinobacillus actinomycetemcomitans* | HtpG (U26968) | HtpG (AAC44732) | 88% over 625 amino acids |
| *Haemophilus influenzae* | HtpG (U32695) | HtpG (AAC21778) | 86% over 625 amino acids |
| *Escherichia coli* K12 | HtpG (AE000153) | HtpG (AAC73575) | 76% over 621 amino acids |
| *Yersinia pestis* | HtpG (AJ414155) | HtpG (CAC92355) | 76% over 622 amino acids |
| *Salmonella typhi* | STY0531 (AL627267) | HtpG (CAD04972) | 76% over 621 amino acids |
| *Salmonella typhimurium* | HtpG (AE008718) | HtpG (AAL19441) | 75% over 621 amino acids |

The 4G11 mutant was deposited under Budapest Treaty in the Pasteur Institute Collection and is available under the accession number CNCM I-2999.

Four other Pasteurellaceae genes and proteins were identified by blasts done with 14 amino acid sequence encoded by SEQ ID NO: 45.

| Strain | Gene (Genbank ref.) | Protein (Genbank ref.) | % of identity |
|---|---|---|---|
| P. multocida P4218 | FcbE (AF302467) | FcbE (AAK17920) | 100% over 14 amino acids |
| P. multocida PM70 | PM0774 (AE006116) | HyaE (AAK02858) | 100% over 14 amino acids |
| P. multocida taxon 747 | HyaE (AF067175) | HyaE (AAC67249) | 100% over 14 amino acids |
| P. multocida P934 | DcbE (AF302465) | DcbE (AAK17906) | 71% over 14 amino acids |

The location of the transposon in mutant 5G9 corresponds to between positions 573-574 of the *Pasteurella multocida* PM70 genome sequence, Genbank accession number AE006116. The transposon disrupts a homologue of the PM70 gene PM0774 or HyaE. The nucleotide sequence of PM0774 is herein identified as SEQ ID NO: 46 and its amino acid sequence as SEQ ID NO: 47. These genes are involved in the capsule synthesis.

Mutant 6E5

The DNA sequence flanking the transposon insertion site is given in SEQ ID NO: 48 (279 mer). The transposon is immediately at the 3' end of this sequence.

A start codon is located at positions 169-171.

The location of the transposon in mutant 6E5 corresponds to between positions 6673-6674 of the *Pasteurella multocida* PM70 genome, Genbank accession number AE006182. The transposon disrupts a homologue of the PM70 gene PM1459 or pgtB. The nucleotide sequence of PM1459 is herein identified as SEQ ID NO: 49 and its amino acid sequence as SEQ ID NO: 50.

PgtB is a phosphoglycerate transport regulatory protein.

Mutant 6G4

The DNA sequence flanking the transposon insertion site is given in SEQ ID NO: 57 (700 mer). The transposon is immediately at the 5' end of this sequence.

The location of the transposon in mutant 6G4 corresponds to between positions 3758-3759 of the *Pasteurella multocida* PM70 genome sequence, Genbank accession number AE006206. The insertion is between the PM1696 and PM1697 genes. The transposon is inserted between the promoter region and the start codon of PM1696.

The start codon of PM1696 is located at positions 26-28 in the SEQ ID NO: 57 sequence.

The nucleotide sequence of PM1696 is herein identified as SEQ ID NO: 58 and its amino acid sequence as SEQ ID NO: 59.

Other gram negative bacteria genes and proteins were identified by blasts done with SEQ ID NO: 59.

| Strain | Gene (Genbank ref.) | Protein (Genbank ref.) | % of identity |
|---|---|---|---|
| *Haemophilus influenzae* | HI0266 (U32713) | HI0266 (AAC21932) | 87% over 184 amino acids |
| *Salmonella typhi* | STY3386 (AL627278) | STY3386 (CAD07732) | 71% over 185 amino acids |
| *Salmonella typhimurium* | STM3207 (AE008847) | ygiH (AAL22081) | 71% over 185 amino acids |

Mutant 6E6

The DNA sequence flanking the transposon insertion site is given in SEQ ID NO: 51 (93 mer). The transposon is immediately at the 3' end of this sequence.

A stop codon is located at positions 12-14.

The location of the transposon in mutant 6E6 corresponds to between positions 9051-9052 of the *Pasteurella multocida* PM70 genome sequence, Genbank accession number AE006096. The transposon disrupts a homologue of the PM70 gene PM0605. The nucleotide sequence of PM0605 is herein identified as SEQ ID NO: 52 and its amino acid sequence as SEQ ID NO: 53.

Mutant 6F12

The DNA sequence flanking the transposon insertion site is given in SEQ ID NO: 54 (772 mer). The transposon is immediately at the 5' end of this sequence.

A start codon is located at positions 2-4.

The location of the transposon in mutant 6F12 corresponds to between positions 5362-5363 of the *Pasteurella multocida* PM70 genome sequence, Genbank accession number AE006192. The transposon disrupts a homologue of the PM70 gene PM1556 or comF gene. The nucleotide sequence of PM1556 is herein identified as SEQ ID NO: 55 and its amino acid sequence as SEQ ID NO: 56.

ComF is the competence protein F.

Mutant 6H1

The DNA sequence flanking the transposon insertion site is given in SEQ ID NO: 60 (188 mer). The transposon is immediately at the 3' end of this sequence.

The location of the transposon in mutant 6H1 corresponds to between positions 4139-4140 of the *Pasteurella multocida* PM70 genome sequence, Genbank accession number AE006119. The transposon disrupts a homologue of the PM70 gene PM0806 or speF gene. The nucleotide sequence of PM0806 is herein identified as SEQ ID NO: 61 and its amino acid sequence as SEQ ID NO: 62.

Two other Pasteurellaceae and Vibrionaceae genes were identified by blasts done with SEQ ID NO: 62. These genes are *Haemophilus influenzae* speF (Genbank accession numbers U32740 and AAC22248) and *Vibrio cholerae* ornithine decarboxylase (AE004431 and AAF96957). We find an identity of 83% over 719 amino acids between PM0806 and *H. influenzae* speF.

SpeF is an ornithine decarboxylase.

Mutant 6H6

The DNA sequence flanking the transposon insertion site is given in SEQ ID NO: 63 (101 mer). The transposon is immediately at the 3' end of this sequence. This sequence has two open reading frames (+1 and −1) encoding potential longer proteins. The ORF according to the invention is in frame +1.

The location of the transposon in mutant 6H6 corresponds to between positions 983-984 of the *Pasteurella multocida* PM70 genome sequence, Genbank accession number AE006155. The transposon disrupts a homologue of the PM70 gene PM1138. The nucleotide sequence of PM1138 is herein identified as SEQ ID NO: 64 and its amino acid sequence as SEQ ID NO: 65.

Mutant 7A7

The DNA sequence flanking the transposon insertion site is given in SEQ ID NO: 66 (222 mer). The transposon is immediately at the 5' end of this sequence. The location of the transposon in mutant 7A7 corresponds to between positions 7853-7854 of the *Pasteurella multocida* PM70 genome sequence, Genbank accession number AE006170 (in the intergenic region between PM1321 and PM1322). The transposon is inserted between the terminator region and the stop codon of PM1322.

The stop codon is located at positions 25-27 in the SEQ ID NO: 66 sequence. The nucleotide sequence of PM1322 is herein identified as SEQ ID NO: 67 and its amino acid sequence as SEQ ID NO: 68.

Mutant 7F8

The DNA sequence flanking the transposon insertion site is given in SEQ ID NO: 69 (55 mer). The transposon is immediately at the 3' end of this sequence. This sequence has three open reading frames (+1, +3 and −3) encoding potential longer proteins. The ORF according to the invention is in frame +3.

The location of the transposon in mutant 7F8 corresponds to between positions 8292-8293 of the *Pasteurella multocida* PM70 genome sequence, Genbank accession number AE006224. The transposon disrupts a homologue of the PM70 gene PM1866. The nucleotide sequence of PM1866 is herein identified as SEQ ID NO: 70 and its amino acid sequence as SEQ ID NO: 71.

Mutant 9C8

The DNA sequences flanking the both sides of the transposon insertion site are given in SEQ ID NO: 72 (598 mer, transposon at the 5' end) and SEQ ID NO: 73 (561 mer, transposon at the 5' end).

A stop codon is located at positions 26-28 of SEQ ID NO: 72. Sequences SEQ ID NO: 72 and 73 are combined together and limited to the ORF. The resulting sequence is designated SEQ ID NO: 74 (575 mer).

The location of the transposon in mutant 9C8 corresponds to between positions 2224-2225 or 2210-2211 of the *Pasteurella multocida* PM70 genome sequence, Genbank accession number AE006132, positions deduced from SEQ ID NO: 72 and 73 respectively. Both positions are inside the PM0926 (fimA) gene. The nucleotide sequence of PM0926 is herein identified as SEQ ID NO: 75 and its amino acid sequence as SEQ ID NO: 76.

One other Pasteurellaceae gene/protein was identified by blasts done with SEQ ID NO: 76. This is *Haemophilus influenzae* FimA (Genbank accession numbers AF053125 and AAC08991). We find an identity of 77% over 171 amino acids between PM0926 and *H. influenzae* FimA.

FimA is an adhesin, a fimbrial protein.

The 9C8 mutant was deposited under Budapest Treaty in the Pasteur Institute Collection and is available under the accession number CNCM I-3001.

Mutant 9H4

The DNA sequences flanking the both sides of the transposon insertion site are given in SEQ ID NO: 92 (1391 mer). The transposon was inserted at the position 850-851 of this sequence. This sequence has only one reading frame. The ORF according to the invention is in frame −2.

A start codon is located at positions 1318-1316 and a stop codon is located at positions 29-31 of SEQ ID NO: 92. The ORF resulting sequence is designated SEQ ID NO: 93 (1290 mer) and its amino acid sequence is designated SEQ ID NO: 94.

The blasts done with the sequences SEQ ID NO: 92 and SEQ ID NO: 94 did not identify any homologous genes or proteins.

The 9H4 mutant was deposited under Budapest Treaty in the Pasteur Institute Collection and is available under the accession number CNCM I-3002.

Mutant 10G11

The DNA sequence flanking the transposon insertion site is given in SEQ ID NO: 77 (70 mer). The transposon is immediately at the 5' end of this sequence. A start codon is located at positions 62-64.

The location of the transposon in mutant 10G11 corresponds to between positions 2938-2939 of the *Pasteurella multocida* PM70 genome sequence, Genbank accession number AE006056. The transposon disrupts a homologue of the PM70 gene PM0220 (rpL31_1). The nucleotide sequence of PM0220 is herein identified as SEQ ID NO: 78 and its amino acid sequence as SEQ ID NO: 79.

RpL31_1 is a 50S ribosomal protein.

Mutant 11E8

The DNA sequence flanking the transposon insertion site is given in SEQ ID NO: 80 (506 mer). The transposon is immediately at the 5' end of this sequence.

A start codon is located at positions 195-197 of SEQ ID NO: 80.

The location of the transposon in mutant 11E8 corresponds to between positions 282-283 of the *Pasteurella multocida* PM70 genome sequence, Genbank accession number AE006085. The transposon disrupts a homologue of the PM70 gene PM0488. The nucleotide sequence of PM0488 is herein identified as SEQ ID NO: 81 and its amino acid sequence as SEQ ID NO: 82.

Mutant 12A1

The DNA sequence flanking the transposon insertion site is given in SEQ ID NO: 83 (243 mer). The transposon is immediately at the 3' end of this sequence.

One other Pasteurellaceae gene was identified by blasts done with SEQ ID NO: 83 and its encoded amino acid sequence (81 amino acids). We find an identity of 100% over 81 amino acids with PM0063 protein. The location of the transposon in mutant 12A1 corresponds to between positions 2880-2881 of the *Pasteurella multocida* PM70 genome sequence, Genbank accession number AE006042. The transposon disrupts a homologue of the PM70 gene PM0063 or lepA gene. The nucleotide sequence of PM0063 is herein identified as SEQ ID NO: 84 and its amino acid sequence as SEQ ID NO: 85.

Other gram negative bacteria genes and proteins were identified by blasts done with SEQ ID NO: 85.

| Strain | Gene (Genbank ref.) | Protein (Genbank ref.) | % of identity |
|---|---|---|---|
| *Haemophilus influenzae* | HI0016 (U32687) | LepA (AAC21694) | 95% over 598 amino acids |
| *Yersinia pestis* | YPO2716 (AJ414153) | LepA (CAC92955) | 88% over 597 amino acids |
| *Escherichia coli* K12 | LepA (AE000343) | LepA (AAC75622) | 89% over 597 amino acids |
| *Salmonella typhi* | STY2829 (AL627275) | LepA (CAD02785) | 89% over 597 amino acids |
| *Salmonella typhimurium* | LepA (AE008817) | LepA (AAL21477) | 89% over 597 amino acids |
| *Vibrio cholerae* | VC2463 (AE004316) | LepA (AAF95605) | 84% over 597 amino acids |
| *Pseudomonas aeruginosa* | PA0767 (AE004511) | LepA (AAG04156) | 75% over 594 amino acids |

LepA is a GTP-binding membrane protein.

Mutant 12B3

The DNA sequence flanking the transposon insertion site is given in SEQ ID NO: 86 (147 mer). The transposon is immediately at the 3' end of this sequence.

The location of the transposon in mutant 12B3 corresponds to between positions 4028-4029 of the *Pasteurella multocida* PM70 genome sequence, Genbank accession number AE006152. The transposon disrupts a homologue of the PM70 gene PM1112 or deaD gene. The nucleotide sequence of PM1112 is herein identified as SEQ ID NO: 87 and its amino acid sequence as SEQ ID NO: 88.

One other Pasteurellaceae gene/protein was identified by blasts done with SEQ ID NO: 88. This is *Haemophilus influenzae* HI0231 (Genbank accession numbers U32709 and AAC21900). We find an identity of 80% over 605 amino acids between PM1112 and HI0231.

DeaD is an RNA helicase.

Mutant 13E1

The DNA sequence flanking the transposon insertion site is given in SEQ ID NO: 89 (187 mer). The transposon is immediately at the 3' end of this sequence. This sequence has two open reading frames (+1 and −3) encoding potential longer proteins. The ORF according to the invention is in frame −3.

The location of the transposon in mutant 13E1 corresponds to between positions 2173-2174 of the *Pasteurella multocida* PM70 genome sequence, Genbank accession number AE006138 (PM0989). The nucleotide sequence of PM0989 is herein identified as SEQ ID NO: 90 and its amino acid sequence as SEQ ID NO: 91.

One other Pasteurellaceae gene/protein was identified by blasts done with SEQ ID NO: 91. This is *Haemophilus influenzae* HI0325 (Genbank accession numbers U32717 and AAC21988). We find an identity of 79% over 414 amino acids between PM0989 and HI0325.

The 13E1 mutant was deposited under Budapest Treaty in the Pasteur Institute Collection and is available under the accession number CNCM I-3003.

Example 5

PCR Selection of Transposon Insertion Mutants

The transposon may insert everywhere in the genome of the bacteria. But a selection of the right mutants can be done using PCR.

A pair of primers are used, one specific for the transposon, such as Tn10IR1 (SEQ ID NO: 101), Tn10IR4 (SEQ ID NO: 102), KTGRI (SEQ ID NO: 100), StipA (SEQ ID NO: 99) and StipJ (SEQ ID NO: 98), and one specific for the gene or sequence to be mutated. The nucleotide sequence of this gene or a part thereof (e.g. sequences of the region near the locus of insertion of the transposon as sequenced above) is helpful to the design of such primers. This can be adapted to genes or nucleotide sequences of other strains of *Pasteurella multocida*, or other gram negative bacteria, such as bacteria of the Pasteurellaceae family, notably *Pasteurella haemolytica*, *Pasteurella anatipestifer* and *Actinobacillus pleuropneumoniae*.

The knowledge of the corresponding gene or ORF and/or their regulatory regions in the *Pasteurella multocida* strain PM70 or P-1059 (Example 4) such as its size is used to screen the amplified PCR fragments and to detect those having a size corresponding to a transposon inserted in the gene or sequence to be mutated. If the transposon was inserted outside the gene, it may have no amplified PCR fragment or it may amplify fragments with a size too long. Thus PCR allows for the selection of the mutants.

For *Pasteurella multocida* P-1059 strain, such gene-specific primers may be:

| Mutant | Primer name | Primer sequence | SED ID NO: |
|---|---|---|---|
| 13E1 | 13E1C | 5' TACGTTAACGCCACCCGTTG | 106 (20 mer) |
| 3A2 | 3° 2C | 5' GCTTCCATACCTTGTGAACC | 107 (20 mer) |
| 2F2 | 2F2C | 5' GGGTGTACGCCTTCTGCTG | 108 (19 mer) |
| 9C8 | 9C8C | 5' ATTGCAGTCATTGCGGATGC | 109 (20 mer) |
| 12A1 | 12A1C | 5' CGATATGGTACGTGTCGAC | 110 (19 mer) |
| 5F11 | 5F11C | 5' AAAAGGCGGACCTAAGTCCG | 111 (20 mer) |
| 5D5 | 5D5C | 5' CCGACAACATGACAATGGAG | 112 (20 mer) |
| 4G11 | 4G11C | 5' TTTGCAGTGGCTTACCGTC | 113 (19 mer) |
| 12B3 | 12B3C | 5' CCTGACGACCAATACGGTG | 114 (19 mer) |
| 5G9 | 5G9C | 5' GGATGGTCTGATCCTAATGC | 115 (20 mer) |
| 9H4 | 9H4C | 5' CGTTCATCAGATGACACTGC | 116 (20 mer) |
| 3H2 | 3H2C | 5' GTGATTACGGGATTATCGGG | 117 (20 mer) |
| 10G11 | 10G11C | 5' TGAAGTGGTAACGAGGCTTG | 118 (20 mer) |

In the case of the mutants obtained previously, the PCR was be carried out with the following pairs of primers and the amplified PCR fragments had a size of:

| Gene-specific Primer | Transposon-specific Primer | PCR size (bp) |
|---|---|---|
| 13E1C | Tn10IR4 | 250 |
| 13E1C | StipA | 320 |
| 13E1C | StipJ | 1720 |
| 3A2C | KTGRI | 510 |
| 2F2C | Tn10IR1 | 105 |
| 2F2C | StipJ | 1710 |
| 9C8C | Tn10IR4 | 500 |
| 12A1C | Tn10IR4 | 310 |
| 5F11C | Tn10IR4 | 560 |
| 5D5C | StipJ | 1705 |
| 4G11C | StipJ | 1680 |
| 12B3C | StipJ | 1720 |
| 5G9C | StipJ | 1660 |
| 9H4C | Tn10IR4 | 585 |

-continued

| Gene-specific Primer | Transposon-specific Primer | PCR size (bp) |
|---|---|---|
| 3H2C | StipJ | 1690 |
| 10G11C | Tn10IR4 | 395 |

Example 6

Efficacy and Protection of Transposon Insertion Mutants Against Homologous Challenge The transposon insertion mutants derived from *Pasteurella multocida* 16084 strain (Example 1) were administered by eye-drop to three week-old conventional turkeys. Efficacy was studied against an ocular homologous challenge with *Pasteurella multocida* 16084 strain.

24 groups of conventional turkeys aged 3 weeks were set up. On D0, the groups were inoculated by eye drop with about $10^8$ CFU of the mutants as indicated in the following table.

A group of conventional turkeys aged 3 weeks remained unvaccinated and served as controls (Group25).

All the turkeys were challenged on D23 using *Pasteurella multocida* 16084 strain administered by eye drop at $10^8$ CFU per bird.

Mortality was daily recorded for 2 weeks after challenge. At the end of the study (D37), a clinical examination was carried out to determine the health status of the surviving birds.

The protection rate was calculated considering the number of challenged birds and the number of healthy birds on D37.

| Group | Mutant | Number of birds | Protection rate |
|---|---|---|---|
| Group 1 | 1G4 | 8 | 25% |
| Group 2 | 4F4 | 10 | 40% |
| Group 3 | 3A2 | 6 | 67% |
| Group 4 | 1G8 | 10 | 50% |
| Group 5 | 13E1 | 22 | 82% |
| Group 6 | 5D5 | 22 | 68% |
| Group 7 | 7F8 | 10 | 40% |
| Group 8 | 11E8 | 10 | 20% |
| Group 9 | 9C8 | 22 | 82% |
| Group 10 | 4G11 | 20 | 100% |
| Group 11 | 12B3 | 6 | 100% |
| Group 12 | 10G11 | 10 | 20% |
| Group 13 | 5G9 | 8 | 63% |
| Group 14 | 12A1 | 10 | 50% |
| Group 15 | 2F2 | 10 | 20% |
| Group 16 | 5F11 | 10 | 30% |
| Group 17 | 9H4 | 7 | 100% |
| Group 18 | 3H2 | 10 | 40% |
| Group 19 | Control | 41 | 7% |

For some groups, these experiments have been reproduced and the protection rate is cumulative result. Some mutants of the invention were not tested in these experiments.

Example 7

Efficacy and Protection of Transposon Insertion Mutants Against Heterologous Challenge The transposon insertion mutants derived from *Pasteurella multocida* 16084 strain (Example 1) were administered by eye-drop to three week-old conventional turkeys. Efficacy was studied against an ocular heterologous challenge with *Pasteurella multocida* X73 strain (USDA).

Five groups of 10 conventional turkeys aged 3 weeks were set up. On D0, the groups were inoculated by eye drop with about $10^8$ CFU of the mutants as indicated in the following table.

A group of 10 conventional turkeys aged 3 weeks remained unvaccinated and served as controls (Group6).

All the turkeys were challenged on D21 using *Pasteurella multocida* X73 strain administered by eye drop at $10^6$ CFU per bird.

Mortality was daily recorded for 2 weeks after challenge. At the end of the study (D36), a clinical examination was carried out to determine the health status of the surviving birds.

The protection rate was calculated considering the number of challenged birds and the number of healthy birds on D36.

| Group | Mutant | Number of birds | Protection rate |
|---|---|---|---|
| Group 1 | 13E1 | 10 | 70% |
| Group 2 | 5D5 | 10 | 80% |
| Group 3 | 9C8 | 10 | 100% |
| Group 4 | 4G11 | 10 | 100% |
| Group 5 | 9H4 | 10 | 50% |
| Group 6 | Control | 10 | 20% |

Example 8

Construction of Defined Deletion Mutants by Conjugation

Initially, the targeted gene plus flanking DNA sequences are amplified by PCR using high fidelity polymerase and cloned into a suitable cloning vector. PCR primers are designed which delete the gene when used in inverse PCR to generate an initial construct. The PCR primers contain an XbaI site to introduce a new restriction site and thus provide a marker for the gene deletion. The deletion constructs are then transferred into a suicide vector pCVD442 (Donnenberg et. al., Infection and Immunity, 1991, 59: 4310-4317) for transfer to the *Pasteurella* chromosome. The pCVD442 plasmids are then transformed into the *E. coli* strain SM10λpir. This construct is introduced into the 16084 (CDM) *P. multocida* strain by conjugation with *E. coli* SM10λpir/pCVD442. Transformants and recombinants containing the plasmid integrated into the chromosome at the homologous site (merodiploids) are selected using the antibiotic resistance marker present on the pCVD442 plasmid (ampicillin resistance gene). *Pasteurella* mutants are selected on BHI agar plates supplemented with 1 μg/ml ampicillin.

The pCVD442 plasmid requires the Pir protein for replication. This protein is encoded by the pir gene, which is present as a lambda phage lysogen in the donor strain SM10λpir, but not in the recipient *P. multocida*. So the pCVD442 plasmid does not replicate in the recipient *P. multocida* strain: antibiotic resistant colonies are therefore only obtained if the plasmid integrates into the chromosome. This suicide vector also contains the sacB gene that encodes the enzyme levan sucrase, which is toxic to most Gram negative bacteria in the presence of sucrose. Sucrose selection can therefore be employed as a counter selection to isolate colonies in which a second recombination event has occurred, resulting in loss of the plasmid from the chromosome. This second recombination event can result in two outcomes, regeneration of the wild type allele or generation of a deletion mutant. Colonies containing the deletion mutation are identified by colony PCR.

Example 9

Construction of Defined Deletion Mutants by Electroporation

Initially, the targeted gene plus flanking DNA sequences are amplified by PCR using high fidelity polymerase and cloned into a suitable cloning vector. PCR primers are designed which delete the gene when used in inverse PCR to generate an initial construct. The PCR primers contain an XbaI site to introduce a new restriction site and thus provide a marker for the gene deletion. The deletion constructs are then transferred to a suicide vector pCVD442 for transfer to the *Pasteurella* chromosome. This construct is introduced into the 16084 (CDM) *P. multocida* strain by electroporation. To remove the substantial extracellular capsule of 16084, the stationary phase cells are treated with ovine testicular hyaluronidase (type V, filter sterilized before use, final concentration 25 μg/ml) for 1 hour before harvesting and washing the cells. The pCVD442 (1.5 μg) is mixed with cell suspension in 10% glycerol (0.05 ml, $10^{10}$ cell/ml) just prior to pipetting the mixture into the ice-cold 1-mm electroporation cuvettes (Biorad, Hercules, CA, USA). The GenePulser (Biorad) is used to pulse the cells (12.5 kV/cm, 250 ohms, 40 μF). Immediately after the pulse, the cells are diluted with 1 ml BHI and portions of culture (5-50 μl) are quickly (within 1-5 min) spread onto BHI agar plates containing 1 μg/ml ampicillin. Recombinants containing the plasmid integrated into the chromosome at the homologous site (merodiploids) are selected using the antibiotic resistance marker present on the plasmid (ampicillin resistance gene).

The pCVD442 plasmid does not replicate in the recipient *P. multocida* strain: antibiotic resistant colonies are therefore only obtained if the plasmid integrates into the chromosome. This suicide vector also contains the sacB gene that encodes the enzyme levan sucrase, which is toxic to most gram negative bacteria in the presence of sucrose. Sucrose selection can therefore be employed as a counter selection to isolate colonies where a second recombination event has occurred, resulting in loss of the plasmid from the chromosome. This second recombination event can result in two outcomes, regeneration of the wild type allele or generation of a deletion mutant.

Colonies appear after incubation at 37° C. for 2-4 days. Streaking out colonies onto similar plates isolates individual transformants. Colonies containing the deletion mutation are identified by colony PCR.

Example 10

Vaccine and Test of Efficacy

The attenuated deletion mutants obtained in Example 8 or 9 are cultured in CDM culture medium (Hu et. al., Infection and Immunity 1986, 804-810) under shaking condition for 24 to 48 hours.

The culture is harvested when the growth stops, which is followed by optical density (OD) or pH measurement.

The bacterial concentration is determined by optical density and when needed the concentration is adjusted to a final concentration of $10^9$ CFU per ml with fresh culture medium.

The efficacy of the vaccine is tested in 3 week-old turkeys by vaccination and challenge.

The turkeys are checked prior to vaccination for the absence of *Pasteurella* antibodies by ELISA of blood samples.

A first group of turkeys is vaccinated by injection of $10^8$ CFU in 0.1 ml via ocular route.

A second group remained unvaccinated (control group).

All animals are challenged on D21 or D23 with *P. multocida* P-1059 strain by ocular route ($10^8$ CFU in 0.1 ml per animal).

The mortality is observed every day until D35.

A lower mortality is observed in the vaccinated animals compared to the controls.

The invention is further described by the following paragraphs:

1—A mutant of a gram negative bacterium, wherein said bacterium has a mutation in a nucleotide sequence which codes for a polypeptide having an identity which is equal or more than 70%, 75%, 80%, 85%, 90%, 95%, 96%, 97%, 98%, or 99% with an amino acid sequence coded by a nucleotide sequence selected from the group consisting of nucleotide sequences identified SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93 said mutation resulting in attenuated virulence of the bacterium.

2—The mutant of paragraph 1, wherein the bacterium is a Pasteurellaceae.

3—The mutant of paragraph 2, wherein the bacterium is chosen among the group of: *Pasteurella multocida, Pasteurella haemolytica, Pasteurella anatipestifer* and *Actinobacillus pleuropneumoniae.*

4—The mutant of paragraph 3, wherein the bacterium is *Pasteurella multocida.*

5—The mutant of any one of paragraphs 1 to 4, wherein the mutation is a deletion in the nucleotide sequence, or an insertion into it or replacement of nucleic acids.

6—The mutant of paragraph 5, wherein the mutation is the deletion of the whole nucleotide sequence.

7—The mutant of paragraph 5, wherein the insertion is done between: nucleotides 180-181 or 182-183 or 190-191 in SEQ ID NO: 2, 77-78 or 1026-1027 or 1027-1028 in SEQ ID NO: 6, 416-417 in SEQ ID NO: 9, 389-390 in SEQ ID NO: 12, 381-382 in SEQ ID NO: 16, 219-220 in SEQ ID NO: 19, 1353-1354 in SEQ ID NO: 22, 136-137 in SEQ ID NO: 25, 384-385 in SEQ ID NO: 28, 222-223 or 225-226 in SEQ ID NO: 31, 217-218 in SEQ ID NO: 34, 1411-1412 in SEQ ID NO: 37, 943-944 in SEQ ID NO: 40, 855-856 in SEQ ID NO: 43, 369-370 in SEQ ID NO: 46, 111-112 in SEQ ID NO: 49, 443-444 in SEQ ID NO: 52, 4-5 in SEQ ID NO: 55, immediately upstream nucleotide 1 in SEQ ID NO: 58, 573-574 in SEQ ID NO: 61, 875-876 in SEQ ID NO: 64, immediately upstream nucleotide 1 in SEQ ID NO: 67, 218-219 in SEQ ID NO: 70, 1072-1087 in SEQ ID NO: 75, 64-65 in SEQ ID NO: 78, 282-283 in SEQ ID NO: 81, 1431-1432 in SEQ ID NO: 84, 974-975 in SEQ ID NO: 87, 802-803 in SEQ ID NO: 90, 850-851 in SEQ ID NO: 92.

8—The mutant of any one of paragraphs 1 to 7, which comprises an heterologous nucleic acid sequence coding for an immunogen from a pathogenic viral, parasitic or bacterial agent, for a therapeutic protein, for an allergen, for a growth factor or for a cytokine.

9—An immunogenic composition comprising an attenuated mutant according to any one of paragraphs 1 to 8, and a pharmaceutically acceptable diluent, carrier, vehicle or excipient.

10—The immunogenic composition of paragraph 9 comprising further an adjuvant.

11—A vaccine comprising an attenuated mutant according to any one of paragraphs 1 to 8, and a pharmaceutically acceptable diluent, carrier, vehicle or excipient.

12—The vaccine of paragraph 11 comprising further an adjuvant.

13—An immunogenic composition comprising a polypeptide having an identity which is equal or more than 70%, 75%, 80%, 85%, 90%, 95%, 96%, 97%, 98%, or 99% with an amino acid sequence coded by a nucleotide sequence selected from the group consisting of nucleotide sequences identified SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93 and a pharmaceutically acceptable diluent, carrier, vehicle or excipient, and optionally an adjuvant.

14—An antibody preparation comprising an antibody specific to a polypeptide having an identity which is equal or more than 70%, 75%, 80%, 85%, 90%, 95%, 96%, 97%, 98%, or 99% with an amino acid sequence coded by a nucleotide sequence selected from the group consisting of nucleotide sequences identified SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93.

15—Diagnostic method for detecting infection by a gram negative bacterium, using a polypeptide having an identity which is equal or more than 70%, 75%, 80%, 85%, 90%, 95%, 96%, 97%, 98%, or 99% with an amino acid sequence coded by a nucleotide sequence selected from the group consisting of nucleotide sequences identified SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93, or an antibody specific to said polypeptide.

16—Use of an antibody preparation according to paragraph 14 for the production of a passive immunization composition or a therapeutic composition against gram negative bacteria.

17—Use of a nucleotide sequence selected from the group consisting of nucleotide sequences identified SEQ ID NO: 2, 6, 9, 12, 16, 19, 22, 25, 28, 31, 34, 37, 40, 43, 46, 49, 52, 55, 58, 61, 64, 67, 70, 75, 78, 81, 84, 87, 90, 93, or a fragment of at least 20 nucleotides, as primers for PCR for detection of gram negative bacteria in a media.

Having thus described in detail preferred embodiments of the present invention, it is to be understood that the invention defined by the above paragraphs is not to

-continued

<223> OTHER INFORMATION: a, t, c, g, other or unknown
<220> FEATURE:
<221> NAME/KEY: modified_base
<222> LOCATION: (722)
<223> OTHER INFORMATION: a, t, c, g, other or unknown
<220> FEATURE:
<221> NAME/KEY: modified_base
<222> LOCATION: (743)..(745)
<223> OTHER INFORMATION: a, t, c, g, other or unknown
<220> FEATURE:
<221> NAME/KEY: modified_base
<222> LOCATION: (747)..(750)
<223> OTHER INFORMATION: a, t, c, g, other or unknown
<220> FEATURE:
<221> NAME/KEY: modified_base
<222> LOCATION: (756)..(757)
<223> OTHER INFORMATION: a, t, c, g, other or unknown
<220> FEATURE:
<221> NAME/KEY: modified_base
<222> LOCATION: (767)..(768)
<223> OTHER INFORMATION: a, t, c, g, other or unknown

<400> SEQUENCE: 1
gtgctttata tccccattct aaaatacatg ttctctcctt tttccatgtg acaaatggag 60
agaacatttt caagcgttgg gtaaaaaagc cgcttaaata aggaattttt aacatccctt 120
tagaaaaaat aagaaactct tgatacatat ttaatctaat atagtcatat aaagttgaca 180
tatcatatat taaacatgac tagttaatca ttaaatatta aacaacctca acttaataaa 240
acaaataata aacaaacaag gtaaaaaaca aactaatact gagcaaataa aaaacggatt 300
aatataataa cgatatatca acctctaaaa cagaccaaaa ataaatcaca cgagacaaaa 360
gaacaattat aatccaaata ttaattaata aataaacacc tagcgcaacg aataatcaaa 420
caaaatcaca tttagattta tttaaattaa aaatatagat tatattttaa atataatgct 480
agaattcggc accaaaattt ttctccagct gtaaattaga gataaagata tgaaaaaggt 540
tattatcatg ggacataaac agtctaacta tcaagatgtn gaaaaggttt ttcaatgtna 600
tgggatgaat ccccgcntcc atcaaaacgt gaaaaangtc cccatcgaac ttttgctgag 660
tgaggatnag atagggcaaa tctgcaaatt catccacngc cgncgcngac tcatnnanng 720
cnaatcgcca tagtagttat acnnncnnnn gtttanngtt gaccgcnnag gcgag 775

<210> SEQ ID NO 2
<211> LENGTH: 2091
<212> TYPE: DNA
<213> ORGANISM: Pasteurella multocida

<400> SEQUENCE: 2
atgtcaattt tatatgacta tattagatta aatatgtatc aagagtttct tattttttct 60
aaagggatgt taaaaattcc ttatttaagc ggttttttta cccaacgctt gaaaatgttc 120
tctccatttg tcacatggaa aaaggagaga acatgtattt tagaatgggg atataaagca 180
tcatcaaaga aagcgaggca ttttgcacaa caacatgatt taccttatgc gacgatagaa 240
gatggttttt tacgttctat tggactgggt gtggatgggt atccaccttt ctcattagtg 300
tacgatgata ttggtattta ttatgatatc aatcagcctt ctcgtttaga aaacttaatt 360
ctttctcaag atgtattact tcaggaaaaa gtcgatcaag ttgaatatgc aattgaatta 420
atttgtacac ataacctttc caaatataac cacgctattg atacaccttt acagaatacg 480
aagaggccga ttgtcttagt cgttgatcaa acatatggcg atatggcagt tactttcggg 540
aatgccgagc agagtgattt tctacatatg ttagaacgtg cgattattga aaatccaaca 600
gcagaaatct ggttaaaaac ccatcctgat gtaatgtgtg gtaaaaaaca aggctattta 660

-continued

```
acggaatatc agcaatttcc aagagtaaaa gtattatcag aagattttaa ttctatctca    720
ctactaaagc atgttgataa agtttattgc gtgacatctc acactgggtt tgaggccctt    780
ttgttaggaa aaactgtcgt gacttttggg gctgcctggt tttctggttg gggattgacg    840
gatgatcggc atgcgtatat tcgtcagcta aaacagagta agagaagagc gaagcgttca    900
ttgttgcagt tattctatgc tgcttatttc caatattgtc gttatattaa tcctaatacg    960
ggtaaatcag gcacattgtt tgatgtcatt gattatctga ttcaagcaaa aaaagtaacc   1020
aatcagttag ctggtgatat ttattgtgtg ggtatgcgct tttggaaacg taaagtggtt   1080
caaccctttt ttcaatttcc acgctgtcgt ttacattttg tgctgaatgt gcatgagcta   1140
aagcgatgta ttcacgagaa atctcaggct aaaatagtgg tgtggggaca ttcacacatt   1200
gaagtggttg aatatgccaa gcaacagcaa cttcctcttt tgagaatgga agatggtttt   1260
ttacgttcag ttgggttagg gtctaattta acgccaccga tatcattagt tttagatgac   1320
gttggcattt attttgacgc ccaatctcgt tcccgattag aggatattct acagcatcaa   1380
tcctttactc taaaggattt acagcgcgca gaaacgttaa agaaaacact gattgagcaa   1440
catattggta agtataatgt gggacataca cacttatgcc taacacacat cagacaaaat   1500
aaacttttag ttgtgggaca agtggaaaat gatgcttcaa ttcaatatgg ttcaccgcat   1560
attcgtacga atgcagagtt attatgtacg gtcagaaaaa ataatcccca agcctatatt   1620
atttataaac ctcatcctga tgtggttgca ggcaatcgta aaaacacaga tcgtctagat   1680
gattatcgac agtatgctga tttcgtggtt gagaaagcca atatattgga ttgcattaac   1740
caagtggatg aagtgcatac gatgacctct ttagcggggt ttgaagcgtt actgcgcgag   1800
aaaaaagtac attgttatgg cttgcctttt tattctaact gggggctaac agtggatcat   1860
ctttctctaa accgaagaag tcggaagtta agtcttttag aattaattgc tggcgtgctg   1920
atttattacc cacaatatat tgacccaaaa acaaaaacaa tgatcgatgt gcagcgagcg   1980
gttgatattc tgatcgagca acgtcgaaaa ataaaaaata ataaattaca tacaaattat   2040
tttatgaaca tttttatgaa attaaaaaat gtttattctg ttttgaggta g            2091
```

<210> SEQ ID NO 3
<211> LENGTH: 696
<212> TYPE: PRT
<213> ORGANISM: Pasteurella multocida

<400> SEQUENCE: 3

```
Met Ser Ile Leu Tyr Asp Tyr Ile Arg Leu Asn Met Tyr Gln Glu Phe
 1               5                  10                  15

Leu Ile Phe Ser Lys Gly Met Leu Lys Ile Pro Tyr Leu Ser Gly Phe
            20                  25                  30

Phe Thr Gln Arg Leu Lys Met Phe Ser Pro Phe Val Thr Trp Lys Lys
        35                  40                  45

Glu Arg Thr Cys Ile Leu Glu Trp Gly Tyr Lys Ala Ser Ser Lys Lys
    50                  55                  60

Ala Arg His Phe Ala Gln Gln His Asp Leu Pro Tyr Ala Thr Ile Glu
65                  70                  75                  80

Asp Gly Phe Leu Arg Ser Ile Gly Leu Gly Val Asp Gly Tyr Pro Pro
                85                  90                  95

Phe Ser Leu Val Tyr Asp Asp Ile Gly Ile Tyr Tyr Asp Ile Asn Gln
            100                 105                 110

Pro Ser Arg Leu Glu Asn Leu Ile Leu Ser Gln Asp Val Leu Leu Gln
```

-continued

```
            115                 120                 125
Glu Lys Val Asp Gln Val Glu Tyr Ala Ile Glu Leu Ile Cys Thr His
        130                 135                 140
Asn Leu Ser Lys Tyr Asn His Ala Ile Asp Thr Pro Leu Gln Asn Thr
145                 150                 155                 160
Lys Arg Pro Ile Val Leu Val Asp Gln Thr Tyr Gly Asp Met Ala
                165                 170                 175
Val Thr Phe Gly Asn Ala Glu Gln Ser Asp Phe Leu His Met Leu Glu
                180                 185                 190
Arg Ala Ile Ile Glu Asn Pro Thr Ala Glu Ile Trp Leu Lys Thr His
                195                 200                 205
Pro Asp Val Met Cys Gly Lys Lys Gln Gly Tyr Leu Thr Glu Tyr Gln
        210                 215                 220
Gln Phe Pro Arg Val Lys Val Leu Ser Glu Asp Phe Asn Ser Ile Ser
225                 230                 235                 240
Leu Leu Lys His Val Asp Lys Val Tyr Cys Val Thr Ser His Thr Gly
                245                 250                 255
Phe Glu Ala Leu Leu Leu Gly Lys Thr Val Val Thr Phe Gly Ala Ala
                260                 265                 270
Trp Phe Ser Gly Trp Gly Leu Thr Asp Asp Arg His Ala Tyr Ile Arg
        275                 280                 285
Gln Leu Lys Gln Ser Lys Arg Arg Ala Lys Arg Ser Leu Leu Gln Leu
        290                 295                 300
Phe Tyr Ala Ala Tyr Phe Gln Tyr Cys Arg Tyr Ile Asn Pro Asn Thr
305                 310                 315                 320
Gly Lys Ser Gly Thr Leu Phe Asp Val Ile Asp Tyr Leu Ile Gln Ala
                325                 330                 335
Lys Lys Val Thr Asn Gln Leu Ala Gly Asp Ile Tyr Cys Val Gly Met
                340                 345                 350
Arg Phe Trp Lys Arg Lys Val Val Gln Pro Phe Phe Gln Phe Pro Arg
        355                 360                 365
Cys Arg Leu His Phe Val Leu Asn Val His Glu Leu Lys Arg Cys Ile
        370                 375                 380
His Glu Lys Ser Gln Ala Lys Ile Val Val Trp Gly His Ser His Ile
385                 390                 395                 400
Glu Val Val Glu Tyr Ala Lys Gln Gln Gln Leu Pro Leu Leu Arg Met
                405                 410                 415
Glu Asp Gly Phe Leu Arg Ser Val Gly Leu Gly Ser Asn Leu Thr Pro
        420                 425                 430
Pro Ile Ser Leu Val Leu Asp Asp Val Gly Ile Tyr Phe Asp Ala Gln
        435                 440                 445
Ser Arg Ser Arg Leu Glu Asp Ile Leu Gln His Gln Ser Phe Thr Leu
        450                 455                 460
Lys Asp Leu Gln Arg Ala Glu Thr Leu Lys Lys Thr Leu Ile Glu Gln
465                 470                 475                 480
His Ile Gly Lys Tyr Asn Val Gly His Thr His Leu Cys Leu Thr His
                485                 490                 495
Ile Arg Gln Asn Lys Leu Leu Val Val Gly Gln Val Glu Asn Asp Ala
                500                 505                 510
Ser Ile Gln Tyr Gly Ser Pro His Ile Arg Thr Asn Ala Glu Leu Leu
        515                 520                 525
Cys Thr Val Arg Lys Asn Asn Pro Gln Ala Tyr Ile Ile Tyr Lys Pro
        530                 535                 540
```

-continued

```
His Pro Asp Val Val Ala Gly Asn Arg Lys Asn Thr Asp Arg Leu Asp
545                 550                 555                 560

Asp Tyr Arg Gln Tyr Ala Asp Phe Val Val Glu Lys Ala Asn Ile Leu
                565                 570                 575

Asp Cys Ile Asn Gln Val Asp Glu Val His Thr Met Thr Ser Leu Ala
            580                 585                 590

Gly Phe Glu Ala Leu Leu Arg Glu Lys Lys Val His Cys Tyr Gly Leu
        595                 600                 605

Pro Phe Tyr Ser Asn Trp Gly Leu Thr Val Asp His Leu Ser Leu Asn
    610                 615                 620

Arg Arg Ser Arg Lys Leu Ser Leu Leu Glu Leu Ile Ala Gly Val Leu
625                 630                 635                 640

Ile Tyr Tyr Pro Gln Tyr Ile Asp Pro Lys Thr Lys Thr Met Ile Asp
                645                 650                 655

Val Gln Arg Ala Val Asp Ile Leu Ile Glu Gln Arg Arg Lys Ile Lys
            660                 665                 670

Asn Asn Lys Leu His Thr Asn Tyr Phe Met Asn Ile Phe Met Lys Leu
        675                 680                 685

Lys Asn Val Tyr Ser Val Leu Arg
    690                 695

<210> SEQ ID NO 4
<211> LENGTH: 226
<212> TYPE: DNA
<213> ORGANISM: Pasteurella multocida

<400> SEQUENCE: 4
agcaaaagtt cgattactac cagagacagt aagaagtgcg gttaaaatac ctaacaagaa     60
gagaaataac acaatattaa tgttatttga attaagtgcg ttatcactgt atgccaatga    120
aataatatta tttttgagat acattagcgt atgcgaaata ttaaaatctg caagcattaa    180
agcacctaca ataataccaa cactcaatga taaaataaca cggcgc                   226

<210> SEQ ID NO 5
<211> LENGTH: 87
<212> TYPE: DNA
<213> ORGANISM: Pasteurella multocida

<400> SEQUENCE: 5
cgacactatg cattcttatt gatcgtcaag tgagtttggc ggaatacggt aaatcctgga     60
ttttaggcgt gaagtcaatg ctcggtg                                          87

<210> SEQ ID NO 6
<211> LENGTH: 1524
<212> TYPE: DNA
<213> ORGANISM: Pasteurella multocida

<400> SEQUENCE: 6
atggaactta ttgattattc gacgtctatt tggtctgtcg tacccctat tttagcatta     60 ttattagcca ttgggacacg ccgtgttatt ttatcattga gtgttggtat tattgtaggc    120
gctttaatgc ttgcagattt taatatttcg catacgctaa tgtatctcaa aaataatatt    180
atttcattgg catacagtga taacacactt aattcaaata acattaatat tgtgttattt    240
ctcttcttgt taggtatttt aaccgcactt cttactgtct caggcagtaa tcgagccttt    300
gcagaatggg cacaaaaacg aattaaagat agaaaagggg ctaaattatt agccgcatcg    360
ctcgtgtttg tgactttcat tgacgattat tttcatagct tagcggtggg agcgattgcc    420
agcccagtta cagataaatt taaagtttca cgcccaaaac ttgcctatat tcttgattca    480
accgctgcgc caatgtgtgt gttgatgcct gtatcaagtt ggggcgccta tattattaca    540
```

-continued

```
cttattgcag gacttcttgc gacttattcg atcaccgagt attcccctat cggtgcattt      600
atgacaatga gtgcaatgaa cttttatgct attttttcta ttttaatggt gttctttgta      660
tcttattatt cgtttgatat tggttcaatg gcgcgtcacg aaagaatggc cctagcgcgt      720
gtaacagaag aagaaaaact ggaaagtagt aataaagggc atgttctcta tttaatttta      780
ccgattactg tcctgatttt agcaaccgtt ggtatgatga tgtacacggg ctatgaagca      840
ttagcggcgg atggaaaacc ttttgatgtg ttaggcgcgt ttgagaatac tacagtaggg      900
atttcattgg ttgtgggggg attaagtgcg gtcttgattt cgacactatg cattcttatt      960
gatcgtcaag tgagtttggc tgaatacggt aaatcctgga ttttaggcgt gaagtcaatg     1020
ctcggtgcgg tattgatttt attgtttgct tggactatta ataccatcgt tggagatgtc     1080
aaaacaggga tttattttatc ttcattagta tcggatagtt taccgattgc tttgttgcct     1140
gcgttattat ttattttaac tggaatcatg gcattctcga caggaacaag ctggggaact     1200
tttgggatta tgttaccgat cgcggcagcg attgcagcga atactgcacc agaattgatg     1260
ttaccttgtt tatccgcagt catggctggt gcagtttgtg gtgatcattg ctcaccgatt     1320
tcggatacca cgattttatc ttctaccggg gcaaaatgta atcatatcga ccatgtaaca     1380
acacagttac cttatgcgat gttaattgcg acagcgtcta ttgctggcta tttagtacta     1440
gggttcagcc agtcaggcat actgggtttt gtgacaacgg tgtggttttt atcagtactt     1500
gtttttatat ttagaaaaaa ataa                                            1524
```

<210> SEQ ID NO 7
<211> LENGTH: 507
<212> TYPE: PRT
<213> ORGANISM: Pasteurella multocida

<400> SEQUENCE: 7

```
Met Glu Leu Ile Asp Tyr Ser Thr Ser Ile Trp Ser Val Val Pro Pro
  1               5                  10                  15

Ile Leu Ala Leu Leu Ala Ile Gly Thr Arg Arg Val Ile Leu Ser
             20                  25                  30

Leu Ser Val Gly Ile Ile Val Gly Ala Leu Met Leu Ala Asp Phe Asn
         35                  40                  45

Ile Ser His Thr Leu Met Tyr Leu Lys Asn Asn Ile Ile Ser Leu Ala
     50                  55                  60

Tyr Ser Asp Asn Thr Leu Asn Ser Asn Asn Ile Asn Ile Val Leu Phe
 65                  70                  75                  80

Leu Phe Leu Leu Gly Ile Leu Thr Ala Leu Leu Thr Val Ser Gly Ser
                 85                  90                  95

Asn Arg Ala Phe Ala Glu Trp Ala Gln Lys Arg Ile Lys Asp Arg Lys
            100                 105                 110

Gly Ala Lys Leu Leu Ala Ala Ser Leu Val Phe Val Thr Phe Ile Asp
        115                 120                 125

Asp Tyr Phe His Ser Leu Ala Val Gly Ala Ile Ala Ser Pro Val Thr
    130                 135                 140

Asp Lys Phe Lys Val Ser Arg Pro Lys Leu Ala Tyr Ile Leu Asp Ser
145                 150                 155                 160

Thr Ala Pro Met Cys Val Leu Met Pro Val Ser Ser Trp Gly Ala
                165                 170                 175

Tyr Ile Ile Thr Leu Ile Ala Gly Leu Leu Ala Thr Tyr Ser Ile Thr
            180                 185                 190

Glu Tyr Ser Pro Ile Gly Ala Phe Met Thr Met Ser Ala Met Asn Phe
```

```
                    195                 200                 205
Tyr Ala Ile Phe Ser Ile Leu Met Val Phe Val Ser Tyr Tyr Ser
    210                 215                 220

Phe Asp Ile Gly Ser Met Ala Arg His Glu Arg Met Ala Leu Ala Arg
225                 230                 235                 240

Val Thr Glu Glu Lys Leu Glu Ser Ser Asn Lys Gly His Val Leu
                245                 250                 255

Tyr Leu Ile Leu Pro Ile Thr Val Leu Ile Leu Ala Thr Val Gly Met
                260                 265                 270

Met Met Tyr Thr Gly Tyr Glu Ala Leu Ala Ala Asp Gly Lys Pro Phe
            275                 280                 285

Asp Val Leu Gly Ala Phe Glu Asn Thr Thr Val Gly Ile Ser Leu Val
    290                 295                 300

Val Gly Gly Leu Ser Ala Val Leu Ile Ser Thr Leu Cys Ile Leu Ile
305                 310                 315                 320

Asp Arg Gln Val Ser Leu Ala Glu Tyr Gly Lys Ser Trp Ile Leu Gly
                325                 330                 335

Val Lys Ser Met Leu Gly Ala Val Leu Ile Leu Leu Phe Ala Trp Thr
            340                 345                 350

Ile Asn Thr Ile Val Gly Asp Val Lys Thr Gly Ile Tyr Leu Ser Ser
        355                 360                 365

Leu Val Ser Asp Ser Leu Pro Ile Ala Leu Leu Pro Ala Leu Leu Phe
    370                 375                 380

Ile Leu Thr Gly Ile Met Ala Phe Ser Thr Gly Thr Ser Trp Gly Thr
385                 390                 395                 400

Phe Gly Ile Met Leu Pro Ile Ala Ala Ile Ala Ala Asn Thr Ala
                405                 410                 415

Pro Glu Leu Met Leu Pro Cys Leu Ser Ala Val Met Ala Gly Ala Val
            420                 425                 430

Cys Gly Asp His Cys Ser Pro Ile Ser Asp Thr Thr Ile Leu Ser Ser
        435                 440                 445

Thr Gly Ala Lys Cys Asn His Ile Asp His Val Thr Thr Gln Leu Pro
    450                 455                 460

Tyr Ala Met Leu Ile Ala Thr Ala Ser Ile Ala Gly Tyr Leu Val Leu
465                 470                 475                 480

Gly Phe Ser Gln Ser Gly Ile Leu Gly Phe Val Thr Thr Gly Val Val
                485                 490                 495

Leu Ser Val Leu Val Phe Ile Phe Arg Lys Lys
            500                 505

<210> SEQ ID NO 8
<211> LENGTH: 78
<212> TYPE: DNA
<213> ORGANISM: Pasteurella multocida

<400> SEQUENCE: 8
gggaaaagca gcaaatatca aaaatactgt tttagtgaaa acaggaaaac cgattacagc    60
agaaggcgta cacccacc                                                 78

<210> SEQ ID NO 9
<211> LENGTH: 555
<212> TYPE: DNA
<213> ORGANISM: Pasteurella multocida

<400> SEQUENCE: 9
```

```
atgaaaaaag caattttttt agatcgagat ggcacattaa atattgatca tggctatgtt      60
catgaaattg atcagtttca atttattgac ggtagcattg aagcgttaca acaactgaaa     120
gcgatgggct atttattggt acttgtaaca aatcagtcag gtattgcgcg tggatatttt     180
agcgaagatc aattttttaca gctgacagaa tggatggatt ggtctcttgc agatcgtgga   240
gtggatttag atggcatcta ttattgccca caccacacag aaggaaaagg tgagtattgc    300
caagactgcg attccgtaa gccaaaacct ggtatgttac tgcaggcaat taaggaactt     360
aatatagatc ccaataccct ctttatggtg ggtgataaag tggaagatat gttagcaggt    420
aaaggtgcca aaattaaaaa tactgtttta gtgaaaacag gcaagcctat tacggaggat    480
ggcaaaaaac aggcaaacta tgtattagag tccattgcgg atctaccaaa actgataaaa    540
ggattaaaaa gttaa                                                       555
```

<210> SEQ ID NO 10
<211> LENGTH: 184
<212> TYPE: PRT
<213> ORGANISM: Pasteurella multocida

<400> SEQUENCE: 10

```
Met Lys Lys Ala Ile Phe Leu Asp Arg Asp Gly Thr Leu Asn Ile Asp
1               5                   10                  15

His Gly Tyr Val His Glu Ile Asp Gln Phe Gln Phe Ile Asp Gly Ser
            20                  25                  30

Ile Glu Ala Leu Gln Gln Leu Lys Ala Met Gly Tyr Leu Leu Val Leu
        35                  40                  45

Val Thr Asn Gln Ser Gly Ile Ala Arg Gly Tyr Phe Ser Glu Asp Gln
    50                  55                  60

Phe Leu Gln Leu Thr Glu Trp Met Asp Trp Ser Leu Ala Asp Arg Gly
65                  70                  75                  80

Val Asp Leu Asp Gly Ile Tyr Tyr Cys Pro His His Thr Glu Gly Lys
                85                  90                  95

Gly Glu Tyr Cys Gln Asp Cys Asp Cys Arg Lys Pro Lys Pro Gly Met
            100                 105                 110

Leu Leu Gln Ala Ile Lys Glu Leu Asn Ile Asp Pro Asn Thr Ser Phe
        115                 120                 125

Met Val Gly Asp Lys Val Glu Asp Met Leu Ala Gly Lys Gly Ala Lys
    130                 135                 140

Ile Lys Asn Thr Val Leu Val Lys Thr Gly Lys Pro Ile Thr Glu Asp
145                 150                 155                 160

Gly Lys Lys Gln Ala Asn Tyr Val Leu Glu Ser Ile Ala Asp Leu Pro
                165                 170                 175

Lys Leu Ile Lys Gly Leu Lys Ser
            180
```

<210> SEQ ID NO 11
<211> LENGTH: 467
<212> TYPE: DNA
<213> ORGANISM: Pasteurella multocida

<400> SEQUENCE: 11

```
gagctctgca tttagtttaa gtggtgattt cttatttgac ttcaataaag attcattaac     60
agcaaaaggt aaagaagttg ttgacagcgt tgcaacacaa ttaaaagcct ctgatgcaaa    120
agaagtgaaa gtcgcaggct ttactgaccg tttaggttca gaagcgtata acttaaaact    180
ttctcaacgt cgtgcagatc gtgttaaagc gcgtttaatt gagcaaggtg ttgccgcaaa   240
```

```
tattcatgct gtaggctatg gtaaagcaca acaagtgaaa gcttgtgatg atgtacaagg      300
tgcagcatta agagactgtt tacgtcctaa ccgtcgtgtt gaaattaccg cttctggtac      360
tgtgttaaaa caaggttcac aaggtatgga agcagggaca acaggaccag caccacttta      420
tagaaaataa ttttctcaa tgaaatagaa gggcgcttta atagcgc                     467
```

<210> SEQ ID NO 12
<211> LENGTH: 819
<212> TYPE: DNA
<213> ORGANISM: Pasteurella multocida

<400> SEQUENCE: 12

```
atgaaattat ctcgcgtttt attaacagtt gttgctgcga cgacattggc tgcctgcggt       60
aatttaagta agttactcc agaaggtaca tctgacaatt tagtgtggcc aaaaattgat      120
gaatcagtct ttaatcatga tggtagccaa tttggttctt ggccaaactg ggataacgta      180
cgcatggttg agcgtggtat gaataaagac caactttata atttgttagg tcgtccacac      240
ttctctgaag gcttatacgg tgtgcgtgaa tgggactatg tgtttaacta tcgtgagaat      300
ggtgtacata agtatgtca atataaagtc ttatttgaca aaaatatgaa tgcacaaagt      360
ttcttctggt atccaaatgg ctgtaacggt agctctgcat ttagtttaag tggtgatttc      420
ttatttgact tcaataaaga ttcattaaca gcaaaaggta agaagttgt tgacagcgtt      480 gcaacacaat taaaagcctc tgatgcaaaa gaagtgaaag tcgcaggctt tactgaccgt      540
ttaggttcag aagcgtataa cttaaaactt tctcaacgtc gtgcagatcg tgttaaagcg      600
cgtttaattg agcaaggtgt tgccgcaaat atccatgctg taggctatgg taaagcacaa      660
caagtgaaag cttgtgatga tgtacaaggt gcagcattaa gagattgttt acgtcctaac      720
cgtcgtgttg aaattaccgc ttctggtact gtgttaaaac aaggttcaca aggtatggaa      780
gcagggacaa caggaccagc accactttat agaaaataa                             819
```

<210> SEQ ID NO 13
<211> LENGTH: 272
<212> TYPE: PRT
<213> ORGANISM: Pasteurella multocida

<400> SEQUENCE: 13

```
Met Lys Leu Ser Arg Val Leu Leu Thr Val Val Ala Ala Thr Thr Leu
1               5                   10                  15

Ala Ala Cys Gly Asn Leu Ser Lys Val Thr Pro Glu Gly Thr Ser Asp
            20                  25                  30

Asn Leu Val Trp Pro Lys Ile Asp Glu Ser Val Phe Asn His Asp Gly
        35                  40                  45

Ser Gln Phe Gly Ser Trp Pro Asn Trp Asp Asn Val Arg Met Val Glu
    50                  55                  60

Arg Gly Met Asn Lys Asp Gln Leu Tyr Asn Leu Leu Gly Arg Pro His
65                  70                  75                  80

Phe Ser Glu Gly Leu Tyr Gly Val Arg Glu Trp Asp Tyr Val Phe Asn
                85                  90                  95

Tyr Arg Glu Asn Gly Val His Lys Val Cys Gln Tyr Lys Val Leu Phe
            100                 105                 110

Asp Lys Asn Met Asn Ala Gln Ser Phe Phe Trp Tyr Pro Asn Gly Cys
        115                 120                 125

Asn Gly Ser Ser Ala Phe Ser Leu Ser Gly Asp Phe Leu Phe Asp Phe
    130                 135                 140
```

```
Asn Lys Asp Ser Leu Thr Ala Lys Gly Lys Glu Val Val Asp Ser Val
145                 150                 155                 160

Ala Thr Gln Leu Lys Ala Ser Asp Ala Lys Glu Val Lys Val Ala Gly
            165                 170                 175

Phe Thr Asp Arg Leu Gly Ser Glu Ala Tyr Asn Leu Lys Leu Ser Gln
        180                 185                 190

Arg Arg Ala Asp Arg Val Lys Ala Arg Leu Ile Glu Gln Gly Val Ala
    195                 200                 205

Ala Asn Ile His Ala Val Gly Tyr Gly Lys Ala Gln Gln Val Lys Ala
    210                 215                 220

Cys Asp Asp Val Gln Gly Ala Ala Leu Arg Asp Cys Leu Arg Pro Asn
225                 230                 235                 240

Arg Arg Val Glu Ile Thr Ala Ser Gly Thr Val Leu Lys Gln Gly Ser
                245                 250                 255

Gln Gly Met Glu Ala Gly Thr Thr Gly Pro Ala Pro Leu Tyr Arg Lys
            260                 265                 270
```

<210> SEQ ID NO 14
<211> LENGTH: 204
<212> TYPE: DNA
<213> ORGANISM: Pasteurella multocida

<400> SEQUENCE: 14

```
tgccaattat agactttgtg tgaatgtacg agtaatcaca tcacgttgtt gttcaggtgt      60
taatgagttg aaacgtacag cgtaacctga acacggatt gttaattgtg ggtattttc      120 tgggttattg accgcatctt ctaaggtttc gcggcgtaat acgttaacgt ttaagtgttg      180
accaccttct actttgactg ttgg                                            204
```

<210> SEQ ID NO 15
<211> LENGTH: 35
<212> TYPE: DNA
<213> ORGANISM: Pasteurella multocida

<400> SEQUENCE: 15

```
aggtgttttt ttaagaggta aatggatgcc aatta                                35
```

<210> SEQ ID NO 16
<211> LENGTH: 384
<212> TYPE: DNA
<213> ORGANISM: Pasteurella multocida

<400> SEQUENCE: 16

```
atgattaaag gtattcaaat tacccaagcg gctaatgaca atttattaaa ctcatttttgg     60 ttattagata gcgaaaaagg tgaagcgcgt tgtttatgtg ctaaaggtga cttcgttgaa     120
gatcaaatcg ttgcagtaag tgaattaggt caaatcgaat atcgcgaatt accagttgat     180
atcgccccaa cagtcaaagt agaaggtggt caacacttaa acgttaacgt attacgccgc     240
gaaaccttag aagatgcggt caataaccca gaaaaatacc cacaattaac aatccgtgtt     300
tcaggttacg ctgtacgttt caactcatta acacctgaac aacaacgtga tgtgattact     360
cgtacattca cacaaagtct ataa                                            384
```

<210> SEQ ID NO 17
<211> LENGTH: 127
<212> TYPE: PRT
<213> ORGANISM: Pasteurella multocida -continued

<400> SEQUENCE: 17

```
Met Ile Lys Gly Ile Gln Ile Thr Gln Ala Ala Asn Asp Asn Leu Leu
1               5                   10                  15

Asn Ser Phe Trp Leu Leu Asp Ser Glu Lys Gly Glu Ala Arg Cys Leu
            20                  25                  30

Cys Ala Lys Gly Asp Phe Val Glu Asp Gln Ile Val Ala Val Ser Glu
        35                  40                  45

Leu Gly Gln Ile Glu Tyr Arg Glu Leu Pro Val Asp Ile Ala Pro Thr
    50                  55                  60

Val Lys Val Glu Gly Gly Gln His Leu Asn Val Asn Val Leu Arg Arg
65                  70                  75                  80

Glu Thr Leu Glu Asp Ala Val Asn Asn Pro Glu Lys Tyr Pro Gln Leu
                85                  90                  95

Thr Ile Arg Val Ser Gly Tyr Ala Val Arg Phe Asn Ser Leu Thr Pro
            100                 105                 110

Glu Gln Gln Arg Asp Val Ile Thr Arg Thr Phe Thr Gln Ser Leu
        115                 120                 125
```

<210> SEQ ID NO 18
<211> LENGTH: 75
<212> TYPE: DNA
<213> ORGANISM: Pasteurella multocida

<400> SEQUENCE: 18

```
acattcttga tgcaataagt cataacgttt tttgagaaac tggagcttat taaagaaaaa     60
gcgtacatgc cctgt                                                      75
```

<210> SEQ ID NO 19
<211> LENGTH: 390
<212> TYPE: DNA
<213> ORGANISM: Pasteurella multocida

<400> SEQUENCE: 19

```
atgacacgga ttaatctcat cgcccccgct gaactttgtg atcaacatct gttagcagaa     60
cacagagaac tgacacgtat tcccaatgct gtggcaaaag ggaaatttag cctcctcggt    120
cagccagaag attataaatt aggtacaggg catgtacgct tttctttaa taagctccag    180 tttctcaaaa aacgttatga cttattgcat caagaatgtc gagctcgagg ttttaatgtg    240
caatatattt ggcccgacaa gttgccggag gacgataacc tctggttaga ctacatccct    300
actgagcatg ccttagccgc caatagagcg cgtattttag aaagaatgcc tgtcaaagcc    360
cgctttacac caagtaaagc tacaacttaa                                     390
```

<210> SEQ ID NO 20
<211> LENGTH: 129
<212> TYPE: PRT
<213> ORGANISM: Pasteurella multocida

<400> SEQUENCE: 20

```
Met Thr Arg Ile Asn Leu Ile Ala Pro Ala Glu Leu Cys Asp Gln His
1               5                   10                  15

Leu Leu Ala Glu His Arg Glu Leu Thr Arg Ile Pro Asn Ala Val Ala
            20                  25                  30

Lys Gly Lys Phe Ser Leu Leu Gly Gln Pro Glu Asp Tyr Lys Leu Gly
        35                  40                  45

Thr Gly His Val Arg Phe Phe Phe Asn Lys Leu Gln Phe Leu Lys Lys
    50                  55                  60
```

-continued

```
Arg Tyr Asp Leu Leu His Gln Glu Cys Arg Ala Arg Gly Phe Asn Val
65                  70                  75                  80

Gln Tyr Ile Trp Pro Asp Lys Leu Pro Glu Asp Asp Asn Leu Trp Leu
                85                  90                  95

Asp Tyr Ile Pro Thr Glu His Ala Leu Ala Ala Asn Arg Ala Arg Ile
            100                 105                 110

Leu Glu Arg Met Pro Val Lys Ala Arg Phe Thr Pro Ser Lys Ala Thr
        115                 120                 125

Thr
```

<210> SEQ ID NO 21
<211> LENGTH: 229
<212> TYPE: DNA
<213> ORGANISM: Pasteurella multocida

<400> SEQUENCE: 21

```
cgatttcaat cccttttggg cggagttgtt catcatcata aatatgttta tcgccgtaga     60
gggcattgat tgtttcatgg ataccaatat agcctaatga aatagaggca cgcccatttt    120
taaagatttg tgccacattg tcatcagcct ttaagcgtac accacaggca ccctccatat    180
aaagaattgg ggcaacgcga gctttggtat gttctaaacg tgcaatgcg                229
```

<210> SEQ ID NO 22
<211> LENGTH: 2142
<212> TYPE: DNA
<213> ORGANISM: Pasteurella multocida

<400> SEQUENCE: 22

```
atggcaactt tctttgtaat taaacgagat gggtcacgaa cggggtttga aatccaacgt     60
atcattaatg caattaaaaa agcggcacaa gcggtgaata ttgaagatga acgttattgt    120
catacaatgg gacagcaggt atgtaatgac atctttactc gttaccaaca agaaattgat    180
atcagccaca ttcaaaaaat cgtagaaaat accttaatgg cgggaaaata ccctgaaata    240
gcgcgagctt atatcgaata ccgccatgat cgggatctcg cgcgagaaaa acgcagtcaa    300
ctcacaaaag aaatcgaagg attaattcag caaagtaatg ttgaactcct caatgaaaat    360
gccaataaag atgcgaaagt tatcccaact caacgcgatc tcttagcggg tattgtggca    420
aaacattacg ctaaacgtta tattctgcca cgcgatgtcg tagacgcaca tgaaaaaggg    480
gaaattcatt atcacgattt agactatgcc ccatttttcc caatgtttaa ctgcatgctt    540
gtcgatctca aagggatgct aagcaatggt ttcaaaatgg gtaatgccga aattgaacca    600
ccgaaatcga tcacaacagc aaccgcagtc agtgcacaaa ttatcgcaca agtcgcgagc    660
catatttacg gtggtaccac gattaaccgt atagatgaaa tccttgcccc ttatgtgcaa    720
ttaagttatg aaaaacattt aaaaaatgca gcggaatgga aagttcccga accagaagcc    780
tacgcgaaag cactcattga aaaagaatgt ttcgacgctt ttcaatcctt agaatatgaa    840
gtcaatacgc tgcatacttc aaatgggcaa accccttttg tcacttttgg ctttggctta    900
ggaacgacgt ggcaatcgag acttatccag cgctcaattc tgaaaaatcg tattcgtggt    960
ttaggcaaaa atcacaaaac ccctgtcttc ccaaaactgg tgttcactat taaaaaaggc   1020
attaaccata gcccgagtga tcctaactac gacattaaac aactggcttt agaatgtgcc   1080
tccaaacgga tgtatcctga tattctcaat tatgatcagg tggtgaaagt cacgggttct   1140
tttaaagcac caatgggatg ccgtagtttc ttaggtgctt atcaggagca aggacaggaa   1200
```

-continued

```
atccatgatg gacgtaataa cttaggcgta gtgagtttga atttaccgcg tatagcaatt   1260
gaagccaacg ccacgaattc agcccaaagt gcggtcgagt tttataaaat tttagatcaa   1320
cgtcttgcga ttgccaaaaa agccttaatg acacgcattg cacgtttaga acataccaaa   1380
gctcgcgttg ccccaattct ttatatggag ggtgcctgtg gtgtacgctt aaaggctgat   1440
gacaatgtgg cacaaatctt taaaaatggg cgtgcctcta tttcgttagg ctatattggt   1500
atccatgaaa caatcaatgc cctctacggc gataaacata tttatgatga tgaacaactc   1560
cgccaaaaag ggattgaaat cgtcgaatat ttacacgaga ccgtgcaacg ttggaaacaa   1620
gaaacaggtt atgctttcag cctatattcc acaccaagtg aaaacctttg tgaccgtttc   1680
tgtcgcttgg atactaagca atttgggctt atcgaaggtg tcacagataa aggctactat   1740
actaatagct accacttaga cgtagagaaa aaagtcaatc cttatgacaa gatagatttt   1800
gaattgcctt atccaccgtt cgcaagcggc gggtttattt gctatggtga atacccaaat   1860
gttcagcata accttaaagc attagaggac gtttgggatt atagctatga cagagtgcct   1920
tactatggga ccaatacacc gattgatgaa tgctatgaat gtggtttcag tggtgaattt   1980
gaatgtacca gtaaagggtt tacttgtccg aaatgtggta accatgacag tgagaaagtc   2040
tccgtgaccc gacgtgtctg tggctatctt ggcagtccag atgccagacc atttaatgcc   2100
ggtaaacaag aagaagtcaa gcgcagagta aaacatctct aa                      2142
```

<210> SEQ ID NO 23
<211> LENGTH: 713
<212> TYPE: PRT
<213> ORGANISM: Pasteurella multocida

<400> SEQUENCE: 23

```
Met Ala Thr Phe Phe Val Ile Lys Arg Asp Gly Ser Arg Thr Gly Phe
1               5                   10                  15

Glu Ile Gln Arg Ile Ile Asn Ala Ile Lys Lys Ala Ala Gln Ala Val
            20                  25                  30

Asn Ile Glu Asp Glu Arg Tyr Cys His Thr Met Gly Gln Gln Val Cys
        35                  40                  45

Asn Asp Ile Phe Thr Arg Tyr Gln Gln Glu Ile Asp Ile Ser His Ile
    50                  55                  60

Gln Lys Ile Val Glu Asn Thr Leu Met Ala Gly Lys Tyr Pro Glu Ile
65                  70                  75                  80

Ala Arg Ala Tyr Ile Glu Tyr Arg His Asp Arg Asp Leu Ala Arg Glu
                85                  90                  95

Lys Arg Ser Gln Leu Thr Lys Glu Ile Glu Gly Leu Ile Gln Gln Ser
            100                 105                 110

Asn Val Glu Leu Leu Asn Glu Asn Ala Asn Lys Asp Ala Lys Val Ile
        115                 120                 125

Pro Thr Gln Arg Asp Leu Leu Ala Gly Ile Val Ala Lys His Tyr Ala
    130                 135                 140

Lys Arg Tyr Ile Leu Pro Arg Asp Val Val Asp Ala His Glu Lys Gly
145                 150                 155                 160

Glu Ile His Tyr His Asp Leu Asp Tyr Ala Pro Phe Phe Pro Met Phe
                165                 170                 175

Asn Cys Met Leu Val Asp Leu Lys Gly Met Leu Ser Asn Gly Phe Lys
            180                 185                 190

Met Gly Asn Ala Glu Ile Glu Pro Pro Lys Ser Ile Thr Thr Ala Thr
        195                 200                 205
```

-continued

```
Ala Val Ser Ala Gln Ile Ile Ala Gln Val Ala Ser His Ile Tyr Gly
    210                 215                 220
Gly Thr Thr Ile Asn Arg Ile Asp Glu Ile Leu Ala Pro Tyr Val Gln
225                 230                 235                 240
Leu Ser Tyr Glu Lys His Leu Lys Asn Ala Ala Glu Trp Lys Val Pro
                245                 250                 255
Glu Pro Glu Ala Tyr Ala Lys Ala Leu Ile Glu Lys Glu Cys Phe Asp
            260                 265                 270
Ala Phe Gln Ser Leu Glu Tyr Glu Val Asn Thr Leu His Thr Ser Asn
        275                 280                 285
Gly Gln Thr Pro Phe Val Thr Phe Gly Phe Gly Leu Gly Thr Thr Trp
    290                 295                 300
Gln Ser Arg Leu Ile Gln Arg Ser Ile Leu Lys Asn Arg Ile Arg Gly
305                 310                 315                 320
Leu Gly Lys Asn His Lys Thr Pro Val Phe Pro Lys Leu Val Phe Thr
                325                 330                 335
Ile Lys Lys Gly Ile Asn His Ser Pro Ser Asp Pro Asn Tyr Asp Ile
            340                 345                 350
Lys Gln Leu Ala Leu Glu Cys Ala Ser Lys Arg Met Tyr Pro Asp Ile
        355                 360                 365
Leu Asn Tyr Asp Gln Val Val Lys Val Thr Gly Ser Phe Lys Ala Pro
    370                 375                 380
Met Gly Cys Arg Ser Phe Leu Gly Ala Tyr Gln Glu Gln Gly Gln Glu
385                 390                 395                 400
Ile His Asp Gly Arg Asn Asn Leu Gly Val Val Ser Leu Asn Leu Pro
                405                 410                 415
Arg Ile Ala Ile Glu Ala Asn Ala Thr Asn Ser Ala Gln Ser Ala Val
            420                 425                 430
Glu Phe Tyr Lys Ile Leu Asp Gln Arg Leu Ala Ile Ala Lys Lys Ala
        435                 440                 445
Leu Met Thr Arg Ile Ala Arg Leu Glu His Thr Lys Ala Arg Val Ala
    450                 455                 460
Pro Ile Leu Tyr Met Glu Gly Ala Cys Gly Val Arg Leu Lys Ala Asp
465                 470                 475                 480
Asp Asn Val Ala Gln Ile Phe Lys Asn Gly Arg Ala Ser Ile Ser Leu
                485                 490                 495
Gly Tyr Ile Gly Ile His Glu Thr Ile Asn Ala Leu Tyr Gly Asp Lys
            500                 505                 510
His Ile Tyr Asp Asp Glu Gln Leu Arg Gln Lys Gly Ile Glu Ile Val
        515                 520                 525
Glu Tyr Leu His Glu Thr Val Gln Arg Trp Lys Gln Glu Thr Gly Tyr
    530                 535                 540
Ala Phe Ser Leu Tyr Ser Thr Pro Ser Glu Asn Leu Cys Asp Arg Phe
545                 550                 555                 560
Cys Arg Leu Asp Thr Lys Gln Phe Gly Leu Ile Glu Gly Val Thr Asp
                565                 570                 575
Lys Gly Tyr Tyr Thr Asn Ser Tyr His Leu Asp Val Glu Lys Lys Val
            580                 585                 590
Asn Pro Tyr Asp Lys Ile Asp Phe Glu Leu Pro Tyr Pro Pro Phe Ala
        595                 600                 605
Ser Gly Gly Phe Ile Cys Tyr Gly Glu Tyr Pro Asn Val Gln His Asn
    610                 615                 620
Leu Lys Ala Leu Glu Asp Val Trp Asp Tyr Ser Tyr Asp Arg Val Pro
```

-continued

```
625                 630                 635                 640

Tyr Tyr Gly Thr Asn Thr Pro Ile Asp Glu Cys Tyr Glu Cys Gly Phe
                645                 650                 655
Ser Gly Glu Phe Glu Cys Thr Ser Lys Gly Phe Thr Cys Pro Lys Cys
            660                 665                 670
Gly Asn His Asp Ser Glu Lys Val Ser Val Thr Arg Arg Val Cys Gly
        675                 680                 685
Tyr Leu Gly Ser Pro Asp Ala Arg Pro Phe Asn Ala Gly Lys Gln Glu
    690                 695                 700
Glu Val Lys Arg Arg Val Lys His Leu
705                 710
```

<210> SEQ ID NO 24
<211> LENGTH: 58
<212> TYPE: DNA
<213> ORGANISM: Pasteurella multocida

<400> SEQUENCE: 24

```
attgtgatta cgggattatc gggatcaggt aaatcttctt tagcctttga taccctgt       58
```

<210> SEQ ID NO 25
<211> LENGTH: 2832
<212> TYPE: DNA
<213> ORGANISM: Pasteurella multocida

<400> SEQUENCE: 25

```
atggataaga ttgaggtacg tggggcgaga acccataatt taaaaaatat taatttaact     60
attcctcgtg ataaattaat tgtgattacg ggattatcgg gatcaggtaa atcttcttta    120
gcctttgata ccctgtatgc tgagggacaa cgccgttatg tagaatcctt gtcggcatat    180
gcacgtcaat tcttatccct aatggaaaag ccggatgtgg atcatattga aggattatcg    240
ccggcgattt ctattgaaca aaaatctacc tcacataatc cgcgttcaac ggtgggtacg    300
gtcaccgaaa ttcatgatta cttacgtctt ctttttgctc gagtagggga accgcgttgt    360
ccgaatcatg atgtgccttt agcggcacaa accattagcc agatggtgga taaagtattg    420
agtttgcctg aagaaagcaa aatgatgttg ctggcgccag tggtgaaaga acgtaagggt    480
gaacatgtta aattattaga gcaaattgcc gcccaaggtt atattcgagc cagaattgac    540
ggtgaaattt gtgatttatc tgatgcacct aaattagaat tacataaaaa acatactatt    600
gaagtggttg tggaccgttt taaggtgcgg tctgatttag ccacaagatt agcagaatcc    660
tttgaaacag cattggaatt atctggtggc accgctgtag ttgcttccat ggatgagcct    720
gaaacggaag aattggtctt ttcggctaat tttgcttgtc cacattgtgg gtattctgtc    780
ccagaattag aacctcgttt attttctttt aataatcccg ccggggcgtg tccgacttgc    840
gatggcttag gtgtacaaca atattttgat gaaaaacgcg tggtgcaaaa cccgagtatt    900
tcgttagcca gtggcgcagt aaaaggctgg gatcgtcgta acttctatta ctaccaaatg    960
ctcacctcct tagcgaagca ttatgaattt gatattgaat cacctttgga ggcactgccg   1020
aaaaaaatcc agcagattat tttaaatggt tcaggtaagg aagaaattga gtttcaatac   1080
atgaatgatc gcggcgatgt agtcgtgcgt catcatgcat ttgaaggcat tctaaataat   1140
atggcgcgcc gttataaaga aacggaatcg ctgtctgtgc gtgaagaatt agcgaaaaat   1200
atcagtacct gtccttgcca tgattgtggg ggttcacgtt tacgtcaaga ggcacgtcat   1260
gtgtatattg gcaccaccac tttacctgat gtggcagaaa agagtattgg cgaaaccttg   1320
```

-continued

```
catttcttta gtgaattgca tttaagcggg caaagagctc aaattgccga gaaaatctta   1380
aaagaaatta aagagcgctt acaattttta gtcaatgtag ggttggatta tctttccctt   1440
tctcgttcag cagaaacctt gtctggtggg gaggcacagc gaattcgttt agccagtcaa   1500
attggtgcgg gtttagtggg ggtgatgtat gtgctagatg agccgtctat tggtttgcat   1560
caacgtgata atgagcgatt actgaataca ttgcttcact tacgtaactt agggaacacc   1620
gtgattgtgg tagaacatga tgaagatgcc attatggcgg cagatcatat tattgatatt   1680
ggtcccgggg caggagttca tggtgggcaa attgtggcag aaggttcggc aaaggcgatt   1740
atggctaatc cacactcaat tacggggaaa tttttatctg ggtcgagaa aatcgaaatt    1800 cccgcaaaac ggaccgcact tgataagaaa aaaatgttga aattagaagg ggcaacgggg   1860
aataatctga aatcagtgaa tttagccatt ccagtaggat tgtttacctg tgtgacaggt   1920
gtttcggggt cagggaaatc gaccttgatt aatgatacgt tgttcccatt agcacaaaat   1980
gccttgaatc gtgcggaaaa tacgcaattt gcgccttatc aatccatttc gggtttggaa   2040 tttttgata aagtaattga tattgaccaa agtccaattg gtcgtacacc gcgttcgaat    2100
cctgccactt atactggctt atttacgccg attcgagaat tatttgcggg cgtgcctgag   2160
tcgagagccc ggggttataa tcccggacgt tttagtttta atgtacgcgg tggacgctgt   2220
gaggcctgtc aaggcgatgg tgtgattaaa gtagagatgc actttttgcc cgatgtgtat   2280
gtgccttgtg agcaatgtaa gggaaaacgt tataatcgag agaccttaga gatccgttac   2340
aaaggtaaaa cgattcatca agtgttagaa atgacggtag aagaagcgcg cgagtttttt   2400
gatgcgattc cgcagatcgc ccgtaaatta caaactttaa tggatgttgg tttatcctat   2460
attcgtttag gacaatcttc gaccacgtta tcgggtgggg aagcgcaacg agtgaaatta   2520
gcaacggagc tttcaaaacg tgatacaggg aaaactttgt atgtattaga tgaaccgacg   2580
acaggtttac attttgctga tattaaacag ctattaacag tcttgcatcg tttacgtgat   2640
caaggcaata cgatagtggt gattgagcac aatttagatg tgatcaaaac agccgattgg   2700
attattgatt taggtcctga agggggggaat ggcggtggac aaattattgc cacaggcaca   2760
ccagaacagg tcgctgaagt gaaaggttca cataccgcac gcttcttaaa aacgctttta   2820
caaaagcgct aa                                                       2832
```

<210> SEQ ID NO 26
<211> LENGTH: 943
<212> TYPE: PRT
<213> ORGANISM: Pasteurella multocida

<400> SEQUENCE: 26

```
Met Asp Lys Ile Glu Val Arg Gly Ala Arg Thr His Asn Leu Lys Asn
1               5                   10                  15

Ile Asn Leu Thr Ile Pro Arg Asp Lys Leu Ile Val Ile Thr Gly Leu
            20                  25                  30

Ser Gly Ser Gly Lys Ser Ser Leu Ala Phe Asp Thr Leu Tyr Ala Glu
        35                  40                  45

Gly Gln Arg Arg Tyr Val Glu Ser Leu Ser Ala Tyr Ala Arg Gln Phe
    50                  55                  60

Leu Ser Leu Met Glu Lys Pro Asp Val Asp His Ile Glu Gly Leu Ser
65                  70                  75                  80

Pro Ala Ile Ser Ile Glu Gln Lys Ser Thr Ser His Asn Pro Arg Ser
                85                  90                  95

Thr Val Gly Thr Val Thr Glu Ile His Asp Tyr Leu Arg Leu Leu Phe
```

-continued

```
                100                 105                 110
Ala Arg Val Gly Glu Pro Arg Cys Pro Asn His Asp Val Pro Leu Ala
            115                 120                 125
Ala Gln Thr Ile Ser Gln Met Val Asp Lys Val Leu Ser Leu Pro Glu
        130                 135                 140
Glu Ser Lys Met Met Leu Leu Ala Pro Val Val Lys Glu Arg Lys Gly
145                 150                 155                 160
Glu His Val Lys Leu Leu Glu Gln Ile Ala Ala Gln Gly Tyr Ile Arg
                165                 170                 175
Ala Arg Ile Asp Gly Glu Ile Cys Asp Leu Ser Asp Ala Pro Lys Leu
            180                 185                 190
Glu Leu His Lys Lys His Thr Ile Glu Val Val Asp Arg Phe Lys
        195                 200                 205
Val Arg Ser Asp Leu Ala Thr Arg Leu Ala Glu Ser Phe Glu Thr Ala
210                 215                 220
Leu Glu Leu Ser Gly Gly Thr Ala Val Val Ala Ser Met Asp Glu Pro
225                 230                 235                 240
Glu Thr Glu Glu Leu Val Phe Ser Ala Asn Phe Ala Cys Pro His Cys
                245                 250                 255
Gly Tyr Ser Val Pro Glu Leu Glu Pro Arg Leu Phe Ser Phe Asn Asn
            260                 265                 270
Pro Ala Gly Ala Cys Pro Thr Cys Asp Gly Leu Gly Val Gln Gln Tyr
        275                 280                 285
Phe Asp Glu Lys Arg Val Val Gln Asn Pro Ser Ile Ser Leu Ala Ser
290                 295                 300
Gly Ala Val Lys Gly Trp Asp Arg Arg Asn Phe Tyr Tyr Tyr Gln Met
305                 310                 315                 320
Leu Thr Ser Leu Ala Lys His Tyr Glu Phe Asp Ile Glu Ser Pro Phe
                325                 330                 335
Glu Ala Leu Pro Lys Lys Ile Gln Gln Ile Ile Leu Asn Gly Ser Gly
            340                 345                 350
Lys Glu Glu Ile Glu Phe Gln Tyr Met Asn Asp Arg Gly Asp Val Val
        355                 360                 365
Val Arg His His Ala Phe Glu Gly Ile Leu Asn Asn Met Ala Arg Arg
370                 375                 380
Tyr Lys Glu Thr Glu Ser Leu Ser Val Arg Glu Glu Leu Ala Lys Asn
385                 390                 395                 400
Ile Ser Thr Cys Pro Cys His Asp Cys Gly Gly Ser Arg Leu Arg Gln
                405                 410                 415
Glu Ala Arg His Val Tyr Ile Gly Thr Thr Thr Leu Pro Asp Val Ala
            420                 425                 430
Glu Lys Ser Ile Gly Glu Thr Leu His Phe Phe Ser Glu Leu His Leu
        435                 440                 445
Ser Gly Gln Arg Ala Gln Ile Ala Glu Lys Ile Leu Lys Glu Ile Lys
450                 455                 460
Glu Arg Leu Gln Phe Leu Val Asn Val Gly Leu Asp Tyr Leu Ser Leu
465                 470                 475                 480
Ser Arg Ser Ala Glu Thr Leu Ser Gly Gly Glu Ala Gln Arg Ile Arg
                485                 490                 495
Leu Ala Ser Gln Ile Gly Ala Gly Leu Val Gly Val Met Tyr Val Leu
            500                 505                 510
Asp Glu Pro Ser Ile Gly Leu His Gln Arg Asp Asn Glu Arg Leu Leu
        515                 520                 525
```

-continued

```
Asn Thr Leu Leu His Leu Arg Asn Leu Gly Asn Thr Val Ile Val Val
    530                 535                 540

Glu His Asp Glu Asp Ala Ile Met Ala Ala Asp His Ile Ile Asp Ile
545                 550                 555                 560

Gly Pro Gly Ala Gly Val His Gly Gly Gln Ile Val Ala Glu Gly Ser
                565                 570                 575

Ala Lys Ala Ile Met Ala Asn Pro His Ser Ile Thr Gly Lys Phe Leu
                580                 585                 590

Ser Gly Val Glu Lys Ile Glu Ile Pro Ala Lys Arg Thr Ala Leu Asp
            595                 600                 605

Lys Lys Lys Met Leu Lys Leu Glu Gly Ala Thr Gly Asn Asn Leu Lys
            610                 615                 620

Ser Val Asn Leu Ala Ile Pro Val Gly Leu Phe Thr Cys Val Thr Gly
625                 630                 635                 640

Val Ser Gly Ser Gly Lys Ser Thr Leu Ile Asn Asp Thr Leu Phe Pro
                645                 650                 655

Leu Ala Gln Asn Ala Leu Asn Arg Ala Glu Asn Thr Gln Phe Ala Pro
                660                 665                 670

Tyr Gln Ser Ile Ser Gly Leu Glu Phe Phe Asp Lys Val Ile Asp Ile
            675                 680                 685

Asp Gln Ser Pro Ile Gly Arg Thr Pro Arg Ser Asn Pro Ala Thr Tyr
    690                 695                 700

Thr Gly Leu Phe Thr Pro Ile Arg Glu Leu Phe Ala Gly Val Pro Glu
705                 710                 715                 720

Ser Arg Ala Arg Gly Tyr Asn Pro Gly Arg Phe Ser Phe Asn Val Arg
                725                 730                 735

Gly Gly Arg Cys Glu Ala Cys Gln Gly Asp Gly Val Ile Lys Val Glu
                740                 745                 750

Met His Phe Leu Pro Asp Val Tyr Val Pro Cys Glu Gln Cys Lys Gly
            755                 760                 765

Lys Arg Tyr Asn Arg Glu Thr Leu Glu Ile Arg Tyr Lys Gly Lys Thr
    770                 775                 780

Ile His Gln Val Leu Glu Met Thr Val Glu Glu Ala Arg Glu Phe Phe
785                 790                 795                 800

Asp Ala Ile Pro Gln Ile Ala Arg Lys Leu Gln Thr Leu Met Asp Val
                805                 810                 815

Gly Leu Ser Tyr Ile Arg Leu Gly Gln Ser Ser Thr Thr Leu Ser Gly
                820                 825                 830

Gly Glu Ala Gln Arg Val Lys Leu Ala Thr Glu Leu Ser Lys Arg Asp
            835                 840                 845

Thr Gly Lys Thr Leu Tyr Val Leu Asp Glu Pro Thr Thr Gly Leu His
    850                 855                 860

Phe Ala Asp Ile Lys Gln Leu Leu Thr Val Leu His Arg Leu Arg Asp
865                 870                 875                 880

Gln Gly Asn Thr Ile Val Val Ile Glu His Asn Leu Asp Val Ile Lys
                885                 890                 895

Thr Ala Asp Trp Ile Ile Asp Leu Gly Pro Glu Gly Gly Asn Gly Gly
                900                 905                 910

Gly Gln Ile Ile Ala Thr Gly Thr Pro Glu Gln Val Ala Glu Val Lys
            915                 920                 925

Gly Ser His Thr Ala Arg Phe Leu Lys Thr Leu Leu Gln Lys Arg
    930                 935                 940
```

<210> SEQ ID NO 27
<211> LENGTH: 54
<212> TYPE: DNA
<213> ORGANISM: Pasteurella multocida

<400> SEQUENCE: 27
caggacttag tgggtaacaa cacaccagtc ttctttatcc gtgatccatt gaaa 54

<210> SEQ ID NO 28
<211> LENGTH: 1455
<212> TYPE: DNA
<213> ORGANISM: Pasteurella multocida

<400> SEQUENCE: 28
atgtctaaat gcccatttga ccatggttca aaaaccttaa cgaatgcagc tggtgcacct 60
attgttgaaa acgacaacac catgtctgcg ggtcctaaag gtccattact tttacaagat 120
gtttggttcc aagagaaatt agcacacttt gcacgtgagc gtattcctga gcgtgttgtt 180
catgcaaaag gttcagcagc gtacggtaca ttcactgtga cacacgatat cagcaaatac 240
accaaagcgg atttattcaa tggtatcggt aaacaaacac aagtcttatt acgtttctca 300
acagtagcgg gtgagcgcgg tgcggcagac gctgagcgtg atgtgcgtgg tttcgcatta 360
aaattctaca ctgaacaagg taactgggac ttagtgggta acaacacacc cgtattcttt 420
atccgtgatc cattgaaatt cccagatttc attcatactc aaaaacgtaa tccacaaact 480
aacttgcgtg atgcaaacgc ggcatgggat ttctggtcac gtcatcctga atcattacac 540
caaatcatga ttcttttcag tgatcgtggt attccaactg acttacgtca tatgaacggt 600
tacggtagcc atacatatag ctttattaac gcacaaaatg agcgtttctg ggtgaaattc 660
cacttcaaaa cacaacaagg tcacaaattc tatactaatg aagaagcggc taaagtggtg 720
ggtgaaaacc gtgagtcaag ccaacaagat ttatacgaag cgattgagcg tggcgaattc 780
ccacgttgga atgttcaagt gcaaatcatg ccagaagcag atgcacacaa acataactat 840
gcgtttgact taactaaagt atggccacac aaagattatc cgatgatcga agtgggtgta 900
ttagagttaa accaaaaccc aattaactac ttcgcagaag tggaacaagc tgcgtttgca 960
ccttctaaca tcgtaccggg aattggtttc tcaccagacc gtatgttaca aggtcgtctt 1020
ttctcatacc aagacgcgca acgttatcgt ttaggggtta accatcacca aatcccagtg 1080
aacgcaccaa aatgcccata ccacaccact caccgtgatg gcgcaatgcg tgtagataac 1140
aatggtggta cacaccctaa ctatgcaccg aaccgttttg atacttatgt gccgactcac 1200
caacaagagc ctgcattaga gttagagcgt tcagcagcac actttaactt ccgtgagtat 1260
gatgaagact actacacaca acctgccgca ctttacaact tattcgatgt ggatcaaaaa 1320
gcacgtgtgg cagccaactt cgcagcgggc ttagcaggtg ttacagaacc tgcgattgtt 1380
gaaagacaat tagcccactt cgacaaagta agcaaagaat tagctgatgc aattcgtgcg 1440
aacttagcga aataa 1455

<210> SEQ ID NO 29
<211> LENGTH: 484
<212> TYPE: PRT
<213> ORGANISM: Pasteurella multocida

<400> SEQUENCE: 29

Met Ser Lys Cys Pro Phe Asp His Gly Ser Lys Thr Leu Thr Asn Ala
1 5 10 15

-continued

```
Ala Gly Ala Pro Ile Val Glu Asn Asp Asn Thr Met Ser Ala Gly Pro
            20                  25                  30

Lys Gly Pro Leu Leu Gln Asp Val Trp Phe Gln Glu Lys Leu Ala
        35                  40                  45

His Phe Ala Arg Glu Arg Ile Pro Glu Arg Val Val His Ala Lys Gly
    50                  55                  60

Ser Ala Ala Tyr Gly Thr Phe Thr Val Thr His Asp Ile Ser Lys Tyr
65                  70                  75                  80

Thr Lys Ala Asp Leu Phe Asn Gly Ile Gly Lys Gln Thr Gln Val Leu
                85                  90                  95

Leu Arg Phe Ser Thr Val Ala Gly Glu Arg Gly Ala Ala Asp Ala Glu
            100                 105                 110

Arg Asp Val Arg Gly Phe Ala Leu Lys Phe Tyr Thr Glu Gln Gly Asn
        115                 120                 125

Trp Asp Leu Val Gly Asn Asn Thr Pro Val Phe Phe Ile Arg Asp Pro
    130                 135                 140

Leu Lys Phe Pro Asp Phe Ile His Thr Gln Lys Arg Asn Pro Gln Thr
145                 150                 155                 160

Asn Leu Arg Asp Ala Asn Ala Ala Trp Asp Phe Trp Ser Arg His Pro
                165                 170                 175

Glu Ser Leu His Gln Ile Met Ile Leu Phe Ser Asp Arg Gly Ile Pro
            180                 185                 190

Thr Asp Leu Arg His Met Asn Gly Tyr Gly Ser His Thr Tyr Ser Phe
        195                 200                 205

Ile Asn Ala Gln Asn Glu Arg Phe Trp Val Lys Phe His Phe Lys Thr
    210                 215                 220

Gln Gln Gly His Lys Phe Tyr Thr Asn Glu Glu Ala Ala Lys Val Val
225                 230                 235                 240

Gly Glu Asn Arg Glu Ser Ser Gln Gln Asp Leu Tyr Glu Ala Ile Glu
                245                 250                 255

Arg Gly Glu Phe Pro Arg Trp Asn Val Gln Val Gln Ile Met Pro Glu
            260                 265                 270

Ala Asp Ala His Lys His Asn Tyr Ala Phe Asp Leu Thr Lys Val Trp
        275                 280                 285

Pro His Lys Asp Tyr Pro Met Ile Glu Val Gly Val Leu Glu Leu Asn
    290                 295                 300

Gln Asn Pro Ile Asn Tyr Phe Ala Glu Val Glu Gln Ala Ala Phe Ala
305                 310                 315                 320

Pro Ser Asn Ile Val Pro Gly Ile Gly Phe Ser Pro Asp Arg Met Leu
                325                 330                 335

Gln Gly Arg Leu Phe Ser Tyr Gln Asp Ala Gln Arg Tyr Arg Leu Gly
            340                 345                 350

Val Asn His His Gln Ile Pro Val Asn Ala Pro Lys Cys Pro Tyr His
        355                 360                 365

Thr Thr His Arg Asp Gly Ala Met Arg Val Asp Asn Asn Gly Gly Thr
    370                 375                 380

His Pro Asn Tyr Ala Pro Asn Arg Phe Asp Thr Tyr Val Pro Thr His
385                 390                 395                 400

Gln Gln Glu Pro Ala Leu Glu Leu Glu Arg Ser Ala Ala His Phe Asn
                405                 410                 415

Phe Arg Glu Tyr Asp Glu Asp Tyr Tyr Thr Gln Pro Ala Ala Leu Tyr
            420                 425                 430

Asn Leu Phe Asp Val Asp Gln Lys Ala Arg Val Ala Ala Asn Phe Ala
```

-continued

```
        435                 440                 445

Ala Gly Leu Ala Gly Val Thr Glu Pro Ala Ile Val Glu Arg Gln Leu
    450                 455                 460

Ala His Phe Asp Lys Val Ser Lys Glu Leu Ala Asp Ala Ile Arg Ala
465                 470                 475                 480

Asn Leu Ala Lys

<210> SEQ ID NO 30
<211> LENGTH: 172
<212> TYPE: DNA
<213> ORGANISM: Pasteurella multocida

<400> SEQUENCE: 30
atttctcacg catttttcg gtaaaaccaa cgggaatcgt tgattttata ataatcgttg      60
cttgtggatt gattgagagg gtttgttcaa tgacagcttc aacagtggat gtattaaaat     120
aacctgtttc ggtattatag tctgttggcg ttgcgatgat gacaaagtcc tg             172

<210> SEQ ID NO 31
<211> LENGTH: 1173
<212> TYPE: DNA
<213> ORGANISM: Pasteurella multocida

<400> SEQUENCE: 31
atgaagaaaa ttacaattgc tggggctggc tatgttggtt tatccaatgc agtattatta      60
gctcaacacc acaatgtgat cttattagat attgatcaaa ataaagttga tttaattaat     120
aataaaaaat cgcccatcac agataaagaa atcgaagatt tcttacaaaa taaatcactg     180
acaatgatgg caacaacaga taaagaagtg gcattaaaaa acgcagactt tgtcatcatc     240
gcaacgccaa cagactataa taccgaaaca ggttatttta atacatccac tgttgaagct     300
gtcattgaac aaaccctttc aatcaatcca caagcaacga ttattataaa atcaacaatt     360
cccgttggtt ttaccgaaaa catgcgtgaa aaatttaata ccccaaatct tatcttttca     420
cctgaatttc taagagaggg aaaagccctt tacgataatt tgtatccaag cagaattatt     480
gttggcagta cttcttatca agcaaaagta tttgccgata tgttgacaca gtgtgccaga     540
aaaaaagatg taactgtttt atttacacac aatactgagg ccgaagctgt taaattattt     600
gcaaatacgt atctcgcaat gcgagttgcc ttttttaatg aattagatac ttatgcgagt     660
cttcaccatt taaatacaaa agacattatc aatggtattt ctactgatcc tcgcattggt     720
acacactaca ataacccaag tttcggctat ggcggttatt gtttacccaa agacactaaa     780
cagttactgg ctaactatgc tgacgtgcct caaaatctca ttgaagccat tgtcaaatct     840
aatgaaacca gaaaacgttt cattactcat gatgtattaa ataagaaacc taaaactgtt     900
ggtatttatc gtttaatcat gaagtcaggt tctgataact tcagagcttc tgctattctc     960
gatattatgc cgcatctcaa agaaaacggt gttgagattg tgatttatga gccaacctta    1020
aatcaacagg catttgagga ctaccccgtt attaatcaac tctctgaatt tattaatcgc    1080
tctgatgtca ttctcgctaa tcgttctgag ccagatttaa atcaatgttc ccataaaatc    1140
tatacaagag atatttttgg cggtgatgct taa                                 1173

<210> SEQ ID NO 32
<211> LENGTH: 390
<212> TYPE: PRT
<213> ORGANISM: Pasteurella multocida

<400> SEQUENCE: 32
```

```
Met Lys Lys Ile Thr Ile Ala Gly Ala Gly Tyr Val Gly Leu Ser Asn
1               5                   10                  15

Ala Val Leu Leu Ala Gln His His Asn Val Ile Leu Asp Ile Asp
            20                  25                  30

Gln Asn Lys Val Asp Leu Ile Asn Asn Lys Lys Ser Pro Ile Thr Asp
        35                  40                  45

Lys Glu Ile Glu Asp Phe Leu Gln Asn Lys Ser Leu Thr Met Met Ala
    50                  55                  60

Thr Thr Asp Lys Glu Val Ala Leu Lys Asn Ala Asp Phe Val Ile Ile
65                  70                  75                  80

Ala Thr Pro Thr Asp Tyr Asn Thr Glu Thr Gly Tyr Phe Asn Thr Ser
                85                  90                  95

Thr Val Glu Ala Val Ile Glu Gln Thr Leu Ser Ile Asn Pro Gln Ala
            100                 105                 110

Thr Ile Ile Ile Lys Ser Thr Ile Pro Val Gly Phe Thr Glu Asn Met
            115                 120                 125

Arg Glu Lys Phe Asn Thr Pro Asn Leu Ile Phe Ser Pro Glu Phe Leu
    130                 135                 140

Arg Glu Gly Lys Ala Leu Tyr Asp Asn Leu Tyr Pro Ser Arg Ile Ile
145                 150                 155                 160

Val Gly Ser Thr Ser Tyr Gln Ala Lys Val Phe Ala Asp Met Leu Thr
                165                 170                 175

Gln Cys Ala Arg Lys Lys Asp Val Thr Val Leu Phe Thr His Asn Thr
            180                 185                 190

Glu Ala Glu Ala Val Lys Leu Phe Ala Asn Thr Tyr Leu Ala Met Arg
    195                 200                 205

Val Ala Phe Phe Asn Glu Leu Asp Thr Tyr Ala Ser Leu His His Leu
    210                 215                 220

Asn Thr Lys Asp Ile Ile Asn Gly Ile Ser Thr Asp Pro Arg Ile Gly
225                 230                 235                 240

Thr His Tyr Asn Asn Pro Ser Phe Gly Tyr Gly Gly Tyr Cys Leu Pro
                245                 250                 255

Lys Asp Thr Lys Gln Leu Leu Ala Asn Tyr Ala Asp Val Pro Gln Asn
            260                 265                 270

Leu Ile Glu Ala Ile Val Lys Ser Asn Glu Thr Arg Lys Arg Phe Ile
            275                 280                 285

Thr His Asp Val Leu Asn Lys Lys Pro Lys Thr Val Gly Ile Tyr Arg
    290                 295                 300

Leu Ile Met Lys Ser Gly Ser Asp Asn Phe Arg Ala Ser Ala Ile Leu
305                 310                 315                 320

Asp Ile Met Pro His Leu Lys Glu Asn Gly Val Glu Ile Val Ile Tyr
                325                 330                 335

Glu Pro Thr Leu Asn Gln Gln Ala Phe Glu Asp Tyr Pro Val Ile Asn
            340                 345                 350

Gln Leu Ser Glu Phe Ile Asn Arg Ser Asp Val Ile Leu Ala Asn Arg
            355                 360                 365

Ser Glu Pro Asp Leu Asn Gln Cys Ser His Lys Ile Tyr Thr Arg Asp
    370                 375                 380

Ile Phe Gly Gly Asp Ala
385                 390
```

<210> SEQ ID NO 33

-continued

<211> LENGTH: 226
<212> TYPE: DNA
<213> ORGANISM: Pasteurella multocida

<400> SEQUENCE: 33
gcaccaaagt gaataatatt tgggaaacct cgggcttgaa tattttagag gtattagtac 60
gtttagatag caccaagtta cctagtttca tttctaacat cctgtccgcg cgaaccaata 120
tttcggcaat ctatattcaa aaagccttca aagtagaacc acagaaatca ctcgaagcgt 180
ttaaggatct tgatactcta gcagatacag cagaagctta tactaa 226

<210> SEQ ID NO 34
<211> LENGTH: 726
<212> TYPE: DNA
<213> ORGANISM: Pasteurella multocida

<400> SEQUENCE: 34
atgaataatg atcaacctct tttaaaagca cagagtccgg ctggtttagc ggaagaatat 60
attgtcagaa gtatctggaa taatcatttc ccaccaggct ccgatttgcc ggctgaacgt 120
gagttggcag agaaaattgg ggtgacgcgt accacgttac gtgaagtgct acaacgcctg 180
gcgcgtgacg gttggttgaa tattcaacat gggaaaccaa ccaaagtgaa taatatttgg 240
gaaacttcgg gcttgaatat tttagaggta ttagtacgtt tagatagcac caagttacct 300
agtttcattt ctaacatcct gtccgcgcga accaatattt cggcaatcta tattcaaaaa 360
gccttcaaag tagaaccaca gaaatcactc gaagcgttta aggatcttga tactctagca 420
gatacagcag aagcttatac taattttgat tatgatcttt tccgtaaatt agcatttgca 480
tctgataatc ctgtgtatgg tttgatttta aatagtttga aagggttata tacacgtgta 540
gggttgtttt attttgccaa tccatcggcg cgtgagttag cgaaacgctt ttatctttcg 600
ctaaagacgt tgtgtcaaac acagcaagtg aacgatgtca aagagtgtat ccgtcaatat 660
ggtaaagaca gtggggtgat ttgggcaaat atgcaggcat atttaccggc taattttaat 720
gaatag 726

<210> SEQ ID NO 35
<211> LENGTH: 241
<212> TYPE: PRT
<213> ORGANISM: Pasteurella multocida

<400> SEQUENCE: 35

Met Asn Asn Asp Gln Pro Leu Leu Lys Ala Gln Ser Pro Ala Gly Leu
1 5 10 15

Ala Glu Glu Tyr Ile Val Arg Ser Ile Trp Asn Asn His Phe Pro Pro
20 25 30

Gly Ser Asp Leu Pro Ala Glu Arg Glu Leu Ala Glu Lys Ile Gly Val
35 40 45

Thr Arg Thr Thr Leu Arg Glu Val Leu Gln Arg Leu Ala Arg Asp Gly
50 55 60

Trp Leu Asn Ile Gln His Gly Lys Pro Thr Lys Val Asn Asn Ile Trp
65 70 75 80

Glu Thr Ser Gly Leu Asn Ile Leu Glu Val Leu Val Arg Leu Asp Ser
85 90 95

Thr Lys Leu Pro Ser Phe Ile Ser Asn Ile Leu Ser Ala Arg Thr Asn
100 105 110

Ile Ser Ala Ile Tyr Ile Gln Lys Ala Phe Lys Val Glu Pro Gln Lys
115 120 125

```
Ser Leu Glu Ala Phe Lys Asp Leu Asp Thr Leu Ala Asp Thr Ala Glu
    130                 135                 140

Ala Tyr Thr Asn Phe Asp Tyr Asp Leu Phe Arg Lys Leu Ala Phe Ala
145                 150                 155                 160

Ser Asp Asn Pro Val Tyr Gly Leu Ile Leu Asn Ser Leu Lys Gly Leu
                165                 170                 175

Tyr Thr Arg Val Gly Leu Phe Tyr Phe Ala Asn Pro Ser Ala Arg Glu
            180                 185                 190

Leu Ala Lys Arg Phe Tyr Leu Ser Leu Lys Thr Leu Cys Gln Thr Gln
        195                 200                 205

Gln Val Asn Asp Val Lys Glu Cys Ile Arg Gln Tyr Gly Lys Asp Ser
    210                 215                 220

Gly Val Ile Trp Ala Asn Met Gln Ala Tyr Leu Pro Ala Asn Phe Asn
225                 230                 235                 240

Glu

<210> SEQ ID NO 36
<211> LENGTH: 214
<212> TYPE: DNA
<213> ORGANISM: Pasteurella multocida

<400> SEQUENCE: 36
acaaccgctg gcgtatccgt taaacggtgg gttaagcgca cttctttcac gcgctcacca    60
agcaaggttt tcacacgttc acaaaagaa gcatattgct catcttgtgc tttttgactg    120
tcttcctctt tatccgctaa atcacctaga tctaaatccg ctttactgat ggtttgcagt    180
ggcttaccgt caaattccgt taagtaactt aaca                               214

<210> SEQ ID NO 37
<211> LENGTH: 1896
<212> TYPE: DNA
<213> ORGANISM: Pasteurella multocida

<400> SEQUENCE: 37
atgtcgacga atcaagaaac gcgtggtttt caatcagaag tcaaacaact tcttcaacta    60
atgatccatt ctctctattc caataaagaa atttcttac gtgaattaat ttccaatgcc    120
tctgatgcgg cagataaatt gcgttttaaa gccttgtctg tgccagagct ttatgaaggt    180
gatggggatt taaaagtgcg tattcgtttt gatgaagaga aaggtacctt aaccattagt    240
gataatggca ttgggatgac gcgtgatgaa gtaatcgatc atttaggtac cattgccaaa    300
tcgggtacca agaattttt aagtgcatta ggacaagatc aagccaaaga tagccaatta    360
attggtcagt ttggggtcgg ttttattcc gcctttattg tggcagataa agtcactgtg    420
aaaacgcgtg cagcaggcgt aagtgcagat aaagcggtgc tttgggaatc ggcaggcgaa    480
ggtgagtatt ctgtggcgga tattgacaaa aagaacgcg gtaccgaaat acccttcac    540 ttacgtgaag atgaaaaagc ctttttaaat gattggcgct acgtgaaat atccggcaaa    600 tattcggatc atattggttt gccagtagaa attctagcca agaatatga cgatgaaggc    660 aaagaaaccg gcattaaatg ggaaaaaatc aataaagcgc aagccttgtg gacacgtgca    720
aaaaatgaga tttcggagga agaatatcaa gagttctata gcatttaag tcatgatttt    780 accgatccgt tactttgggc acacaataaa gtagaaggaa atcaagaata taccagttta    840
ctttatgtgc cagcaaaagc cccttgggat ttatttaatc gcgaacataa acacggctta    900
aagctgtatg tgcaacgtgt ctttattatg gatgatgcgc aagtctttat gccaaattat    960
```

-continued

```
ctgcgtttta tgcgtggttt attagattcc aatgatttgc cactgaatgt atcgcgcgaa   1020
attttacaag ataacaaagt cacgagtgct ttacgtaaag ccctaacgaa acgtgcattg   1080
caaatgctcg aaaaattagc caaagacgat gcagagaaat accaacgctt ttggcaagag   1140
tttggtttgg tgttaaaaga aggtccagca gaagattttg caaataaaga aacgattgca   1200
aaattattac gttttgcttc aacacacaat gacagcagcc aacaaagcgt gtcgttagaa   1260
gactatgtgg cacgtatgaa agaaggacaa aaggcgattt attatattac ggcagatact   1320
tatgtcgccg cgaaaaactc accgcactta gaattgttca ataagaaagg cattgaagta   1380
ttattgttgt ccgatcgtat tgatgaatgg atgttaagct acttaacgga atttgatggt   1440
aagccactgc aaaccatcag taaagcggat ttagatctag gtgatttagc ggataaagag   1500
gaagacagtc aaaaagcaca agatgagcaa tatgcttctt ttgtggaacg tgtgaaaacc   1560
ttgcttggcg agcgcgtgaa agaagtgcgc ttaactcacc gtttaacgga tacgccagcg   1620
gttgtttcga cgggtgatga ccagatgacc acccaaatgg cgaaattgtt cgctgcggcg   1680
ggtcaagcga tgccagaggt taaatacacc ttcgaattaa atccagaaca tggtttagta   1740
caaaaagtag cagaaattgc cgatgagcag caatttgccg attggattga attgctactt   1800
gaacaagcaa tgttggctga gcgtggtagc cttgaaaatc cagttgcctt tattaaacgc   1860
atgaacacct tgttaagtaa actcacaagt cattaa                            1896

<210> SEQ ID NO 38
<211> LENGTH: 631
<212> TYPE: PRT
<213> ORGANISM: Pasteurella multocida

<400> SEQUENCE: 38

Met Ser Thr Asn Gln Glu Thr Arg Gly Phe Gln Ser Glu Val Lys Gln
1               5                   10                  15

Leu Leu Gln Leu Met Ile His Ser Leu Tyr Ser Asn Lys Glu Ile Phe
            20                  25                  30

Leu Arg Glu Leu Ile Ser Asn Ala Ser Asp Ala Ala Asp Lys Leu Arg
        35                  40                  45

Phe Lys Ala Leu Ser Val Pro Glu Leu Tyr Glu Gly Asp Gly Asp Leu
    50                  55                  60

Lys Val Arg Ile Arg Phe Asp Glu Glu Lys Gly Thr Leu Thr Ile Ser
65                  70                  75                  80

Asp Asn Gly Ile Gly Met Thr Arg Asp Glu Val Ile Asp His Leu Gly
                85                  90                  95

Thr Ile Ala Lys Ser Gly Thr Lys Glu Phe Leu Ser Ala Leu Gly Gln
            100                 105                 110

Asp Gln Ala Lys Asp Ser Gln Leu Ile Gly Gln Phe Gly Val Gly Phe
        115                 120                 125

Tyr Ser Ala Phe Ile Val Ala Asp Lys Val Thr Val Lys Thr Arg Ala
    130                 135                 140

Ala Gly Val Ser Ala Asp Lys Ala Val Leu Trp Glu Ser Ala Gly Glu
145                 150                 155                 160

Gly Glu Tyr Ser Val Ala Asp Ile Asp Lys Lys Glu Arg Gly Thr Glu
                165                 170                 175

Ile Thr Leu His Leu Arg Glu Asp Glu Lys Ala Phe Leu Asn Asp Trp
            180                 185                 190

Arg Leu Arg Glu Ile Ile Gly Lys Tyr Ser Asp His Ile Gly Leu Pro
        195                 200                 205
```

```
Val Glu Ile Leu Ala Lys Glu Tyr Asp Asp Glu Gly Lys Glu Thr Gly
    210                 215                 220
Ile Lys Trp Glu Lys Ile Asn Lys Ala Gln Ala Leu Trp Thr Arg Ala
225                 230                 235                 240
Lys Asn Glu Ile Ser Glu Glu Tyr Gln Glu Phe Tyr Lys His Leu
                245                 250                 255
Ser His Asp Phe Thr Asp Pro Leu Leu Trp Ala His Asn Lys Val Glu
            260                 265                 270
Gly Asn Gln Glu Tyr Thr Ser Leu Leu Tyr Val Pro Ala Lys Ala Pro
        275                 280                 285
Trp Asp Leu Phe Asn Arg Glu His Lys His Gly Leu Lys Leu Tyr Val
    290                 295                 300
Gln Arg Val Phe Ile Met Asp Asp Ala Gln Val Phe Met Pro Asn Tyr
305                 310                 315                 320
Leu Arg Phe Met Arg Gly Leu Leu Asp Ser Asn Asp Leu Pro Leu Asn
                325                 330                 335
Val Ser Arg Glu Ile Leu Gln Asp Asn Lys Val Thr Ser Ala Leu Arg
            340                 345                 350
Lys Ala Leu Thr Lys Arg Ala Leu Gln Met Leu Glu Lys Leu Ala Lys
        355                 360                 365
Asp Asp Ala Glu Lys Tyr Gln Arg Phe Trp Gln Glu Phe Gly Leu Val
370                 375                 380
Leu Lys Glu Gly Pro Ala Glu Asp Phe Ala Asn Lys Glu Thr Ile Ala
385                 390                 395                 400
Lys Leu Leu Arg Phe Ala Ser Thr His Asn Asp Ser Ser Gln Gln Ser
                405                 410                 415
Val Ser Leu Glu Asp Tyr Val Ala Arg Met Lys Glu Gly Gln Lys Ala
            420                 425                 430
Ile Tyr Tyr Ile Thr Ala Asp Thr Tyr Val Ala Ala Lys Asn Ser Pro
        435                 440                 445
His Leu Glu Leu Phe Asn Lys Lys Gly Ile Glu Val Leu Leu Leu Ser
    450                 455                 460
Asp Arg Ile Asp Glu Trp Met Leu Ser Tyr Leu Thr Glu Phe Asp Gly
465                 470                 475                 480
Lys Pro Leu Gln Thr Ile Ser Lys Ala Asp Leu Asp Leu Gly Asp Leu
                485                 490                 495
Ala Asp Lys Glu Glu Asp Ser Gln Lys Ala Gln Asp Glu Gln Tyr Ala
            500                 505                 510
Ser Phe Val Glu Arg Val Lys Thr Leu Leu Gly Glu Arg Val Lys Glu
        515                 520                 525
Val Arg Leu Thr His Arg Leu Thr Asp Thr Pro Ala Val Val Ser Thr
    530                 535                 540
Gly Asp Asp Gln Met Thr Thr Gln Met Ala Lys Leu Phe Ala Ala Ala
545                 550                 555                 560
Gly Gln Ala Met Pro Glu Val Lys Tyr Thr Phe Glu Leu Asn Pro Glu
                565                 570                 575
His Gly Leu Val Gln Lys Val Ala Glu Ile Ala Asp Glu Gln Gln Phe
            580                 585                 590
Ala Asp Trp Ile Glu Leu Leu Leu Glu Gln Ala Met Leu Ala Glu Arg
        595                 600                 605
Gly Ser Leu Glu Asn Pro Val Ala Phe Ile Lys Arg Met Asn Thr Leu
    610                 615                 620
```

Leu Ser Lys Leu Thr Ser His
625                 630

<210> SEQ ID NO 39
<211> LENGTH: 252
<212> TYPE: DNA
<213> ORGANISM: Pasteurella multocida

<400> SEQUENCE: 39
gagttggttc agaatatatt gctcagtatg gcaatgtgag tcttactata caaaatggta      60
aaattcatgg tgagatttat aggcataacc gagggtacga tgatctatttt aagctctctg    120 gagaaggccg gaatttaata ttaacgccac ataaaaataa ccctcatgat ctttccccaa    180
caggacccga caacatgaca atggagctga attttatcaa cgcagaaaag actgataaaa    240
aatacgttgt tc                                                        252

<210> SEQ ID NO 40
<211> LENGTH: 1008
<212> TYPE: DNA
<213> ORGANISM: Pasteurella multocida

<400> SEQUENCE: 40
atgaaacaaa tcgttttaaa aacaagctta ttgatgaccc tctcttcatt attagttgca      60
tgtagcggcg gtggcggtag cgctggaaat cgtgctgacc gtgtagagga aaaagcacaa    120
ccggttcaat caaatagtga gccttcttcc gctccaatca aaaatcctac taataccgct    180
acgaatgatt ctcttcatga caaactttca atgtcttctc atgacacatc caagaaaat    240 agtcaacaat cctcctttaa agcccctcta gaacaagaaa aaaaccaacc tgcacaagaa    300
aatctcactt ggacaggtta tcatgtttca gaagtgggaa atgcgagtaa taatgtagat    360
aaagataacg ttacggtatt cactttcgta aaatataatt ctcaatacaa tgatgatcca    420 gttttttgata aacaaaaac acaaagtaaa acaatatcat tagttgacgg aaaaaatgag    480
aataaagagg attattataa ctttacgtta aaagacgctt tattttatta tggaagttat    540
ggacaacctt cagcagatta caaaaaagta gaaaaaaatt atatttatgc aattaaacca    600
gatgcaataa ataatgagaa cctcaatgca ctaactgcaa cttattatca agaagatggt    660
tttatatatt ccgtattaag tgatgtaaat cgagttggtt cagaatatat tcctcagtat    720
ggcaatgtga ctcttacttt ccgaaatggc aagatttatg gtgaaatcta cagatataat    780
agaggacgtg atgatttgtt tcagctctca ggagaaggac aaaacttaac tataacacca    840
cacaaggaca atccccataa actatcccct acaggacccg acaacatggc aatggagctg    900
aattttatca cgcagaaaaa aactgataaa aaatacgttg ttggtgtagg aaaagctgaa    960
aaatattatg ggttattatt tgctgaaaaa agtcaccaag cacaataa                 1008

<210> SEQ ID NO 41
<211> LENGTH: 335
<212> TYPE: PRT
<213> ORGANISM: Pasteurella multocida

<400> SEQUENCE: 41

Met Lys Gln Ile Val Leu Lys Thr Ser Leu Leu Met Thr Leu Ser Ser
1               5                   10                  15

Leu Leu Val Ala Cys Ser Gly Gly Gly Ser Ala Gly Asn Arg Ala
            20                  25                  30

Asp Arg Val Glu Glu Lys Ala Gln Pro Val Gln Ser Asn Ser Glu Pro
        35                  40                  45

-continued

```
Ser Ser Ala Pro Ile Lys Asn Pro Thr Asn Thr Ala Thr Asn Asp Ser
    50                  55                  60

Leu His Asp Lys Leu Ser Met Ser Ser His Asp Thr Ser Lys Glu Asn
65                  70                  75                  80

Ser Gln Gln Ser Ser Phe Lys Ala Pro Leu Glu Gln Glu Lys Asn Gln
                85                  90                  95

Pro Ala Gln Glu Asn Leu Thr Trp Thr Gly Tyr His Val Ser Glu Val
            100                 105                 110

Gly Asn Ala Ser Asn Asn Val Asp Lys Asp Asn Val Thr Val Phe Thr
        115                 120                 125

Phe Val Lys Tyr Asn Ser Gln Tyr Asn Asp Asp Pro Val Phe Asp Lys
    130                 135                 140

Thr Lys Thr Gln Ser Lys Thr Ile Ser Leu Val Asp Gly Lys Asn Glu
145                 150                 155                 160

Asn Lys Glu Asp Tyr Tyr Asn Phe Thr Leu Lys Asp Ala Leu Phe Tyr
                165                 170                 175

Tyr Gly Ser Tyr Gly Gln Pro Ser Ala Asp Tyr Lys Lys Val Glu Lys
            180                 185                 190

Asn Tyr Ile Tyr Ala Ile Lys Pro Asp Ala Ile Asn Asn Glu Asn Leu
        195                 200                 205

Asn Ala Leu Thr Ala Thr Tyr Tyr Gln Glu Asp Gly Phe Ile Tyr Ser
    210                 215                 220

Val Leu Ser Asp Val Asn Arg Val Gly Ser Glu Tyr Ile Pro Gln Tyr
225                 230                 235                 240

Gly Asn Val Thr Leu Thr Phe Arg Asn Gly Lys Ile Tyr Gly Glu Ile
                245                 250                 255

Tyr Arg Tyr Asn Arg Gly Arg Asp Asp Leu Phe Gln Leu Ser Gly Glu
            260                 265                 270

Gly Gln Asn Leu Thr Ile Thr Pro His Lys Asp Asn Pro His Lys Leu
        275                 280                 285

Ser Pro Thr Gly Pro Asp Asn Met Ala Met Glu Leu Asn Phe Ile Asn
    290                 295                 300

Ala Glu Lys Thr Asp Lys Lys Tyr Val Val Gly Val Gly Lys Ala Glu
305                 310                 315                 320

Lys Tyr Tyr Gly Leu Leu Phe Ala Glu Lys Ser His Gln Ala Gln
                325                 330                 335
```

<210> SEQ ID NO 42
<211> LENGTH: 546
<212> TYPE: DNA
<213> ORGANISM: Pasteurella multocida
<220> FEATURE:
<221> NAME/KEY: modified_base
<222> LOCATION: (428)
<223> OTHER INFORMATION: a, t, c, g, other or unknown
<220> FEATURE:
<221> NAME/KEY: modified_base
<222> LOCATION: (470)
<223> OTHER INFORMATION: a, t, c, g, other or unknown
<220> FEATURE:
<221> NAME/KEY: modified_base
<222> LOCATION: (497)
<223> OTHER INFORMATION: a, t, c, g, other or unknown
<220> FEATURE:
<221> NAME/KEY: modified_base
<222> LOCATION: (499)
<223> OTHER INFORMATION: a, t, c, g, other or unknown
<220> FEATURE:
<221> NAME/KEY: modified_base
<222> LOCATION: (504)

```
<223> OTHER INFORMATION: a, t, c, g, other or unknown
<220> FEATURE:
<221> NAME/KEY: modified_base
<222> LOCATION: (507)
<223> OTHER INFORMATION: a, t, c, g, other or unknown
<220> FEATURE:
<221> NAME/KEY: modified_base
<222> LOCATION: (512)
<223> OTHER INFORMATION: a, t, c, g, other or unknown
<220> FEATURE:
<221> NAME/KEY: modified_base
<222> LOCATION: (519)
<223> OTHER INFORMATION: a, t, c, g, other or unknown

<400> SEQUENCE: 42
gcttggtatt tacagggaat ccaacctaat cccgttttta gacaggcttt taatgcaatt      60
actgatccca agaacaatt aattgcttta gaaggttttt ttaatttgat tctgatggat     120
aaagaaaaaa atgttagaac aacaacgtaa tcctgctgat gcactaactg tatcagtgtt    180
aaattcacaa tctcaagtca caaataaacc attgcgtgat tctgtgaaac aagcattgag    240
aaattatttg tcgcagttag atggccaaga tgtcaatgag ctttatgaat tagtattagc    300
agaagttgag catcctatgt tagatatggt tatgcaatat acacgtggaa atcaaactcg    360
tgcagcgaca atgttaggga ttaaccgtgg cactttacgt aagaaattaa aaaagtacgg    420
tatgggtnaa cggaccattg tagtatttaa actagttttg gttatagaan ggcggactta    480
ggtccgcctt tttaatntnc attnccnttt cnttttttcna aacaatgatt tttacgccct    540
caaatg                                                                546

<210> SEQ ID NO 43
<211> LENGTH: 1005
<212> TYPE: DNA
<213> ORGANISM: Pasteurella multocida

<400> SEQUENCE: 43
atgacagtgc ggataggttc ttatcagctt aaaaatcgca tttttcttgc tcctatggct      60
ggcatcactg accaaccatt tcggcgaatc tgcactcatt atggggcagg tttaactttt     120
tctgaaatga tgtcaacgaa tccgcaagtc tggcataccg aaaaatcgaa actgcgcttg     180
gctcatcatc aagaagcagg aattaatgct gtgcaaatag ctggttgtga tcccgatgag     240
atggcgaaag ctgctcaaat caatgtagaa tatggggcag aaattattga tatcaatatg     300
ggctgcccag ccaaaaaagt gaatcgtaaa atggcgggct ctgcgctgtt acaatatcct     360
gatttggtca aacaaattct taataaagtt gtgaaatctg ttactgtacc agtgacatta     420
aagataagaa caggctggga taaagacaac cgaaattgtt tagaaatcgc taaaattgca     480
gagcaatgtg gtattcaagc actgaccatc cacggacgaa caaggagttg tatgtttgag     540
ggggaggctg aatatgacaa tatcaaggcg gtcaaagagc aactttctat tccgattatt     600
gccaatggcg atattacttc cgctgaaaaa gcaaagtatg ttcttgatta taccaacgca     660
gatgcaataa tgatcggacg tggttcatta ggcaatccgt ggcttttccg agttatggaa     720
agcttaattg aaaaagactc gattgtttta gagccaagtt taaacgagaa atgtaatgtg     780
attttacagc atatccaaga actgcatcaa ttttatggtg tggagaaagg atgtcgtatt     840
gcacgtaaac acgttgcttg gtatttcag ggaatccaac ctaatcccgt ttttagacag    900
gcttttaatg caattactga tcccaaagaa caattaattg ctttagaagg ttttttttaat   960 ttgattctga tggataaaga aaaaaatgtt agaacaacaa cgtaa                     1005
```

<210> SEQ ID NO 44
<211> LENGTH: 334
<212> TYPE: PRT
<213> ORGANISM: Pasteurella multocida

<400> SEQUENCE: 44

Met Thr Val Arg Ile Gly Ser Tyr Gln Leu Lys Asn Arg Ile Phe Leu
1 5 10 15

Ala Pro Met Ala Gly Ile Thr Asp Gln Pro Phe Arg Arg Ile Cys Thr
20 25 30

His Tyr Gly Ala Gly Leu Thr Phe Ser Glu Met Met Ser Thr Asn Pro
35 40 45

Gln Val Trp His Thr Glu Lys Ser Lys Leu Arg Leu Ala His His Gln
50 55 60

Glu Ala Gly Ile Asn Ala Val Gln Ile Ala Gly Cys Asp Pro Asp Glu
65 70 75 80

Met Ala Lys Ala Ala Gln Ile Asn Val Glu Tyr Gly Ala Glu Ile Ile
85 90 95

Asp Ile Asn Met Gly Cys Pro Ala Lys Lys Val Asn Arg Lys Met Ala
100 105 110

Gly Ser Ala Leu Leu Gln Tyr Pro Asp Leu Val Lys Gln Ile Leu Asn
115 120 125

Lys Val Val Lys Ser Val Thr Val Pro Val Thr Leu Lys Ile Arg Thr
130 135 140

Gly Trp Asp Lys Asp Asn Arg Asn Cys Leu Glu Ile Ala Lys Ile Ala
145 150 155 160

Glu Gln Cys Gly Ile Gln Ala Leu Thr Ile His Gly Arg Thr Arg Ser
165 170 175

Cys Met Phe Glu Gly Glu Ala Glu Tyr Asp Asn Ile Lys Ala Val Lys
180 185 190

Glu Gln Leu Ser Ile Pro Ile Ile Ala Asn Gly Asp Ile Thr Ser Ala
195 200 205

Glu Lys Ala Lys Tyr Val Leu Asp Tyr Thr Asn Ala Asp Ala Ile Met
210 215 220

Ile Gly Arg Gly Ser Leu Gly Asn Pro Trp Leu Phe Arg Val Met Glu
225 230 235 240

Ser Leu Ile Glu Lys Asp Ser Ile Val Leu Glu Pro Ser Leu Asn Glu
245 250 255

Lys Cys Asn Val Ile Leu Gln His Ile Gln Glu Leu His Gln Phe Tyr
260 265 270

Gly Val Glu Lys Gly Cys Arg Ile Ala Arg Lys His Val Ala Trp Tyr
275 280 285

Leu Gln Gly Ile Gln Pro Asn Pro Val Phe Arg Gln Ala Phe Asn Ala
290 295 300

Ile Thr Asp Pro Lys Glu Gln Leu Ile Ala Leu Glu Gly Phe Phe Asn
305 310 315 320

Leu Ile Leu Met Asp Lys Glu Lys Asn Val Arg Thr Thr Thr
325 330

<210> SEQ ID NO 45
<211> LENGTH: 43
<212> TYPE: DNA
<213> ORGANISM: Pasteurella multocida

<400> SEQUENCE: 45
gcaaaatttt tggggatggt ctgatcctaa tgcaattcaa ata 43

<210> SEQ ID NO 46
<211> LENGTH: 1869
<212> TYPE: DNA
<213> ORGANISM: Pasteurella multocida

<400> SEQUENCE: 46

| | | | | | |
|---|---|---|---|---|---|
| atgaaaaagg | ttattatcat | tggacataaa | cagtctaact | atcaagatgt | tgaaaaggtt | 60 |
| tttcaatgtt | atgggatgaa | tcccccgctt | ccatcaaaac | gtgaaaaaat | gtccccatc | 120 |
| gaaattggcc | atgtacttaa | taagtatta | ccaagtcttg | agcacacacc | taaaaatgta | 180 |
| tctttacttt | ctaataagaa | aagcaaaata | aaaaaaggga | attcagccaa | aaataaatct | 240 |
| cataagcacg | ctaaaacgaa | cacaatacaa | acgacttcga | gcatctggga | taacttatct | 300 |
| ctcgatttga | tgctcgcgaa | tatcgagcaa | aattttggg | gatggtctga | tcctaatgca | 360 |
| attcaaatat | tagattattg | ggctaaccett | gacccaaaca | ttcatttcgt | ctttgtttat | 420 |
| gataagccag | aaaatttatt | ccaatatcat | agcttagaag | aggctctcaa | attagataaa | 480 |
| cacaccgtac | aagaaaaatt | tgaagagtgg | caaacctaca | atgaaaaaat | cctaacttac | 540 |
| tttaataaat | ataaagatcg | tagtgtatta | ctgaatacac | aacaactcca | aaatacgaaa | 600 |
| aaacatcac | tgtctgaaat | ttataaacat | atttctgcac | ctgatgcatt | agtcaaaaaa | 660 |
| ctgaatgaac | cttctctaaa | taagagatg | gaaattattg | aagtaaacca | agatttatct | 720 |
| caccaagaag | aatgtccact | gtctaacttt | attgttagcc | aaattataaa | aaattctcct | 780 |
| actgttacgc | aggtatatga | agaattacag | tcgcatgctg | atctgcctta | tatttcagaa | 840 |
| caaaaattag | taatgatgc | cgattttgct | ctccttgcat | ggaaagatat | gattcaaaaa | 900 |
| aaagtcgatg | taaatcaata | tcaacatgaa | aagaattag | aacttagcac | aataaaagaa | 960 |
| cgtcaattag | aggtcacaga | gagatatcaa | ttgacggaac | aaaaactgtc | agaaacacaa | 1020 |
| aaagaaatcg | aacaaattaa | agatgaaaat | agaaagtaa | aatctgaaaa | agcaaaactc | 1080 |
| actgcatctg | ttcaatcaac | gagcaaaata | ctttctgaga | agaaaaaga | gatttcttgc | 1140 |
| ataaaaagtg | aaaatacaaa | gattaaagaa | gaaaaaatta | aattgatga | agcataccac | 1200 |
| ttaaccaaga | aaaccttgtc | ggataaagaa | aaagccctca | aaacgcatca | agatgaaatt | 1260 |
| gaagcgctca | agataatttt | taatgaaaat | atttccgtac | aagaagatat | gcaagaaaaa | 1320 |
| tttcaggaag | ccaataaaag | aaaacaagaa | cttgaacaag | agctaaaagc | catatcggat | 1380 |
| aagaaagcat | tattagaaac | agaaacagc | caaaaaaccc | aagtatctga | gtctttagaa | 1440 |
| aatgaaaata | aagtgttatt | agctcaactc | caactcattc | aagaagaatt | agaaaaactt | 1500 |
| tatattgaca | atcaagtatt | aaaagctaaa | ccacgccttt | acggtgcagc | tgatcgcata | 1560 |
| aaaaaccaat | taacttatcg | actaggttac | aaaatacaaa | gacatggaag | aagtctatt | 1620 |
| ggtctcattt | tcttcctttt | catcttattt | ttcacctatc | tgggctttaa | aagagagatg | 1680 |
| aaaaagtacg | agtggaatac | gctcccacca | attcatgaat | atgaagatgc | gcatgaagcc | 1740 |
| aatcgcatta | aaagccattt | atcttataaa | ttgggcgtcc | tcttttgca | agaaatcaac | 1800 |
| aatccgttta | agtggcttac | tctcccttat | aaactgatta | agaaggtaa | acgattcaag | 1860 |
| caaggttaa | | | | | 1869 |

<210> SEQ ID NO 47
<211> LENGTH: 622
<212> TYPE: PRT
<213> ORGANISM: Pasteurella multocida

<400> SEQUENCE: 47

```
Met Lys Lys Val Ile Ile Ile Gly His Lys Gln Ser Asn Tyr Gln Asp
1               5                   10                  15

Val Glu Lys Val Phe Gln Cys Tyr Gly Met Asn Pro Pro Leu Pro Ser
            20                  25                  30

Lys Arg Glu Lys Met Ser Pro Ile Glu Ile Gly His Val Leu Asn Lys
        35                  40                  45

Val Leu Pro Ser Leu Glu His Thr Pro Lys Asn Val Ser Leu Leu Ser
    50                  55                  60

Asn Lys Lys Ser Lys Ile Lys Lys Gly Asn Ser Ala Lys Asn Lys Ser
65                  70                  75                  80

His Lys His Ala Lys Thr Asn Thr Ile Gln Thr Thr Ser Ser Ile Trp
                85                  90                  95

Asp Asn Leu Ser Leu Asp Leu Met Leu Ala Asn Ile Glu Gln Asn Phe
            100                 105                 110

Trp Gly Trp Ser Asp Pro Asn Ala Ile Gln Ile Leu Asp Tyr Trp Ala
        115                 120                 125

Asn Leu Asp Pro Asn Ile His Phe Val Phe Val Tyr Asp Lys Pro Glu
130                 135                 140

Asn Leu Phe Gln Tyr His Ser Leu Glu Glu Ala Leu Lys Leu Asp Lys
145                 150                 155                 160

His Thr Val Gln Glu Lys Phe Glu Glu Trp Gln Thr Tyr Asn Glu Lys
                165                 170                 175

Ile Leu Thr Tyr Phe Asn Lys Tyr Lys Asp Arg Ser Val Leu Leu Asn
            180                 185                 190

Thr Gln Gln Leu Gln Asn Thr Lys Lys Thr Ser Leu Ser Glu Ile Tyr
        195                 200                 205

Lys His Ile Ser Ala Pro Asp Ala Leu Val Lys Leu Asn Glu Pro
210                 215                 220

Ser Leu Asn Lys Glu Met Glu Ile Ile Glu Val Asn Gln Asp Leu Ser
225                 230                 235                 240

His Gln Glu Glu Cys Pro Leu Ser Asn Phe Ile Val Ser Gln Ile Ile
                245                 250                 255

Lys Asn Ser Pro Thr Val Thr Gln Val Tyr Glu Glu Leu Gln Ser His
            260                 265                 270

Ala Asp Leu Pro Tyr Ile Ser Glu Gln Lys Leu Val Asn Asp Ala Asp
        275                 280                 285

Phe Ala Leu Leu Ala Trp Lys Asp Met Ile Gln Lys Val Asp Val
290                 295                 300

Asn Gln Tyr Gln His Glu Lys Glu Leu Glu Leu Ser Thr Ile Lys Glu
305                 310                 315                 320

Arg Gln Leu Glu Val Thr Glu Arg Tyr Gln Leu Thr Glu Gln Lys Leu
                325                 330                 335

Ser Glu Thr Gln Lys Glu Ile Glu Gln Ile Lys Asp Glu Asn Arg Lys
            340                 345                 350

Val Lys Ser Glu Lys Ala Lys Leu Thr Ala Ser Val Gln Ser Thr Ser
        355                 360                 365

Lys Ile Leu Ser Glu Lys Glu Lys Ile Ser Cys Ile Lys Ser Glu
370                 375                 380

Asn Thr Lys Ile Lys Glu Glu Lys Ile Lys Ile Asp Glu Ala Tyr His
385                 390                 395                 400

Leu Thr Lys Lys Thr Leu Ser Asp Lys Glu Lys Ala Leu Lys Thr His
                405                 410                 415
```

```
Gln Asp Glu Ile Glu Ala Leu Lys Ile Ile Phe Asn Glu Asn Ile Ser
            420                 425                 430

Val Gln Glu Asp Met Gln Glu Lys Phe Gln Glu Ala Asn Lys Arg Lys
        435                 440                 445

Gln Glu Leu Glu Gln Glu Leu Lys Ala Ile Ser Asp Lys Lys Ala Leu
    450                 455                 460

Leu Glu Thr Glu Asn Ser Gln Lys Thr Gln Val Ser Glu Ser Leu Glu
465                 470                 475                 480

Asn Glu Asn Lys Val Leu Leu Ala Gln Leu Gln Leu Ile Gln Glu Glu
                485                 490                 495

Leu Glu Lys Leu Tyr Ile Asp Asn Gln Val Leu Lys Ala Lys Pro Arg
            500                 505                 510

Leu Tyr Gly Ala Ala Asp Arg Ile Lys Asn Gln Leu Thr Tyr Arg Leu
        515                 520                 525

Gly Tyr Lys Ile Gln Arg His Gly Arg Ser Leu Phe Gly Leu Ile Phe
    530                 535                 540

Leu Pro Phe Ile Leu Phe Phe Thr Tyr Leu Gly Phe Lys Arg Glu Met
545                 550                 555                 560

Lys Lys Tyr Glu Trp Asn Thr Leu Pro Pro Ile His Glu Tyr Glu Asp
                565                 570                 575

Ala His Glu Ala Asn Arg Ile Lys Ser His Leu Ser Tyr Lys Leu Gly
            580                 585                 590

Val Leu Phe Leu Gln Glu Ile Asn Asn Pro Phe Lys Trp Leu Thr Leu
        595                 600                 605

Pro Tyr Lys Leu Ile Lys Glu Gly Lys Arg Phe Lys Gln Gly
    610                 615                 620

<210> SEQ ID NO 48
<211> LENGTH: 279
<212> TYPE: DNA
<213> ORGANISM: Pasteurella multocida

<400> SEQUENCE: 48
accgcttcct gagctacgcc aaattctcac tgccttacca gtatccgcag aacaagcaga      60
aaatgatgat tacttaaccc attttaatcg cagccaagaa ttacttaatt ggcaacattt     120
ttttattgcc cagcaacttg ctttcgttaa cgcattggaa aatcaagaat gaaaaaatgg     180
ttgaaacatt tagatttgag cactggctta caactgtctt ttctgatcag tgggctactt     240
tgtctgtttg tcggtggcgt cgggctttat acttggcac                            279

<210> SEQ ID NO 49
<211> LENGTH: 1983
<212> TYPE: DNA
<213> ORGANISM: Pasteurella multocida

<400> SEQUENCE: 49
atgaaaaaat ggttgaaaca tttagatttg agcactggct acaactgtct tttctgatc       60 agtgggctac tttgtctgtt tgtcggtggc gtcgggcttt atacttggca gcaacaacgc    120
acggaaatca atttcgcact cgataaagat tttcctaaag tgcaagctgc gtttcaaaca    180
gaagaacaaa ttaatatcct ccatcatgcc tttatccatt ggtcaatgt caaaaacacc    240 aatgagaaag tcgaacgtta caaccatgca agcaacagc tttcgacgtt aaaagaactg    300
atcattgaat tagacgaaaa tttagatgag gatttgatgg cattattaca acaacaagcc    360
tcacttttag aacaaatatc acaaaatatc acaggtacgc ttacgttaaa cgatgaactg    420
```

-continued

```
aataaaacca tttctcaaat caactggtta cataatgatt ttcacaatga attcaccgca    480
cttttgcaag aaatgagctg gcaacaatct actctggcta acaatattgt tcaacagcca    540
cacaacaaac aaaaaatcga acaattaaaa aaactacaac aagaattatt gttagtttac    600
gatttcacta cttatgaaga gcaaattatc acggaattac gcacccagat aacagagcca    660
actgaaagca atgtcattcg actacacaat tatttgagct atttatcgtt attaattact    720
aaccgaattc agttgcttgg tcttcattcc tccacgtcaa ccattaaaca aattttagat    780
gaactgatta actttggctt aaacccacaa gcactccccg ccctatttgc aatccgtacc    840
gaactgaacc aacaacgaga acagctgatt caacaaagtg ataagatatt cgaggcattt    900
cgcgagcaaa tcagtactca aattggtaac agtaaacaac aattacattt actgcataat    960
attgtcgaaa aaagtactac attcaacggc gcattaattt tattggtgat gctatttgcg   1020
ggaatttttg tcatcggtat taacttcttt tatattcgtt tacgtctctt aaaacgtttt   1080
caacaactta accacgccgt agttcaatta accaatggcg agcccaacgt caaaatcgcc   1140
atttatggca atgatgaatt agggcggatt gctaaattat tgcgcttatt tctgttcgaa   1200
atgaatcaca aaacagaaga gttaaaatcg cgtaatcaag ttctcttaga ggaaatcgaa   1260
caccgtattg aagtacaaac cgcattagaa aatgcccaaa atgaactaac ccaagccgca   1320
aaactggctg ctgtcggtaa aaccttgact tcgattagcc atgaaattac acaaccactt   1380
aatgccatga acgcttattt gtttagtgcg aaaaaagccg tgagtaaaca aaacagtgag   1440
gcagcacttg aatacttaaa taaaatcaat catttagttg aacgcacggc gctgattgtc   1500
aaacgcttac ggcaattctc acgccaaggg agcggcaaaa tacaagctgt caatttaatg   1560
gattgtattc aaagcgcgtg ggaattattg gaatcacaac ataaaccgcg tcaaagtcag   1620
ctcatcacgc ccacagattt accactcgta ttaggtgaag atgtccttat cgaacaagtg   1680
tttgtcaatc tcttcctcaa tgctttagaa gccattgaac acacaccgcc ccaaattcat   1740
attgacgttg acagcgataa tgcggaagac ctctgtttat ggatcaccga caatggtcaa   1800
ggttggccct taactgacaa gttattgcaa cctttttcga gcagtaaatc gatcaattta   1860
ggtttaggac tgtccattag tcaatccatc atggagcaat gtcaaggatc attgaccatt   1920
gcctctactc tcacccataa tgcattagtg atattaaaat ttaaggtggc tcaacatgtt   1980
taa                                                                 1983
```

<210> SEQ ID NO 50
<211> LENGTH: 660
<212> TYPE: PRT
<213> ORGANISM: Pasteurella multocida

<400> SEQUENCE: 50

```
Met Lys Lys Trp Leu Lys His Leu Asp Leu Ser Thr Gly Leu Gln Leu
1               5                   10                  15

Ser Phe Leu Ile Ser Gly Leu Leu Cys Leu Phe Val Gly Gly Val Gly
            20                  25                  30

Leu Tyr Thr Trp Gln Gln Gln Arg Thr Glu Ile Asn Phe Ala Leu Asp
        35                  40                  45

Lys Asp Phe Pro Lys Val Gln Ala Ala Phe Gln Thr Glu Glu Gln Ile
    50                  55                  60

Asn Ile Leu His His Ala Phe Ile His Leu Val Asn Val Lys Asn Thr
65                  70                  75                  80

Asn Glu Lys Val Glu Arg Tyr Asn His Ala Lys Gln Gln Leu Ser Thr
```

-continued

```
                85                  90                  95
Leu Lys Glu Leu Ile Ile Glu Leu Asp Glu Asn Leu Asp Glu Asp Leu
            100                 105                 110

Met Ala Leu Leu Gln Gln Ala Ser Leu Leu Glu Gln Ile Ser Gln
            115                 120                 125

Asn Ile Thr Gly Thr Leu Thr Leu Asn Asp Glu Leu Asn Lys Thr Ile
130             135                 140

Ser Gln Ile Asn Trp Leu His Asn Asp Phe His Asn Glu Phe Thr Ala
145                 150                 155                 160

Leu Leu Gln Glu Met Ser Trp Gln Gln Ser Thr Leu Ala Asn Asn Ile
            165                 170                 175

Val Gln Gln Pro His Asn Lys Gln Lys Ile Glu Gln Leu Lys Lys Leu
            180                 185                 190

Gln Gln Glu Leu Leu Leu Val Tyr Asp Phe Thr Thr Tyr Glu Glu Gln
            195                 200                 205

Ile Ile Thr Glu Leu Arg Thr Gln Ile Thr Glu Pro Thr Glu Ser Asn
            210                 215                 220

Val Ile Arg Leu His Asn Tyr Leu Ser Tyr Leu Ser Leu Leu Ile Thr
225                 230                 235                 240

Asn Arg Ile Gln Leu Leu Gly Leu His Ser Ser Thr Ser Thr Ile Lys
            245                 250                 255

Gln Ile Leu Asp Glu Leu Ile Asn Phe Gly Leu Asn Pro Gln Ala Leu
            260                 265                 270

Pro Ala Leu Phe Ala Ile Arg Thr Glu Leu Asn Gln Gln Arg Glu Gln
            275                 280                 285

Leu Ile Gln Gln Ser Asp Lys Ile Phe Glu Ala Phe Arg Glu Gln Ile
            290                 295                 300

Ser Thr Gln Ile Gly Asn Ser Lys Gln Gln Leu His Leu Leu His Asn
305                 310                 315                 320

Ile Val Glu Lys Ser Thr Thr Phe Asn Gly Ala Leu Ile Leu Leu Val
            325                 330                 335

Met Leu Phe Ala Gly Ile Phe Val Ile Gly Ile Asn Phe Phe Tyr Ile
            340                 345                 350

Arg Leu Arg Leu Leu Lys Arg Phe Gln Gln Leu Asn His Ala Val Val
            355                 360                 365

Gln Leu Thr Asn Gly Glu Pro Asn Val Lys Ile Ala Ile Tyr Gly Asn
            370                 375                 380

Asp Glu Leu Gly Arg Ile Ala Lys Leu Leu Arg Leu Phe Leu Phe Glu
385                 390                 395                 400

Met Asn His Lys Thr Glu Glu Leu Lys Ser Arg Asn Gln Val Leu Leu
            405                 410                 415

Glu Glu Ile Glu His Arg Ile Glu Val Gln Thr Ala Leu Glu Asn Ala
            420                 425                 430

Gln Asn Glu Leu Thr Gln Ala Ala Lys Leu Ala Ala Val Gly Lys Thr
            435                 440                 445

Leu Thr Ser Ile Ser His Glu Ile Thr Gln Pro Leu Asn Ala Met Asn
            450                 455                 460

Ala Tyr Leu Phe Ser Ala Lys Lys Ala Val Ser Lys Gln Asn Ser Glu
465                 470                 475                 480

Ala Ala Leu Glu Tyr Leu Asn Lys Ile Asn His Leu Val Glu Arg Thr
            485                 490                 495

Ala Leu Ile Val Lys Arg Leu Arg Gln Phe Ser Arg Gln Gly Ser Gly
            500                 505                 510
```

Lys Ile Gln Ala Val Asn Leu Met Asp Cys Ile Gln Ser Ala Trp Glu
            515                 520                 525

Leu Leu Glu Ser Gln His Lys Pro Arg Gln Ser Gln Leu Ile Thr Pro
        530                 535                 540

Thr Asp Leu Pro Leu Val Leu Gly Glu Asp Val Leu Ile Glu Gln Val
545                 550                 555                 560

Phe Val Asn Leu Phe Leu Asn Ala Leu Glu Ala Ile Glu His Thr Pro
                565                 570                 575

Pro Gln Ile His Ile Asp Val Asp Ser Asp Asn Ala Glu Asp Leu Cys
            580                 585                 590

Leu Trp Ile Thr Asp Asn Gly Gln Gly Trp Pro Leu Thr Asp Lys Leu
        595                 600                 605

Leu Gln Pro Phe Ser Ser Ser Lys Ser Ile Asn Leu Gly Leu Gly Leu
    610                 615                 620

Ser Ile Ser Gln Ser Ile Met Glu Gln Cys Gln Gly Ser Leu Thr Ile
625                 630                 635                 640

Ala Ser Thr Leu Thr His Asn Ala Leu Val Ile Leu Lys Phe Lys Val
                645                 650                 655

Ala Gln His Val
            660

<210> SEQ ID NO 51
<211> LENGTH: 93
<212> TYPE: DNA
<213> ORGANISM: Pasteurella multocida

<400> SEQUENCE: 51
atagaaatgg tttatttcca aatttcctca aatttcacct tggctttta gaattttggc      60 gttgccacta aattacagta gctgttttgt gct                                  93

<210> SEQ ID NO 52
<211> LENGTH: 525
<212> TYPE: DNA
<213> ORGANISM: Pasteurella multocida

<400> SEQUENCE: 52
atgacacaac aagcgatctt tgccggcggc tgttttttggt gcgttgaggc agtatttaat    60
caaattaaag gcgttgaaaa agcgacttca ggttatatta cgggacgac tgaaaatcca     120 acttacaaag aagtatgtac cggtgaaacg ggtcatgcgg aagcggtaaa agtggaattc    180
gatgcgacag tgattagtta tgaaaaatta ttagacatct tcttttctat ccataatcca    240
acccaattaa atcaccaggg cgaagatgtg gaacgcaat atcgcacagg gatttactat    300
ttaaatgatg aacaagaaca gctggcaaat aagaaaattg cagaattaca accgcacttt    360
gccgaaaaaa ttgtcactga agtgctgcca gcacaaactt ttatcccgc agaagattat    420 caccaaggct atttattgca gaacccacaa acagcactact gtaatttagt ggcaacgcca   480
aaattcttaa agccaaggt gaatttgag gaaatttgga agtaa                      525

<210> SEQ ID NO 53
<211> LENGTH: 174
<212> TYPE: PRT
<213> ORGANISM: Pasteurella multocida

<400> SEQUENCE: 53

Met Thr Gln Gln Ala Ile Phe Ala Gly Gly Cys Phe Trp Cys Val Glu
1               5                   10                  15

-continued

```
Ala Val Phe Asn Gln Ile Lys Gly Val Glu Lys Ala Thr Ser Gly Tyr
            20                  25                  30
Ile Asn Gly Thr Thr Glu Asn Pro Thr Tyr Lys Glu Val Cys Thr Gly
        35                  40                  45
Glu Thr Gly His Ala Glu Ala Val Lys Val Glu Phe Asp Ala Thr Val
    50                  55                  60
Ile Ser Tyr Glu Lys Leu Leu Asp Ile Phe Phe Ser Ile His Asn Pro
65                  70                  75                  80
Thr Gln Leu Asn His Gln Gly Glu Asp Val Gly Thr Gln Tyr Arg Thr
                85                  90                  95
Gly Ile Tyr Tyr Leu Asn Asp Glu Gln Glu Gln Leu Ala Asn Lys Lys
            100                 105                 110
Ile Ala Glu Leu Gln Pro His Phe Ala Glu Lys Ile Val Thr Glu Val
        115                 120                 125
Leu Pro Ala Gln Thr Phe Tyr Pro Ala Glu Asp Tyr His Gln Gly Tyr
    130                 135                 140
Leu Leu Gln Asn Pro Gln Asn Ser Tyr Cys Asn Leu Val Ala Thr Pro
145                 150                 155                 160
Lys Phe Leu Lys Ala Lys Val Lys Phe Glu Glu Ile Trp Lys
                165                 170
```

<210> SEQ ID NO 54
<211> LENGTH: 772
<212> TYPE: DNA
<213> ORGANISM: Pasteurella multocida
<220> FEATURE:
<221> NAME/KEY: modified_base
<222> LOCATION: (537)
<223> OTHER INFORMATION: a, t, c, g, other or unknown
<220> FEATURE:
<221> NAME/KEY: modified_base
<222> LOCATION: (540)
<223> OTHER INFORMATION: a, t, c, g, other or unknown
<220> FEATURE:
<221> NAME/KEY: modified_base
<222> LOCATION: (545)
<223> OTHER INFORMATION: a, t, c, g, other or unknown
<220> FEATURE:
<221> NAME/KEY: modified_base
<222> LOCATION: (581)
<223> OTHER INFORMATION: a, t, c, g, other or unknown
<220> FEATURE:
<221> NAME/KEY: modified_base
<222> LOCATION: (613)..(614)
<223> OTHER INFORMATION: a, t, c, g, other or unknown
<220> FEATURE:
<221> NAME/KEY: modified_base
<222> LOCATION: (665)
<223> OTHER INFORMATION: a, t, c, g, other or unknown
<220> FEATURE:
<221> NAME/KEY: modified_base
<222> LOCATION: (668)
<223> OTHER INFORMATION: a, t, c, g, other or unknown
<220> FEATURE:
<221> NAME/KEY: modified_base
<222> LOCATION: (685)..(686)
<223> OTHER INFORMATION: a, t, c, g, other or unknown
<220> FEATURE:
<221> NAME/KEY: modified_base
<222> LOCATION: (700)..(704)
<223> OTHER INFORMATION: a, t, c, g, other or unknown
<220> FEATURE:
<221> NAME/KEY: modified_base
<222> LOCATION: (721)..(723)
<223> OTHER INFORMATION: a, t, c, g, other or unknown
<220> FEATURE:
<221> NAME/KEY: modified_base
<222> LOCATION: (732)
<223> OTHER INFORMATION: a, t, c, g, other or unknown
<220> FEATURE:
<221> NAME/KEY: modified_base
<222> LOCATION: (734)
<223> OTHER INFORMATION: a, t, c, g, other or unknown
<220> FEATURE:
<221> NAME/KEY: modified_base
<222> LOCATION: (737).(738)
<223> OTHER INFORMATION: a, t, c, g, other or unknown
<220> FEATURE:

<220> FEATURE:
<221> NAME/KEY: modified_base
<222> LOCATION: (748)
<223> OTHER INFORMATION: a, t, c, g, other or unknown
<220> FEATURE:
<221> NAME/KEY: modified_base
<222> LOCATION: (752)
<223> OTHER INFORMATION: a, t, c, g, other or unknown
<220> FEATURE:
<221> NAME/KEY: modified_base
<222> LOCATION: (755)
<223> OTHER INFORMATION: a, t, c, g, other or unknown
<220> FEATURE:
<221> NAME/KEY: modified_base
<222> LOCATION: (770)..(772)
<223> OTHER INFORMATION: a, t, c, g, other or unknown

<400> SEQUENCE: 54

| | | | | | |
|---|---|---|---|---|---|
| gcataggtat | cctttgcttg | acataaaatg | actacaggct | aaagcacagg | atattaaaag | 60 |
| ggcaaaagaa | taagttactt | ttgcgacacg | catcgcaaaa | gtaaaataaa | tttagtcaat | 120 |
| caatttagct | tgttttaaga | aatactcaat | gccatgttct | ttgatcggta | aggtgacatg | 180 |
| atcggctact | gttttagct | gatgatgtgc | attccccatt | gcaacaccca | ctcctgccgt | 240 |
| gcttaacatt | tcaatatcat | tcaagccatc | accaaatgcc | atcacatttt | ccattgcaaa | 300 |
| gccaaaatgt | tgaattgcac | aagcgatacc | cgtagctttt | gagattttt | catcaaataa | 360 |
| atcaaccgag | tatttatgcc | agcgtaccga | ttgtaatcct | ttcagtacac | cagaatcttg | 420 |
| gacaaattga | tcttgcgtag | catcataaaa | agccagtatc | tgaaaacat | catgactgtt | 480 |
| taaaatagtc | tttatctaca | tgataatgcc | cttttagcgg | atccaatgca | tcacganctn | 540 |
| gatcngttat | cgctgaaact | gcggtatctg | tcggtgacac | ntgcgcataa | caatctgatg | 600 |
| ttgatcacaa | aannacgaac | tctggatttt | gcttagataa | ggatctccga | tggctatcta | 660 |
| tactnatntg | acatcatgta | cacanncatg | tcgtgccatn | nnnacttag | cgaagtgcag | 720 |
| nnnccgtcat | cngncannca | gacatcantc | cnacntgcta | ttaggataan | nn | 772 |

<210> SEQ ID NO 55
<211> LENGTH: 687
<212> TYPE: DNA
<213> ORGANISM: Pasteurella multocida

<400> SEQUENCE: 55

| | | | | | |
|---|---|---|---|---|---|
| atgcgggat | ttggttttg | ttgtgttcac | tgccagcaac | cgttagccat | tgcacatcat | 60 |
| ggattatgta | gtcgctgtaa | tcagcaaatc | agacgttttg | cttattgtgg | ccattgtggt | 120 |
| aaggaattaa | cacgagatgc | actacgttgt | gggcattgtt | tacaacataa | agccagttgg | 180 |
| gatcgcatgg | tgatcgttgg | tcactatgtc | gatcccttat | cttgtttaat | tcaccgtttt | 240 |
| aaattccaac | atgccttctt | tttagaccgt | actttagcac | gcctgctatt | attagcgctc | 300 |
| tatcatgcaa | gacgtactca | tggacttatt | tggccagaag | tacttttgcc | ggtgccttta | 360 |
| catcgtttac | gtcattggca | acgtggttac | aatcaatctg | cgttgattgc | aaactatctt | 420 |
| gcgcattggc | taaagatacc | ctgcgatcat | gattttctac | agcgtattaa | acatactcat | 480 |
| acgcaacgtg | gtttaagtgc | aacggaacga | agaaaaaatt | tacgccacgc | atttcgtctt | 540 |
| catccaaaaa | gtcaaacgca | tcgctatcaa | tctgttgcat | taattgatga | tgtaattaca | 600 |
| acaggtgcaa | cgttgaatga | gttggcactc | ttattaaaaa | aagcaggtgt | tgagcatatt | 660 |
| caagtttggg | gattagcaaa | aacgtaa | | | | 687 |

<210> SEQ ID NO 56
<211> LENGTH: 228

-continued

<212> TYPE: PRT
<213> ORGANISM: Pasteurella multocida

<400> SEQUENCE: 56

Met Arg Gly Phe Gly Phe Cys Cys Val His Cys Gln Gln Pro Leu Ala
1               5                   10                  15

Ile Ala His His Gly Leu Cys Ser Arg Cys Asn Gln Gln Ile Arg Arg
            20                  25                  30

Phe Ala Tyr Cys Gly His Cys Gly Lys Glu Leu Thr Arg Asp Ala Leu
        35                  40                  45

Arg Cys Gly His Cys Leu Gln His Lys Ala Ser Trp Asp Arg Met Val
    50                  55                  60

Ile Val Gly His Tyr Val Asp Pro Leu Ser Cys Leu Ile His Arg Phe
65                  70                  75                  80

Lys Phe Gln His Ala Phe Phe Leu Asp Arg Thr Leu Ala Arg Leu Leu
                85                  90                  95

Leu Leu Ala Leu Tyr His Ala Arg Arg Thr His Gly Leu Ile Trp Pro
            100                 105                 110

Glu Val Leu Leu Pro Val Pro Leu His Arg Leu Arg His Trp Gln Arg
        115                 120                 125

Gly Tyr Asn Gln Ser Ala Leu Ile Ala Asn Tyr Leu Ala His Trp Leu
    130                 135                 140

Lys Ile Pro Cys Asp His Asp Phe Leu Gln Arg Ile Lys His Thr His
145                 150                 155                 160

Thr Gln Arg Gly Leu Ser Ala Thr Glu Arg Arg Lys Asn Leu Arg His
                165                 170                 175

Ala Phe Arg Leu His Pro Lys Ser Gln Thr His Arg Tyr Gln Ser Val
            180                 185                 190

Ala Leu Ile Asp Asp Val Ile Thr Thr Gly Ala Thr Leu Asn Glu Leu
        195                 200                 205

Ala Leu Leu Leu Lys Lys Ala Gly Val Glu His Ile Gln Val Trp Gly
    210                 215                 220

Leu Ala Lys Thr
225

<210> SEQ ID NO 57
<211> LENGTH: 700
<212> TYPE: DNA
<213> ORGANISM: Pasteurella multocida
<220> FEATURE:
<221> NAME/KEY: modified_base
<222> LOCATION: (498)
<223> OTHER INFORMATION: a, t, c, g, other or unknown
<220> FEATURE:
<221> NAME/KEY: modified_base
<222> LOCATION: (540)
<223> OTHER INFORMATION: a, t, c, g, other or unknown
<220> FEATURE:
<221> NAME/KEY: modified_base
<222> LOCATION: (562)
<223> OTHER INFORMATION: a, t, c, g, other or unknown
<220> FEATURE:
<221> NAME/KEY: modified_base
<222> LOCATION: (565)
<223> OTHER INFORMATION: a, t, c, g, other or unknown
<220> FEATURE:
<221> NAME/KEY: modified_base
<222> LOCATION: (572)..(573)
<223> OTHER INFORMATION: a, t, c, g, other or unknown
<220> FEATURE:
<221> NAME/KEY: modified_base
<222> LOCATION: (577)
<223> OTHER INFORMATION: a, t, c, g, other or unknown

```
<220> FEATURE:
<221> NAME/KEY: modified_base
<222> LOCATION: (584)
<223> OTHER INFORMATION: a, t, c, g, other or unknown
<220> FEATURE:
<221> NAME/KEY: modified_base
<222> LOCATION: (587)..(588)
<223> OTHER INFORMATION: a, t, c, g, other or unknown
<220> FEATURE:
<221> NAME/KEY: modified_base
<222> LOCATION: (591)..(592)
<223> OTHER INFORMATION: a, t, c, g, other or unknown
<220> FEATURE:
<221> NAME/KEY: modified_base
<222> LOCATION: (594)..(595)
<223> OTHER INFORMATION: a, t, c, g, other or unknown
<220> FEATURE:
<221> NAME/KEY: modified_base
<222> LOCATION: (599)
<223> OTHER INFORMATION: a, t, c, g, other or unknown
<220> FEATURE:
<221> NAME/KEY: modified_base
<222> LOCATION: (604)
<223> OTHER INFORMATION: a, t, c, g, other or unknown
<220> FEATURE:
<221> NAME/KEY: modified_base
<222> LOCATION: (619)
<223> OTHER INFORMATION: a, t, c, g, other or unknown
<220> FEATURE:
<221> NAME/KEY: modified_base
<222> LOCATION: (623)
<223> OTHER INFORMATION: a, t, c, g, other or unknown
<220> FEATURE:
<221> NAME/KEY: modified_base
<222> LOCATION: (625)
<223> OTHER INFORMATION: a, t, c, g, other or unknown
<220> FEATURE:
<221> NAME/KEY: modified_base
<222> LOCATION: (627)
<223> OTHER INFORMATION: a, t, c, g, other or unknown
<220> FEATURE:
<221> NAME/KEY: modified_base
<222> LOCATION: (633)
<223> OTHER INFORMATION: a, t, c, g, other or unknown
<220> FEATURE:
<221> NAME/KEY: modified_base
<222> LOCATION: (638)
<223> OTHER INFORMATION: a, t, c, g, other or unknown
<220> FEATURE:
<221> NAME/KEY: modified_base
<222> LOCATION: (644)..(645)
<223> OTHER INFORMATION: a, t, c, g, other or unknown
<220> FEATURE:
<221> NAME/KEY: modified_base
<222> LOCATION: (653)
<223> OTHER INFORMATION: a, t, c, g, other or unknown
<220> FEATURE:
<221> NAME/KEY: modified_base
<222> LOCATION: (657)
<223> OTHER INFORMATION: a, t, c, g, other or unknown
<220> FEATURE:
<221> NAME/KEY: modified_base
<222> LOCATION: (661)
<223> OTHER INFORMATION: a, t, c, g, other or unknown
<220> FEATURE:
<221> NAME/KEY: modified_base
<222> LOCATION: (664)
<223> OTHER INFORMATION: a, t, c, g, other or unknown
<220> FEATURE:
<221> NAME/KEY: modified_base
<222> LOCATION: (666)
<223> OTHER INFORMATION: a, t, c, g, other or unknown
<220> FEATURE:
<221> NAME/KEY: modified_base
<222> LOCATION: (671)
<223> OTHER INFORMATION: a, t, c, g, other or unknown
<220> FEATURE:
<221> NAME/KEY: modified_base
<222> LOCATION: (673)..(674)
```

<223> OTHER INFORMATION: a, t, c, g, other or unknown
<220> FEATURE:
<221> NAME/KEY: modified_base
<222> LOCATION: (678)
<223> OTHER INFORMATION: a, t, c, g, other or unknown
<220> FEATURE:
<221> NAME/KEY: modified_base
<222> LOCATION: (682)
<223> OTHER INFORMATION: a, t, c, g, other or unknown
<220> FEATURE:
<221> NAME/KEY: modified_base
<222> LOCATION: (686)..(687)
<223> OTHER INFORMATION: a, t, c, g, other or unknown
<220> FEATURE:
<221> NAME/KEY: modified_base
<222> LOCATION: (694)
<223> OTHER INFORMATION: a, t, c, g, other or unknown
<220> FEATURE:
<221> NAME/KEY: modified_base
<222> LOCATION: (696)..(697)
<223> OTHER INFORMATION: a, t, c, g, other or unknown
<220> FEATURE:
<221> NAME/KEY: modified_base
<222> LOCATION: (699)..(700)
<223> OTHER INFORMATION: a, t, c, g, other or unknown

<400> SEQUENCE: 57

```
tgccgaccac tccaaaggac aaaaaatgag cctatttgcg attttctatc tgttcctggc      60
gtatttatta ggatctgttt ctagtgcaat tttattgtgt cgtttagcgg ggttgcctga     120
tcctagagaa agtggttctc ataatcccgg tgcaaccaat gtattgcgta ttggtgggcg     180
ttgggtggca ttgagtgtac tcctgtttga tatgctcaaa ggtatgttac ctgtttggtt     240
aggctattat cttggtttga ctcatttga gttagggatg gtggcattag gtgcttgttt      300
agggcacatt ttcccaatct tctttaaatt taaaggcgga aaaggggtag caacggcatt     360
tggtgctatt gcgccgattt catggggtgt cgcaggcagt atgctgggca cttggttatt     420
gattttcttc gtgagtggtt attcttcgct cagtgcagtg atgaccgcgc ttctggtacc     480
tttctatgtg tggtggtnta agcccgagtt tactttccct gtcgcttagt gtgttgcttn     540
tcgattatcg ccatcatgac anatncagcg tnngtgngtg ggcnagnnga nnanngtgna     600
atanactgaa acaaaaaang atnantnagc tanttacnaa aaanngacag acngtcnttt     660
natncncgtt nanntatnga cntatnngat ggcntnncnn                           700
```

<210> SEQ ID NO 58
<211> LENGTH: 606
<212> TYPE: DNA
<213> ORGANISM: Pasteurella multocida

<400> SEQUENCE: 58

```
atgagcctat ttgcgatttt ctatctgttc ctggcgtatt tattaggatc tgtttctagt      60
gcaatttat tgtgtcgttt agcggggttg cctgatccaa gagaaagtgg ttctcataat     120
cccggtgcaa ccaatgtctt gcgtattggt gggcgttggg tggcattgag tgtactcctg     180
tttgatatgc ttaaaggtat gttacctgtt tggttaggct attatcttgg tttgactcat     240
tttgaattag ggatggtggc attaggtgct tgtttagggc acatttttcc aatcttcttt     300
aaatttaaag gcggaaaagg ggtggcaacg gcatttggtg ctattgcgcc gatctcatgg     360
ggtgtcgctg gcagtatgct aggcacttgg ttattgattt tcttcgtgag tggttattct     420
tcgctcagtg cggtgatgac cgcgcttctg gtaccttct atgtgtggtg gtttaagccc     480
gagtttactt ccctgtcgc tttagtgtgt gcttgttga tttatcgcca tcatgacaat     540
attcagcgtt tgtggcgtgg gcaagaagac aaagtgtgga ataaactgaa aacaaaaaa     600
```

-continued

```
gattaa                                                             606

<210> SEQ ID NO 59
<211> LENGTH: 201
<212> TYPE: PRT
<213> ORGANISM: Pasteurella multocida

<400> SEQUENCE: 59

Met Ser Leu Phe Ala Ile Phe Tyr Leu Phe Leu Ala Tyr Leu Leu Gly
1               5                   10                  15

Ser Val Ser Ser Ala Ile Leu Leu Cys Arg Leu Ala Gly Leu Pro Asp
            20                  25                  30

Pro Arg Glu Ser Gly Ser His Asn Pro Gly Ala Thr Asn Val Leu Arg
        35                  40                  45

Ile Gly Gly Arg Trp Val Ala Leu Ser Val Leu Leu Phe Asp Met Leu
    50                  55                  60

Lys Gly Met Leu Pro Val Trp Leu Gly Tyr Tyr Leu Gly Leu Thr His
65                  70                  75                  80

Phe Glu Leu Gly Met Val Ala Leu Gly Ala Cys Leu Gly His Ile Phe
                85                  90                  95

Pro Ile Phe Phe Lys Phe Lys Gly Gly Lys Gly Val Ala Thr Ala Phe
            100                 105                 110

Gly Ala Ile Ala Pro Ile Ser Trp Gly Val Ala Gly Ser Met Leu Gly
        115                 120                 125

Thr Trp Leu Leu Ile Phe Phe Val Ser Gly Tyr Ser Ser Leu Ser Ala
    130                 135                 140

Val Met Thr Ala Leu Leu Val Pro Phe Tyr Val Trp Trp Phe Lys Pro
145                 150                 155                 160

Glu Phe Thr Phe Pro Val Ala Leu Val Cys Cys Leu Leu Ile Tyr Arg
                165                 170                 175

His His Asp Asn Ile Gln Arg Leu Trp Arg Gly Gln Glu Asp Lys Val
            180                 185                 190

Trp Asn Lys Leu Lys Asn Lys Lys Asp
        195                 200

<210> SEQ ID NO 60
<211> LENGTH: 188
<212> TYPE: DNA
<213> ORGANISM: Pasteurella multocida

<400> SEQUENCE: 60
atcccaccga taaaaccaaa tggattacgc gcagtttcca aataaacagg ggtagcacca     60
gcttgaatta atgcaccatg atggatagat ttgtgattgt tacgatcaaa gagcacaaga    120
tcacccggtg tgagtaacgc attggtgacg actttatttg cagaagatgt cccatttaag    180
acgaagta                                                             188

<210> SEQ ID NO 61
<211> LENGTH: 2163
<212> TYPE: DNA
<213> ORGANISM: Pasteurella multocida

<400> SEQUENCE: 61
atgctaaatt taaaaattgc atatagccca ttaattcgac cttattttca tacaaataga     60
gaactcgttt ctgttcaaga aacagatttc accgacattg gtgcaattat cctgagttct    120
gaagatattg aagattatat tgatagtata caagcaactg aatttaatat tccggtcttt    180
```

```
gttgctgtca ttgaaggtca attttagat cctcaattct ttgacaaagt ctatcacgtt      240
caagatctca caactacga catcaaccta tacagtcgcc aaattgaaac tgcggcgcgg      300
ttttacgaag aaaaaatcct cccacctttc tttaaaatgc taagtgaata tgtggaaatg      360
gggaattctg cttttgattg tccgggacac caaggtggac aatatttccg taaacatcct      420
gcaggacgtt atctctatga tttctacggt gaaaatattt tccgctcaga tatctgtaat      480
gccgatgtaa aattaggcga tttgctaatc catgaaggag ccgcttgtga tgctcaaaaa      540
cacgctgctc aagtctttaa tgctgataaa acctacttcg tcttaaatgg acatcttct       600 gcaaataaag tcgtcaccaa tgcgttactc acaccgggtg atcttgtgct ctttgatcgt      660
aacaatcaca atctatcca tcacggtgca ttaattcaag ctggtgctac ccctgtttat       720
ttggaaactg cgcgtaatcc atttggtttt atcggtggga tcgatagcca ttgttttgat      780
gaagattatt tgaaatcttt aattaaagat gttgcgcctg aaaaactaac acaagcacgt      840
cctttccgtt tagccgttat tcagctcggc acttatgacg gaaccatcta taatgcgcgc      900
caagtcgtag ataaaattgg tcatttatgt gactacatct tgtttgattc tgcgtgggta      960
ggttatgaac aattcattcc aatgatgaaa gattgctcac cgctcttgct tgaattaaat     1020
gaaaatgatc ccggcatcat cgtgacacaa tcagtacaca acaacaagc cggcttctca     1080 caagcctcac aaattcacaa aaaagacaag cacattaaag gtcaacagcg ctactgtaat     1140
cataaacgct ttaataatgc attcatgtta cacgcctcca ccagcccatt ctaccctctt     1200
tttgccacac ttgatgtcaa tgcaaaaatt caaggtaccc ctgcgggtat tcgtttatgg     1260
catgactgtg tcaaaatcgg gatagaagca cgtaaaatgg tgctgaatag ttgtgatctg     1320
atcaaaccgt ttattccgcc ttatgtcaat ggcaaaaaat ggcaagacta cgatacagaa     1380
gaaatggcaa atgatttaac attcttcaaa ttccatgctg atgataaatg gcatcaattt     1440
gaaggctatg tagataacca atattttgtt gatccatgta aattcatgct aacgacgccg     1500
ggtattgata ttgaaacagg tgaatacgaa gacttcggtg tccctgctac gattcttgct     1560
aattatttac gtgaaaacgg cattattccg gaaaaatgtg acttaaactc aattctcttc     1620
ttattaacgc cagcagaaac cctcaccaaa atgcaaagtt tggttgcaca aattgcggca     1680
tttgaacaac acatcaaaaa agattcctta ctaaaagaag tcttaccaag tgtttatcac     1740
aacaatgaaa aacgctatga aggttatacc atccgtcgtc tttgccaaga aatgcatgat     1800
ttgtatgtca gccgtaacgt gaaaacttta caacgcaact tattcagaaa agcgaccttg     1860
cctgaatatg tgatgaatcc acatcaagct aatcttgaat ttgttcgtaa tcgtgtagaa     1920
ctggttccac taaccgaaat cgttaatcgc attgcggcag aaggagcact tcctttatcca    1980 ccgggtgtgc tttgtgtcgt accgggtgaa aaatggagtc agactgcaca ggaatatttc     2040
ttagcactcg aagaaggcat taatttatta ccaggtttcg caccagaaat tcaagggta      2100 tatctacaac aagatgcaga tggacgtatt cgtgcttatg gctacgtatt aactgaaaac     2160
taa                                                                    2163
```

<210> SEQ ID NO 62
<211> LENGTH: 720
<212> TYPE: PRT
<213> ORGANISM: Pasteurella multocida

<400> SEQUENCE: 62

```
Met Leu Asn Leu Lys Ile Ala Tyr Ser Pro Leu Ile Arg Pro Tyr Phe
1               5                   10                  15
```

-continued

His Thr Asn Arg Glu Leu Val Ser Val Gln Glu Thr Asp Phe Thr Asp
        20                  25                  30

Ile Gly Ala Ile Ile Leu Ser Ser Glu Asp Ile Glu Asp Tyr Ile Asp
        35                  40                  45

Ser Ile Gln Ala Thr Glu Phe Asn Ile Pro Val Phe Val Ala Val Ile
50                  55                  60

Glu Gly Gln Phe Leu Asp Pro Gln Phe Phe Asp Lys Val Tyr His Val
65                  70                  75                  80

Gln Asp Leu Asn Asn Tyr Asp Ile Asn Leu Tyr Ser Arg Gln Ile Glu
                85                  90                  95

Thr Ala Ala Arg Phe Tyr Glu Glu Lys Ile Leu Pro Pro Phe Phe Lys
                100                 105                 110

Met Leu Ser Glu Tyr Val Glu Met Gly Asn Ser Ala Phe Asp Cys Pro
                115                 120                 125

Gly His Gln Gly Gly Gln Tyr Phe Arg Lys His Pro Ala Gly Arg Tyr
                130                 135                 140

Leu Tyr Asp Phe Tyr Gly Glu Asn Ile Phe Arg Ser Asp Ile Cys Asn
145                 150                 155                 160

Ala Asp Val Lys Leu Gly Asp Leu Leu Ile His Glu Gly Ala Ala Cys
                165                 170                 175

Asp Ala Gln Lys His Ala Ala Gln Val Phe Asn Ala Asp Lys Thr Tyr
                180                 185                 190

Phe Val Leu Asn Gly Thr Ser Ser Ala Asn Lys Val Val Thr Asn Ala
                195                 200                 205

Leu Leu Thr Pro Gly Asp Leu Val Leu Phe Asp Arg Asn Asn His Lys
                210                 215                 220

Ser Ile His His Gly Ala Leu Ile Gln Ala Gly Ala Thr Pro Val Tyr
225                 230                 235                 240

Leu Glu Thr Ala Arg Asn Pro Phe Gly Phe Ile Gly Gly Ile Asp Ser
                245                 250                 255

His Cys Phe Asp Glu Asp Tyr Leu Lys Ser Leu Ile Lys Asp Val Ala
                260                 265                 270

Pro Glu Lys Leu Thr Gln Ala Arg Pro Phe Arg Leu Ala Val Ile Gln
                275                 280                 285

Leu Gly Thr Tyr Asp Gly Thr Ile Tyr Asn Ala Arg Gln Val Val Asp
                290                 295                 300

Lys Ile Gly His Leu Cys Asp Tyr Ile Leu Phe Asp Ser Ala Trp Val
305                 310                 315                 320

Gly Tyr Glu Gln Phe Ile Pro Met Met Lys Asp Cys Ser Pro Leu Leu
                325                 330                 335

Leu Glu Leu Asn Glu Asn Asp Pro Gly Ile Ile Val Thr Gln Ser Val
                340                 345                 350

His Lys Gln Gln Ala Gly Phe Ser Gln Ala Ser Gln Ile His Lys Lys
                355                 360                 365

Asp Lys His Ile Lys Gly Gln Gln Arg Tyr Cys Asn His Lys Arg Phe
                370                 375                 380

Asn Asn Ala Phe Met Leu His Ala Ser Thr Ser Pro Phe Tyr Pro Leu
385                 390                 395                 400

Phe Ala Thr Leu Asp Val Asn Ala Lys Ile Gln Gly Thr Pro Ala Gly
                405                 410                 415

Ile Arg Leu Trp His Asp Cys Val Lys Ile Gly Ile Glu Ala Arg Lys
                420                 425                 430

-continued

```
Met Val Leu Asn Ser Cys Asp Leu Ile Lys Pro Phe Ile Pro Pro Tyr
        435                 440                 445

Val Asn Gly Lys Lys Trp Gln Asp Tyr Asp Thr Glu Glu Met Ala Asn
    450                 455                 460

Asp Leu Thr Phe Phe Lys Phe His Ala Asp Asp Lys Trp His Gln Phe
465                 470                 475                 480

Glu Gly Tyr Val Asp Asn Gln Tyr Phe Val Asp Pro Cys Lys Phe Met
                485                 490                 495

Leu Thr Thr Pro Gly Ile Asp Ile Glu Thr Gly Glu Tyr Glu Asp Phe
            500                 505                 510

Gly Val Pro Ala Thr Ile Leu Ala Asn Tyr Leu Arg Glu Asn Gly Ile
        515                 520                 525

Ile Pro Glu Lys Cys Asp Leu Asn Ser Ile Leu Phe Leu Leu Thr Pro
    530                 535                 540

Ala Glu Thr Leu Thr Lys Met Gln Ser Leu Val Ala Gln Ile Ala Ala
545                 550                 555                 560

Phe Glu Gln His Ile Lys Lys Asp Ser Leu Leu Lys Glu Val Leu Pro
                565                 570                 575

Ser Val Tyr His Asn Asn Glu Lys Arg Tyr Glu Gly Tyr Thr Ile Arg
            580                 585                 590

Arg Leu Cys Gln Glu Met His Asp Leu Tyr Val Ser Arg Asn Val Lys
        595                 600                 605

Thr Leu Gln Arg Asn Leu Phe Arg Lys Ala Thr Leu Pro Glu Tyr Val
    610                 615                 620

Met Asn Pro His Gln Ala Asn Leu Glu Phe Val Arg Asn Arg Val Glu
625                 630                 635                 640

Leu Val Pro Leu Thr Glu Ile Val Asn Arg Ile Ala Ala Glu Gly Ala
                645                 650                 655

Leu Pro Tyr Pro Pro Gly Val Leu Cys Val Val Pro Gly Glu Lys Trp
            660                 665                 670

Ser Gln Thr Ala Gln Glu Tyr Phe Leu Ala Leu Glu Glu Gly Ile Asn
        675                 680                 685

Leu Leu Pro Gly Phe Ala Pro Glu Ile Gln Gly Val Tyr Leu Gln Gln
    690                 695                 700

Asp Ala Asp Gly Arg Ile Arg Ala Tyr Gly Tyr Val Leu Thr Glu Asn
705                 710                 715                 720

<210> SEQ ID NO 63
<211> LENGTH: 101
<212> TYPE: DNA
<213> ORGANISM: Pasteurella multocida

<400> SEQUENCE: 63
gaaaaattag agaaacaaat agaatcactc aatctacaag aagattgttt tcttttagga      60
aataaagata atccgtatcc attaataaaa aatgctaagc t                          101

<210> SEQ ID NO 64
<211> LENGTH: 1179
<212> TYPE: DNA
<213> ORGANISM: Pasteurella multocida

<400> SEQUENCE: 64
atgaatattc tatttgtaca taaaagcctt gtcgtcggag gcgctgaaag aattctaatt      60
aactatttaa atattctatc tggatttaat gaattcaaag ttacattact tttactagaa     120
aataaaggtg aagataacaa aaacatcaat caaatcaata aaaatattaa tatagatttt     180
```

-continued

```
attctagaca atagtgagtc aagaaaatat actgaatttg aaaataaaat aaatcagcgc   240
agcatcttca gaaaaatata taaatataaa ctatcaaaaa ttaataagat agaagaaaat   300
agaataaaaa aatacattaa aaacaaggaa tttgatttaa ttgttaattt taactcacac   360
cttgatttct tcttatcaaa caatcaaatt aacatcccga taattcgttg gatacacggt   420
caagctcatt tagatgactg gtgcaacaga agagaatggt accaaaacat tcttcctaaa   480
cacacttatt tctttgcaat tacaaaagaa atgcaaaaaa atgctcaaaa aatcttacta   540
tcttacggga tccaagaaga aagaatacat atcttataca atcctattga tattaatttt   600
gtccaggaac aatcaatcaa aaatactcat gacattcatc ataaacaata cttaattaac   660
gtttctcgtt tagatataga taagaatcat gaacaaatga ttaatattta ttatcaatta   720
aaaaaacgag gtatccaaga aaaattatat attgttgggg atggtgagtg tcgagaaaaa   780
ttagagaaac aaatagaatc actcaatcta caagaagatt gctttctttt aggaaataaa   840
gataatccgt atccattaat aaaaaatgct aagctattct tacacacctc tttgaaagag   900
gggttaccga cagttatcct agaaagcatg gcctgcggta cacctgtaat atccatggac   960
tgccctaccg gtccgaaaga aattctccga ggaggagaat ttggaggatt agtaaattta  1020
ggtgacgaga atgcttttat acaaaaaaca ctctctttcc ttcaaaatca agatgaatac  1080
aaccattatt gtaataaatt agaacaagct atttctcctt ttcgctttga agaaatcagc  1140
actatactct tatctcattt acaaaaattc aatagttaa                         1179
```

<210> SEQ ID NO 65
<211> LENGTH: 392
<212> TYPE: PRT
<213> ORGANISM: Pasteurella multocida

<400> SEQUENCE: 65

```
Met Asn Ile Leu Phe Val His Lys Ser Leu Val Val Gly Gly Ala Glu
1               5                   10                  15

Arg Ile Leu Ile Asn Tyr Leu Asn Ile Leu Ser Gly Phe Asn Glu Phe
            20                  25                  30

Lys Val Thr Leu Leu Leu Leu Glu Asn Lys Gly Glu Asp Asn Lys Asn
        35                  40                  45

Ile Asn Gln Ile Asn Lys Asn Ile Asn Ile Asp Phe Ile Leu Asp Asn
    50                  55                  60

Ser Glu Ser Arg Lys Tyr Thr Glu Phe Glu Asn Lys Ile Asn Gln Arg
65                  70                  75                  80

Ser Ile Phe Arg Lys Ile Tyr Lys Tyr Lys Leu Ser Lys Ile Asn Lys
                85                  90                  95

Ile Glu Glu Asn Arg Ile Lys Lys Tyr Ile Lys Asn Lys Glu Phe Asp
            100                 105                 110

Leu Ile Val Asn Phe Asn Ser His Leu Asp Phe Phe Leu Ser Asn Asn
        115                 120                 125

Gln Ile Asn Ile Pro Ile Ile Arg Trp Ile His Gly Gln Ala His Leu
    130                 135                 140

Asp Asp Trp Cys Asn Arg Arg Glu Trp Tyr Gln Asn Ile Leu Pro Lys
145                 150                 155                 160

His Thr Tyr Phe Phe Ala Ile Thr Lys Glu Met Gln Lys Asn Ala Gln
                165                 170                 175

Lys Ile Leu Leu Ser Tyr Gly Ile Gln Glu Glu Arg Ile His Ile Leu
            180                 185                 190
```

```
Tyr Asn Pro Ile Asp Ile Asn Phe Val Gln Glu Gln Ser Ile Lys Asn
            195                 200                 205

Thr His Asp Ile His His Lys Gln Tyr Leu Ile Asn Val Ser Arg Leu
        210                 215                 220

Asp Ile Asp Lys Asn His Glu Gln Met Ile Asn Ile Tyr Tyr Gln Leu
225                 230                 235                 240

Lys Lys Arg Gly Ile Gln Glu Lys Leu Tyr Ile Val Gly Asp Gly Glu
                245                 250                 255

Cys Arg Glu Lys Leu Glu Lys Gln Ile Glu Ser Leu Asn Leu Gln Glu
            260                 265                 270

Asp Cys Phe Leu Leu Gly Asn Lys Asp Asn Pro Tyr Pro Leu Ile Lys
        275                 280                 285

Asn Ala Lys Leu Phe Leu His Thr Ser Leu Lys Glu Gly Leu Pro Thr
    290                 295                 300

Val Ile Leu Glu Ser Met Ala Cys Gly Thr Pro Val Ile Ser Met Asp
305                 310                 315                 320

Cys Pro Thr Gly Pro Lys Glu Ile Leu Arg Gly Gly Glu Phe Gly Gly
                325                 330                 335

Leu Val Asn Leu Gly Asp Glu Asn Ala Phe Ile Gln Lys Thr Leu Ser
            340                 345                 350

Phe Leu Gln Asn Gln Asp Glu Tyr Asn His Tyr Cys Asn Lys Leu Glu
        355                 360                 365

Gln Ala Ile Ser Pro Phe Arg Phe Glu Glu Ile Ser Thr Ile Leu Leu
    370                 375                 380

Ser His Leu Gln Lys Phe Asn Ser
385                 390

<210> SEQ ID NO 66
<211> LENGTH: 222
<212> TYPE: DNA
<213> ORGANISM: Pasteurella multocida

<400> SEQUENCE: 66
agcagagtaa gttctttttg cttgttaagt aacaaagctt attgtgacga cacgcgggtc     60
taaattgtgt tttccccagc gagtagcgta aagtaatctt gtccagcaag gatagcgatc    120
ccgacagaca tcgcttatgt aatggactga gcgtaatcta attgccgcat gccatgtttc    180
aatttctttg aactcttgta tcgtccatga aaattcaggg cg                       222

<210> SEQ ID NO 67
<211> LENGTH: 831
<212> TYPE: DNA
<213> ORGANISM: Pasteurella multocida

<400> SEQUENCE: 67
atgtctgaca aaatttcacc caataagata tctgcgcttt cttctacttt attaatcact     60
ctttgggcaa aagcagttga atatgataaa gccaatccat tactgaaaga tcgcgaagca    120
gcaagaatga aaaaacagat tgactatgac tttcaaaagt tgaatctgc tcatttatca    180 caagtgggat gttgtggacg cgcaaaatta tttgatcaag aaagcttaaa atttctttca    240
cagcaccaag acgcggttgt tgtgcagctt ggtgcgggct tagatgcacg ctttgaacgc    300
ttaggcaaac cacaagtcag tgcgtggtat gatttagact tacctgaagt catcaatata    360
cgtcgccaac ttttaccaga aacgagtaat cattatttgg ctgactcact tttcaataca    420
gattggatga aacagttag tcaacataac aaacccgttt tattaattct tgaaggcgta    480
```

-continued

```
ttgatgtttt ttcctaaaga acaagtcaaa cagtttattg cctctgtggc tgaaaactta    540
cctaacagca caatgatttt cgatattgtg cccccaatgg cagtcggtcg tagtaaatac    600
cacgatgcac tcaaaaaaat agacagtcaa gaacgccctg aattttcatg gacaatacaa    660
gagatcaaag aaattgaaac atggcatgcg gcaattaaat tacgctcagt ccattacata    720
agcgatgtct gtcgggatcg ctatccttgc tggacaagat tactttacgc tactcgctgg    780
ggaaaacaca atttagaccc gcgtgtcgtc acaataagct ttgttactta a             831

<210> SEQ ID NO 68
<211> LENGTH: 276
<212> TYPE: PRT
<213> ORGANISM: Pasteurella multocida

<400> SEQUENCE: 68

Met Ser Asp Lys Ile Ser Pro Asn Lys Ile Ser Ala Leu Ser Ser Thr
1               5                   10                  15

Leu Leu Ile Thr Leu Trp Ala Lys Ala Val Glu Tyr Asp Lys Ala Asn
            20                  25                  30

Pro Leu Leu Lys Asp Arg Glu Ala Ala Arg Met Lys Lys Gln Ile Asp
        35                  40                  45

Tyr Asp Phe Gln Lys Phe Glu Ser Ala His Leu Ser Gln Val Gly Cys
    50                  55                  60

Cys Gly Arg Ala Lys Leu Phe Asp Gln Glu Ser Leu Lys Phe Leu Ser
65                  70                  75                  80

Gln His Gln Asp Ala Val Val Val Gln Leu Gly Ala Gly Leu Asp Ala
                85                  90                  95

Arg Phe Glu Arg Leu Gly Lys Pro Gln Val Ser Ala Trp Tyr Asp Leu
            100                 105                 110

Asp Leu Pro Glu Val Ile Asn Ile Arg Arg Gln Leu Leu Pro Glu Thr
        115                 120                 125

Ser Asn His Tyr Leu Ala Asp Ser Leu Phe Asn Thr Asp Trp Met Lys
    130                 135                 140

Thr Val Ser Gln His Asn Lys Pro Val Leu Leu Ile Leu Glu Gly Val
145                 150                 155                 160

Leu Met Phe Phe Pro Lys Glu Gln Val Lys Gln Phe Ile Ala Ser Val
                165                 170                 175

Ala Glu Asn Leu Pro Asn Ser Thr Met Ile Phe Asp Ile Val Pro Pro
            180                 185                 190

Met Ala Val Gly Arg Ser Lys Tyr His Asp Ala Leu Lys Lys Ile Asp
        195                 200                 205

Ser Gln Glu Arg Pro Glu Phe Ser Trp Thr Ile Gln Glu Ile Lys Glu
    210                 215                 220

Ile Glu Thr Trp His Ala Ala Ile Lys Leu Arg Ser Val His Tyr Ile
225                 230                 235                 240

Ser Asp Val Cys Arg Asp Arg Tyr Pro Cys Trp Thr Arg Leu Leu Tyr
                245                 250                 255

Ala Thr Arg Trp Gly Lys His Asn Leu Asp Pro Arg Val Val Thr Ile
            260                 265                 270

Ser Phe Val Thr
        275

<210> SEQ ID NO 69
<211> LENGTH: 55
<212> TYPE: DNA
<213> ORGANISM: Pasteurella multocida
```

<400> SEQUENCE: 69

```
tcgatgaaaa acgccattat ggtcatggaa tcagctgcaa aattctcact ccaca        55
```

<210> SEQ ID NO 70
<211> LENGTH: 1314
<212> TYPE: DNA
<213> ORGANISM: Pasteurella multocida

<400> SEQUENCE: 70

```
atggtattac actataccccc tcatcaatcc gccccacgca acacaacatt cgttgcggaa    60
attcttgatc ttgattatca aggacgtggt gtagccaaag tacaaggcaa aacgtggttc   120
attgaaaatg cactgccaca agaaaaagtg gaagtgcgca ttgtcgatga aaaacgccat   180
tatggtcatg ggatcagctg caaaattctc actccacatc cagatcgcca gtcagcaaaa   240
tgtgcttact atgcccagtg cggtggttgc caaagtcaac atattccaat tgacatgcaa   300
cgtcaggcta acaacaagc cttattccaa cgcttacaac aattacaacc tcaagcgacc   360
ttcatgccca tgatcgtcgc agcgccttgg cattatcgcc gtcgtgtgcg tttaagcgtg   420
cggtttcatc ccaaaagcaa acaacttgcg atgggtttgc gtcagagaaa tactcaacaa   480
atcgtgaatc tgcagcattg tgatgtgctt gaaatcccct taagtcaact cttacctaaa   540
ctacatttgt tgttttcaac atggtccctg cctaaaaacc tagggcatgt ggagttagtg   600
catgcggata atggaattgc gatgttatta cgccatacag gaaatttagc gcaaactgac   660
cgcactttat taaccaattt tgcgcaacaa gaaaacttaa tgttgtttgt acaagatgat   720
caacagatca cccaactaca tggcgaggca ccttactaca tactcgcga tggcaccaaa   780
ttacagtttg atatccgtga ctttatccaa gtgaatgctg ttgtaaatca gaaatgatt   840
gatactgctc ttgagtggtt ggaactcaca tcgaacgata acgtattaga tttgtttgt   900
ggtatgggaa acttcaccct cccaatcagt cgtcaggtca atcaggttgt gggcattgaa   960
ggcgtaggag aaatggtgga gaaagcaaaa cgaaatgcgg aacaaaatca atgtgataat  1020
gtccaattct atcaggcgaa tttagatcaa ccttttgtgc aacaacattg ggcgagccaa  1080
catttttaat aaaattttact ggacccacca cgtacaggcg cggcatttgc cttacatgcc  1140
ttatgtgaat tgggcgcaga aaaaatctta tatgtttcct gcaatcctgc tacattagta  1200
cgtgatacag cgatttttatt acaatttaac taccgactta agaaagtcgc aatgatcgat  1260
atgttcccca atacaggaca tttagaatcc atcagtttat ttgaaaaaga atag         1314
```

<210> SEQ ID NO 71
<211> LENGTH: 437
<212> TYPE: PRT
<213> ORGANISM: Pasteurella multocida

<400> SEQUENCE: 71

```
Met Val Leu His Tyr Thr Pro His Gln Ser Ala Pro Arg Asn Thr Thr
1               5                  10                  15

Phe Val Ala Glu Ile Leu Asp Leu Asp Tyr Gln Gly Arg Gly Val Ala
            20                  25                  30

Lys Val Gln Gly Lys Thr Trp Phe Ile Glu Asn Ala Leu Pro Gln Glu
        35                  40                  45

Lys Val Glu Val Arg Ile Val Asp Glu Lys Arg His Tyr Gly His Gly
    50                  55                  60

Ile Ser Cys Lys Ile Leu Thr Pro His Pro Asp Arg Gln Ser Ala Lys
65                  70                  75                  80
```

-continued

```
Cys Ala Tyr Tyr Ala Gln Cys Gly Gly Cys Gln Ser Gln His Ile Pro
                85                  90                  95

Ile Asp Met Gln Arg Gln Ala Lys Gln Gln Ala Leu Phe Gln Arg Leu
            100                 105                 110

Gln Gln Leu Gln Pro Gln Ala Thr Phe Met Pro Met Ile Val Ala Ala
        115                 120                 125

Pro Trp His Tyr Arg Arg Arg Val Arg Leu Ser Val Arg Phe His Pro
    130                 135                 140

Lys Ser Lys Gln Leu Ala Met Gly Leu Arg Gln Arg Asn Thr Gln Gln
145                 150                 155                 160

Ile Val Asn Leu Gln His Cys Asp Val Leu Glu Ile Pro Leu Ser Gln
                165                 170                 175

Leu Leu Pro Lys Leu His Leu Leu Phe Ser Thr Trp Ser Leu Pro Lys
            180                 185                 190

Asn Leu Gly His Val Glu Leu Val His Ala Asp Asn Gly Ile Ala Met
        195                 200                 205

Leu Leu Arg His Thr Gly Asn Leu Ala Gln Thr Asp Arg Thr Leu Leu
    210                 215                 220

Thr Asn Phe Ala Gln Gln Glu Asn Leu Met Leu Phe Val Gln Asp Asp
225                 230                 235                 240

Gln Gln Ile Thr Gln Leu His Gly Glu Ala Pro Tyr Tyr Ile Leu Arg
                245                 250                 255

Asp Gly Thr Lys Leu Gln Phe Asp Ile Arg Asp Phe Ile Gln Val Asn
            260                 265                 270

Ala Val Val Asn Gln Lys Met Ile Asp Thr Ala Leu Glu Trp Leu Glu
        275                 280                 285

Leu Thr Ser Asn Asp Asn Val Leu Asp Leu Phe Cys Gly Met Gly Asn
    290                 295                 300

Phe Thr Leu Pro Ile Ser Arg Gln Val Asn Gln Val Val Gly Ile Glu
305                 310                 315                 320

Gly Val Gly Glu Met Val Glu Lys Ala Lys Arg Asn Ala Glu Gln Asn
                325                 330                 335

Gln Cys Asp Asn Val Gln Phe Tyr Gln Ala Asn Leu Asp Gln Pro Phe
            340                 345                 350

Val Gln Gln His Trp Ala Ser Gln His Phe Asn Lys Ile Leu Leu Asp
        355                 360                 365

Pro Pro Arg Thr Gly Ala Ala Phe Ala Leu His Ala Leu Cys Glu Leu
    370                 375                 380

Gly Ala Glu Lys Ile Leu Tyr Val Ser Cys Asn Pro Ala Thr Leu Val
385                 390                 395                 400

Arg Asp Thr Ala Ile Leu Leu Gln Phe Asn Tyr Arg Leu Lys Lys Val
                405                 410                 415

Ala Met Ile Asp Met Phe Pro Asn Thr Gly His Leu Glu Ser Ile Ser
            420                 425                 430

Leu Phe Glu Lys Glu
        435

<210> SEQ ID NO 72
<211> LENGTH: 598
<212> TYPE: DNA
<213> ORGANISM: Pasteurella multocida
<220> FEATURE:
<221> NAME/KEY: modified_base
<222> LOCATION: (412)
<223> OTHER INFORMATION: a, t, c, g, other or unknown
```

-continued

<220> FEATURE:
<221> NAME/KEY: modified_base
<222> LOCATION: (451)
<223> OTHER INFORMATION: a, t, c, g, other or unknown
<220> FEATURE:
<221> NAME/KEY: modified_base
<222> LOCATION: (471)
<223> OTHER INFORMATION: a, t, c, g, other or unknown
<220> FEATURE:
<221> NAME/KEY: modified_base
<222> LOCATION: (503)
<223> OTHER INFORMATION: a, t, c, g, other or unknown
<220> FEATURE:
<221> NAME/KEY: modified_base
<222> LOCATION: (546)
<223> OTHER INFORMATION: a, t, c, g, other or unknown
<220> FEATURE:
<221> NAME/KEY: modified_base
<222> LOCATION: (562)..(564)
<223> OTHER INFORMATION: a, t, c, g, other or unknown
<220> FEATURE:
<221> NAME/KEY: modified_base
<222> LOCATION: (576)
<223> OTHER INFORMATION: a, t, c, g, other or unknown
<220> FEATURE:
<221> NAME/KEY: modified_base
<222> LOCATION: (588)..(590)
<223> OTHER INFORMATION: a, t, c, g, other or unknown
<220> FEATURE:
<221> NAME/KEY: modified_base
<222> LOCATION: (595)
<223> OTHER INFORMATION: a, t, c, g, other or unknown

<400> SEQUENCE: 72
tcagtacttt gcttgcttaa gcaagtaaaa agtgcggtca tttttagcaa aaataaaggg 60
cttctgtttg gaagcccttt gtgtattgca agttagtctt ttttatgagt gtattcttta 120
tacatcgctt caatttgtgc tttatagcgt tccaaaatca ctttacgacg gagtttcaat 180
gtcggagtaa tttcttccat ttttgtggta aatgcctgag gtaataaagt gaatttttta 240
atttgctcaa agctaggcaa ttctttttgt aaatcattaa tacgctgttc aaacatttga 300
agaatatcag aatgtttaat gagttctaaa cgatcgtgat attttatatt taattgtttg 360
gcgtattctt caagactatt aaagcaaggc acaataagcg ctgagacata tnttttggca 420
tccgcaatga ctgcaatttg ttcaataaat ntatctttac ccactttggt ntcaatatat 480
tgtggagcaa tatattttcc atnggaggtt ttcattaact ctttgatacg atctgtaata 540
tataantacc ttgtggatca annncccagc atcacnagtt tttaaaannn gtctnctg 598

<210> SEQ ID NO 73
<211> LENGTH: 561
<212> TYPE: DNA
<213> ORGANISM: Pasteurella multocida
<220> FEATURE:
<221> NAME/KEY: modified_base
<222> LOCATION: (560)..(561)
<223> OTHER INFORMATION: a, t, c, g, other or unknown

<400> SEQUENCE: 73
gagcaaagta gctgtccgcc gtatattgta agaagttggc ataagaatta acgcctaact 60
tgaccgcatc gcccatcgga tctaaacgac ctacatgtac gccggtacct ttacttaaac 120
tttcaattac ttttggtgtg aattgtggct ccgcaaataa gcaattcact ttatgttctt 180
taatttcccg cttaattttc gctaacgtct tagctcccgg cgccaccaac ggattaattg 240
tgaaataacc ggtttgtttt aagccataag cattattgaa ataactatac gcatcatgga 300
aaacataaaa cccttttttct ttaactggtg cgagttgctg tttaattttc tcgctttgtt 360

```
cagctaaagt gcggttaaat tctgccaaat tttgcgcaat tttctcttt  ctctctggat    420 aagcttccgt taaacgtgtt gctaagcgtg tcgcgacaat tttgctaatc tctggcgaat    480
accacacatg ccagttagta ctgtgatcat gctcgtgttc atgtgcgtgg tcatgtttat    540
gctcatggtc gtgtttgtgn n                                              561

<210> SEQ ID NO 74
<211> LENGTH: 575
<212> TYPE: DNA
<213> ORGANISM: Pasteurella multocida
<220> FEATURE:
<221> NAME/KEY: modified_base
<222> LOCATION: (574)..(575)
<223> OTHER INFORMATION: a, t, c, g, other or unknown

<400> SEQUENCE: 74
ttacttgctt aagcaagcaa agtagctgtc cgccgtatat tgtaagaagt tggcataaga     60
attaacgcct aacttgaccg catcgcccat cggatctaaa cgacctacat gtacgccggt    120
acctttactt aaactttcaa ttactttggg tgtgaattgt ggctccgcaa ataagcaatt    180
cactttatgt tctttaattt cccgcttaat tttcgctaac gtcttagctc ccggcgccac    240
caacggatta attgtgaaat aaccggtttg ttttaagcca taagcattat tgaaataact    300
atacgcatca tggaaaacat aaaacccttt tctttaact  ggtgcgagtt gctgtttaat    360
tttctcgctt tgttcagcta aagtgcggtt aaattctgcc aaattttgcg caattttctc    420 tttctctct  ggataagctt ccgttaaacg tgttgctaag cgtgtcgcga caattttgct    480
aatctctggc gaataccaca catgccagtt agtactgtga tcatgctcgt gttcatgtgc    540
gtggtcatgt ttatgctcat ggtcgtgttt gtgnn                               575

<210> SEQ ID NO 75
<211> LENGTH: 1101
<212> TYPE: DNA
<213> ORGANISM: Pasteurella multocida

<400> SEQUENCE: 75
atggcacgtt tcattaagac attgaaaaaa accgcattag cggcaagtat tgcttcttta     60
gcaactgtgg caaatgcgac gattgtgact tcgattaaac cattaggttt tattgcttca    120
tcgattgctg atggggtaac agacactgaa gtattagttc ctgcgggtgc ttcaccacat    180
gattacagct aaaaccctc  agatatacaa aaattacagg gggcggaatt aatcctgtgg    240
gtcggggaag acattgatgc tttccttgat aaaacattac gtccaatgcc ttttaaaaag    300
gtgttaagta ttgctgattt tgcggaaatt ggtggtttgc ttgaaggtga agcacatgat    360
cataaacatg agcatgatca tactcacaaa acgaccacg  atcacaaaca cgaccacgat    420
cacaaacacg accacgatca caaacatgag cacgatcata acacgacca  cgatcacaaa    480 catgaccacg atcacaaaca cgaccatgct cacaagcatg agcacgatca caaacacgac    540
catgagcata acatgacca  cgcacatgga cacgagcatg atcacagtac taactggcat    600
gtgtggtatt cgccagagat tagcaaaatt gtcgcgacac gcttagcaac acgtttaacg    660
gaagcttatc cagagaaaaa agagaaaatt gcgcaaaatt tggcagaatt taaccgtact    720
ttagctgaac aaagcgagaa aattaaacag caactcgcac cagttaaaga aaagggttt    780 tatgttttcc atgatgcgta tagctatttc aataatgctt atggcttaaa acaaaccggt    840
tatttcacaa ttaatccgtt ggtggcgccg gagctaaga  cgttagcgaa aattaagcag    900
gaaattaaag aacataaagt gaattgctta tttgcggagc cacaattcac accaaaagta    960
```

-continued

```
attgaaagtt taagtaaagg taccggtgta catgtaggtc gtttagatcc gatgggcgat    1020
gcggtcaagt taggcgttaa ttcttatgcc aacttcttac aatatacggc ggacagctac    1080
tttgcttgct taagcaagta a                                              1101
```

<210> SEQ ID NO 76
<211> LENGTH: 366
<212> TYPE: PRT
<213> ORGANISM: Pasteurella multocida

<400> SEQUENCE: 76

```
Met Ala Arg Phe Ile Lys Thr Leu Lys Lys Thr Ala Leu Ala Ala Ser
1               5                   10                  15

Ile Ala Ser Leu Ala Thr Val Ala Asn Ala Thr Ile Val Thr Ser Ile
            20                  25                  30

Lys Pro Leu Gly Phe Ile Ala Ser Ser Ile Ala Asp Gly Val Thr Asp
        35                  40                  45

Thr Glu Val Leu Val Pro Ala Gly Ala Ser Pro His Asp Tyr Ser Leu
    50                  55                  60

Lys Pro Ser Asp Ile Gln Lys Leu Gln Gly Ala Glu Leu Ile Leu Trp
65                  70                  75                  80

Val Gly Glu Asp Ile Asp Ala Phe Leu Asp Lys Thr Leu Arg Pro Met
                85                  90                  95

Pro Phe Lys Lys Val Leu Ser Ile Ala Asp Phe Ala Glu Ile Gly Gly
            100                 105                 110

Leu Leu Glu Gly Glu Ala His Asp His Lys His Glu His Asp His Thr
        115                 120                 125

His Lys His Asp His Asp His Lys His Asp His Asp His Lys His Asp
    130                 135                 140

His Asp His Lys His Glu His Asp His Lys His Asp His Asp His Lys
145                 150                 155                 160

His Asp His Asp His Lys His Asp His Ala His Lys His Glu His Asp
                165                 170                 175

His Lys His Asp His Glu His Lys His Asp His Ala His Gly His Glu
            180                 185                 190

His Asp His Ser Thr Asn Trp His Val Trp Tyr Ser Pro Glu Ile Ser
        195                 200                 205

Lys Ile Val Ala Thr Arg Leu Ala Thr Arg Leu Thr Glu Ala Tyr Pro
    210                 215                 220

Glu Lys Lys Glu Lys Ile Ala Gln Asn Leu Ala Glu Phe Asn Arg Thr
225                 230                 235                 240

Leu Ala Glu Gln Ser Glu Lys Ile Lys Gln Gln Leu Ala Pro Val Lys
                245                 250                 255

Glu Lys Gly Phe Tyr Val Phe His Asp Ala Tyr Ser Tyr Phe Asn Asn
            260                 265                 270

Ala Tyr Gly Leu Lys Gln Thr Gly Tyr Phe Thr Ile Asn Pro Leu Val
        275                 280                 285

Ala Pro Gly Ala Lys Thr Leu Ala Lys Ile Lys Gln Glu Ile Lys Glu
    290                 295                 300

His Lys Val Asn Cys Leu Phe Ala Glu Pro Gln Phe Thr Pro Lys Val
305                 310                 315                 320

Ile Glu Ser Leu Ser Lys Gly Thr Gly Val His Val Gly Arg Leu Asp
                325                 330                 335

Pro Met Gly Asp Ala Val Lys Leu Gly Val Asn Ser Tyr Ala Asn Phe
```

-continued

```
                   340                 345                 350
Leu Gln Tyr Thr Ala Asp Ser Tyr Phe Ala Cys Leu Ser Lys
            355                 360                 365

<210> SEQ ID NO 77
<211> LENGTH: 70
<212> TYPE: DNA
<213> ORGANISM: Pasteurella multocida

<400> SEQUENCE: 77
gctttgcatt tgagtcataa aatagtacag tacggtaatt ttctggatga ataccttttt    60
tcatattggc                                                          70

<210> SEQ ID NO 78
<211> LENGTH: 267
<212> TYPE: DNA
<213> ORGANISM: Pasteurella multocida

<400> SEQUENCE: 78
atgaaaaaag gtattcatcc agaaaattac cgtactgtac tattttatga ctcaaatgca    60
aagcaaggtt ttttaatccg ctcttgcgcc agaaccacaa cgaccatgaa atgggaagat   120
ggtcatgaat atcctgtctt tatgtgtgat acctcctcag catcacaccc gtactataca   180
ggtaaaacac gtcaaattgc gaatgaaggt cgtgcaagcg actttgtcaa tcgctacggc   240
aaatttggca cattaaaatc aaaataa                                       267

<210> SEQ ID NO 79
<211> LENGTH: 88
<212> TYPE: PRT
<213> ORGANISM: Pasteurella multocida

<400> SEQUENCE: 79

Met Lys Lys Gly Ile His Pro Glu Asn Tyr Arg Thr Val Leu Phe Tyr
1               5                   10                  15

Asp Ser Asn Ala Lys Gln Gly Phe Leu Ile Arg Ser Cys Ala Arg Thr
            20                  25                  30

Thr Thr Thr Met Lys Trp Glu Asp Gly His Glu Tyr Pro Val Phe Met
        35                  40                  45

Cys Asp Thr Ser Ser Ala Ser His Pro Tyr Tyr Thr Gly Lys Thr Arg
    50                  55                  60

Gln Ile Ala Asn Glu Gly Arg Ala Ser Asp Phe Val Asn Arg Tyr Gly
65                  70                  75                  80

Lys Phe Gly Thr Leu Lys Ser Lys
                85

<210> SEQ ID NO 80
<211> LENGTH: 506
<212> TYPE: DNA
<213> ORGANISM: Pasteurella multocida

<400> SEQUENCE: 80
tgctccaact ctactttcaa cctatcctct gtccatgttc ttggaaacat cgtggataca    60
cctttatttc cttttttctc caaaacttcg gggcagtagg agatcaacac cctcgcttca   120
tagaccccat ttgggtattc cttaatcacc ttatctacaa tcacattgcc taagatggtg   180
tgtcttaacg ctcccatgta aaaaaatggt caatttctca aaacaaaact ttttcaaaat   240
tgaccgcact ttttcttcta actgttcctt ttcagaaaat caacaccttc acttaagaaa   300
```

```
acccctacgc atatttctcc atcagggcaa tgatagcttg agagctagga cgatgggact    360 catattttt tatcccctca agtaattcat gttgtccatt aaaataatgt acgtttccac    420
ctttatccag catcaattta agcagatcta gcgctttcag ggacataacc tgtcattgcc    480
aatggaatca cttggtctcg atttgg                                        506
```

<210> SEQ ID NO 81
<211> LENGTH: 348
<212> TYPE: DNA
<213> ORGANISM: Pasteurella multocida

<400> SEQUENCE: 81

```
atgagagcgt taagacacac caccttaggc aatgtgattg tggataaggt gattaaggaa     60
tacccaaatg gggtttatga agcgagggtg ttgatcccta acccgaaagc ccaaaccgat    120
cctaccgccc cgaagttttt ggagaaaagg ggaaataaag gtgtatccac gatgtttcca    180
agaacatgga cagaggatag gttgaaagtg gagttggagc atgcgtttaa aaatggtata    240
cacgataaag ggcaagtatg gactgggata actaaatcag gtgttaaagt acaatggtat    300
agaagtgaaa aggtgagat aaccagtgtt catccaatct tagaataa                 348
```

<210> SEQ ID NO 82
<211> LENGTH: 115
<212> TYPE: PRT
<213> ORGANISM: Pasteurella multocida

<400> SEQUENCE: 82

```
Met Arg Ala Leu Arg His Thr Thr Leu Gly Asn Val Ile Val Asp Lys
 1               5                  10                  15

Val Ile Lys Glu Tyr Pro Asn Gly Val Tyr Glu Ala Arg Val Leu Ile
            20                  25                  30

Pro Asn Pro Lys Ala Gln Thr Asp Pro Thr Ala Pro Lys Phe Leu Glu
        35                  40                  45

Lys Arg Gly Asn Lys Gly Val Ser Thr Met Phe Pro Arg Thr Trp Thr
    50                  55                  60

Glu Asp Arg Leu Lys Val Glu Leu Glu His Ala Phe Lys Asn Gly Ile
65                  70                  75                  80

His Asp Lys Gly Gln Val Trp Thr Gly Ile Thr Lys Ser Gly Val Lys
                85                  90                  95

Val Gln Trp Tyr Arg Ser Glu Lys Gly Glu Ile Thr Ser Val His Pro
            100                 105                 110

Ile Leu Glu
        115
```

<210> SEQ ID NO 83
<211> LENGTH: 243
<212> TYPE: DNA
<213> ORGANISM: Pasteurella multocida

<400> SEQUENCE: 83

```
gccgatatgg tacgtgtcga cattatgatc aatggtgagc gtgtcgatgc gttagcgtta     60
atcgtgcata agataatgc accttatcgt ggtcgtgaat tagtggaaaa aatgcgtgag    120
ctcattccac gtcaacaatt tgatattgcg attcaagcgg cgattggtaa ccacattatt    180
gcccgttcta ccgtcaaaca attacgtaaa aacgtattag caaaatgtta tggtggtgac    240
gtg                                                                  243
```

<210> SEQ ID NO 84
<211> LENGTH: 1797
<212> TYPE: DNA
<213> ORGANISM: Pasteurella multocida

<400> SEQUENCE: 84

```
atgaagaata tacgtaactt ttctattatt gcacacattg accacggtaa atcgacactc     60
tctgaccgcc ttattcaaac ttgcggtggc ttatctgatc gtgaaatgga agcccaagtg    120
ttggattcca tggatcttga acgtgaacgt gggattacga tcaaagcaca aagtgtgacc    180
ttaaattaca aagcgaaaga tggcgaaacc tatcaattaa atttcatcga tacgccaggt    240
cacgttgact tctcttatga agtatcgcgt tctttagccg cttgtgaagg cgcattatta    300
gtggtggatg cgggacaagg tgtcgaggca caaactttgg ctaactgcta taccgcaatt    360
gaaatgaatt tagaagtggt gccgatttta aacaaaatcg acttgcccgc ggcagatcct    420
gaacgcgttg cagaagaaat tgaagacatt gtcggtattg acgcgatgga agcggtgcgc    480
tgttcagcaa aaaccggtgt gggtattgaa gatgtgttgg aagaaattgt gcataaaatc    540
cctgcacccg aaggggatcc gaatgcacca ttacaagcct tgattatcga ctcgtggttt    600
gataactact taggcgtagt atctttagtg cgcattaaaa acggcacatt acgcaaaggc    660
gataaaatca aagtgatgtc tacagggcaa tcttacaatg tggatcgtct tggtattttc    720
accccaaaac aagtcgatac caccatttta aattgtggtg aagtgggttg ggtggtgtgc    780
gccattaaag atattttagg ggcacccgtg ggtgatacgc ttacttcgca caacaatcca    840
gcttcttctg tcctgccggg ttttaagaaa gttaagccac aggtgtatgc cggtttattc    900
ccaattagct ctgatgatta tgaagcattc cgtgatgcgc tcggtaaact tagtctaaac    960
gatgcgtcat tattctatga accagaaaac tccaccgcac ttggtttcgg tttccgttgt   1020
ggtttcttag gacttctcca catggagatt attcaagagc gtttagagcg cgaatacgat   1080
cttgatctga ttaccacagc accgacagta gtgtatgaag tggaaaaaac cgacggtgaa   1140
gtgatttatg tggatagccc atcaaaatta ccgccactca acaacattac ggagattcgt   1200
gaaccgattg cagaatgtaa catgctgtta ccacaaacct acttaggtaa cgtcattacg   1260
ctctgtgtag aaaaacgcgg tgtacaaacc aatatggttt accatggtaa ccaagtggca   1320
ttgacctatg aaatcccaat gggcgaagtg gtactggatt tcttcgaccg cttaaaatca   1380
acttctcgtg gttatgcttc cttagattat ggtttcaaac gtttccaagc cgccgatatg   1440
gtacgtgtcg acattatgat caatggtgag cgtgtcgatg cgttagcgtt aatcgtgcat   1500
aaagataatg caccttatcg tggtcgtgaa ttagtggaaa aaatgcgtga gctcattcca   1560
cgtcaacaat ttgatattgc gattcaagcg gcgattggta accacattat tgcccgttct   1620
actgtcaaac aattacgtaa aaacgtatta gcaaaatgtt atggtggtga cgttagccgt   1680
aagaaaaaac tcttacagaa acaaaaagaa ggtaaaaaac gcatgaagtc tttgggtaac   1740
gtcgaagtac cacaagaagc cttcttagcg attttacatg tcggaaaaga caaataa      1797
```

<210> SEQ ID NO 85
<211> LENGTH: 598
<212> TYPE: PRT
<213> ORGANISM: Pasteurella multocida

<400> SEQUENCE: 85

```
Met Lys Asn Ile Arg Asn Phe Ser Ile Ile Ala His Ile Asp His Gly
1               5                   10                  15

Lys Ser Thr Leu Ser Asp Arg Leu Ile Gln Thr Cys Gly Gly Leu Ser
```

```
                     20                  25                  30
Asp Arg Glu Met Glu Ala Gln Val Leu Asp Ser Met Asp Leu Glu Arg
            35                  40                  45

Glu Arg Gly Ile Thr Ile Lys Ala Gln Ser Val Thr Leu Asn Tyr Lys
        50                  55                  60

Ala Lys Asp Gly Glu Thr Tyr Gln Leu Asn Phe Ile Asp Thr Pro Gly
65                  70                  75                  80

His Val Asp Phe Ser Tyr Glu Val Ser Arg Ser Leu Ala Ala Cys Glu
                85                  90                  95

Gly Ala Leu Leu Val Val Asp Ala Gly Gln Gly Val Glu Ala Gln Thr
            100                 105                 110

Leu Ala Asn Cys Tyr Thr Ala Ile Glu Met Asn Leu Glu Val Val Pro
        115                 120                 125

Ile Leu Asn Lys Ile Asp Leu Pro Ala Ala Asp Pro Glu Arg Val Ala
        130                 135                 140

Glu Glu Ile Glu Asp Ile Val Gly Ile Asp Ala Met Glu Ala Val Arg
145                 150                 155                 160

Cys Ser Ala Lys Thr Gly Val Gly Ile Glu Asp Val Leu Glu Glu Ile
                165                 170                 175

Val His Lys Ile Pro Ala Pro Glu Gly Asp Pro Asn Ala Pro Leu Gln
            180                 185                 190

Ala Leu Ile Ile Asp Ser Trp Phe Asp Asn Tyr Leu Gly Val Val Ser
        195                 200                 205

Leu Val Arg Ile Lys Asn Gly Thr Leu Arg Lys Gly Asp Lys Ile Lys
        210                 215                 220

Val Met Ser Thr Gly Gln Ser Tyr Asn Val Asp Arg Leu Gly Ile Phe
225                 230                 235                 240

Thr Pro Lys Gln Val Asp Thr Thr Ile Leu Asn Cys Gly Glu Val Gly
                245                 250                 255

Trp Val Val Cys Ala Ile Lys Asp Ile Leu Gly Ala Pro Val Gly Asp
            260                 265                 270

Thr Leu Thr Ser His Asn Asn Pro Ala Ser Ser Val Leu Pro Gly Phe
        275                 280                 285

Lys Lys Val Lys Pro Gln Val Tyr Ala Gly Leu Phe Pro Ile Ser Ser
        290                 295                 300

Asp Asp Tyr Glu Ala Phe Arg Asp Ala Leu Gly Lys Leu Ser Leu Asn
305                 310                 315                 320

Asp Ala Ser Leu Phe Tyr Glu Pro Glu Asn Ser Thr Ala Leu Gly Phe
                325                 330                 335

Gly Phe Arg Cys Gly Phe Leu Gly Leu Leu His Met Glu Ile Ile Gln
            340                 345                 350

Glu Arg Leu Glu Arg Glu Tyr Asp Leu Asp Leu Ile Thr Thr Ala Pro
        355                 360                 365

Thr Val Val Tyr Glu Val Glu Lys Thr Asp Gly Glu Val Ile Tyr Val
        370                 375                 380

Asp Ser Pro Ser Lys Leu Pro Pro Leu Asn Asn Ile Thr Glu Ile Arg
385                 390                 395                 400

Glu Pro Ile Ala Glu Cys Asn Met Leu Leu Pro Gln Thr Tyr Leu Gly
                405                 410                 415

Asn Val Ile Thr Leu Cys Val Glu Lys Arg Gly Val Gln Thr Asn Met
            420                 425                 430

Val Tyr His Gly Asn Gln Val Ala Leu Thr Tyr Glu Ile Pro Met Gly
        435                 440                 445
```

-continued

Glu Val Val Leu Asp Phe Phe Asp Arg Leu Lys Ser Thr Ser Arg Gly
    450                 455                 460

Tyr Ala Ser Leu Asp Tyr Gly Phe Lys Arg Phe Gln Ala Ala Asp Met
465                 470                 475                 480

Val Arg Val Asp Ile Met Ile Asn Gly Glu Arg Val Asp Ala Leu Ala
                485                 490                 495

Leu Ile Val His Lys Asp Asn Ala Pro Tyr Arg Gly Arg Glu Leu Val
            500                 505                 510

Glu Lys Met Arg Glu Leu Ile Pro Arg Gln Gln Phe Asp Ile Ala Ile
        515                 520                 525

Gln Ala Ala Ile Gly Asn His Ile Ile Ala Arg Ser Thr Val Lys Gln
    530                 535                 540

Leu Arg Lys Asn Val Leu Ala Lys Cys Tyr Gly Gly Asp Val Ser Arg
545                 550                 555                 560

Lys Lys Lys Leu Leu Gln Lys Gln Lys Glu Gly Lys Lys Arg Met Lys
                565                 570                 575

Ser Leu Gly Asn Val Glu Val Pro Gln Glu Ala Phe Leu Ala Ile Leu
            580                 585                 590

His Val Gly Lys Asp Lys
        595

<210> SEQ ID NO 86
<211> LENGTH: 147
<212> TYPE: DNA
<213> ORGANISM: Pasteurella multocida

<400> SEQUENCE: 86
aaaagttcga cttccgtaat cggtttttta gttaattgtt caatattgcg taataaacga 60
cgttctcttg gttcaacaaa taacaatgca cgccctgtac gtccggcacg ccctgtacga 120
ccaatacggt ggacataaga ctcagca 147

<210> SEQ ID NO 87
<211> LENGTH: 1833
<212> TYPE: DNA
<213> ORGANISM: Pasteurella multocida

<400> SEQUENCE: 87
atgactgaaa caacaatgac tttcaatgat ttaggcttgc ctgaatttct tcttaacgcc 60
gtctctgact taggctttga aacccccttct ccaattcaac aaagttgtat cccaaacctg 120
ttaaatgggc atgatgtgct aggtatggca caaactggaa gtggtaaaac cgccgccttt 180
tcactccctt tattagcaca aattgattta gataaaaaat atccacaaat gttagtgatg 240
gcaccgacac gtgagttagc catccaagta gcagatgcct gtgagcactt ttgcaaatat 300
gcgaaaaata ccaatattgt taccctttat ggtggtcaac gctatgacat tcaattgcgt 360
gctttacgcc aaggtgctca ggttgtagtg ggacacctg gtcgtatttt agatcacatt 420
cgtcgtggca ctttagattt gtctaattta cgttttatgg tgttagatga agcggacgaa 480
atgttacgta tgggctttat tgatgatgtt gaaacggtga tggcagaatt accagaacaa 540
catcagactg cacttttctc agccaccatg ccagatccaa ttcgtcgtat tactaagcgt 600
tttatgaaag atccgaaaga gattaaaatt aaatcgacgc aaacgacgaa tccagatatt 660
acacagagtt gttggtatgt gcatggtttc cgtaaaaatg atgccttatt acgtttctta 720
gaagtagaaa aatttgatgc cgcgattatc tttactcgta ctaaaacggg gacattagat 780

-continued

```
gtaacggaat tgttggaaaa acatggtttc cgtgccgcag cattaaatgg cgatatgaca      840
caacaattac gtgaacaaac gcttgatcgt ttaagaaatg gtagtttaga tatccttgtg      900
gcaaccgatg tggcggcgcg tggtttagat gtggagcgca ttagcctcgt agtgaactat      960
gatattccat tagatgctga gtcttatgtt caccgtattg gtcgtacagg gcgtgcagga     1020
cgtacagggc gtgcattgtt atttgttgaa ccaagagaac gtcgtttatt acgtaatatt     1080
gaacaattaa ctaaaaaacc gattacggaa gtcgaagtgc caaatcatga ggtactacaa     1140
gcttgtcgcc gtgagaaatt taaagccaaa attacagtcc aattagagca tcatgattta     1200
ggactttatc gtagcttact agaagatatg ttcaccgcgg atcaagatca ggaagatatt     1260
gcggcggcga tgttgatgtt gttgcaaggt aaacaaaagc ttatttttacc agccgatcca     1320 attattgatc gtaaaacttc acgtggtgat cgtggcgagc gtcgtgaacg tggtggacgt     1380
gaaaatccac gttcagcaga gcgtcgtggt tacggtacac cgcaggcgat ggatttatat     1440
cgtattgaag taggacgttt agatggcgcg gaagtccgtc atattgttgg ggcgattgcc     1500
aatgaaggtg atatcaatag tcgttatatt ggtcatatta aattatatga tgattacacc     1560
acgattgaat taccacaagg tatgccgaaa gaattattag gtgtatttgc gaaaacacgc     1620
gtgatgaaca aacaaatgca gatgtcattt gtgggagcgt ctaatgcagg ttcaagccgt     1680
gatcgcgatg atttcgctga ccgccgtggt ggaaaacgta aaggacgcgg cgatgaacca     1740
cgttttgggc gtgaagatcg taaatttaaa gaaaaaagtc agcgcacttt taatgatcgc     1800
ccacgcagag aaagacgtga acgccaaaag taa                                  1833
```

<210> SEQ ID NO 88
<211> LENGTH: 610
<212> TYPE: PRT
<213> ORGANISM: Pasteurella multocida

<400> SEQUENCE: 88

```
Met Thr Glu Thr Thr Met Thr Phe Asn Asp Leu Gly Leu Pro Glu Phe
1               5                   10                  15

Leu Leu Asn Ala Val Ser Asp Leu Gly Phe Glu Thr Pro Ser Pro Ile
            20                  25                  30

Gln Gln Ser Cys Ile Pro Asn Leu Leu Asn Gly His Asp Val Leu Gly
        35                  40                  45

Met Ala Gln Thr Gly Ser Gly Lys Thr Ala Ala Phe Ser Leu Pro Leu
    50                  55                  60

Leu Ala Gln Ile Asp Leu Asp Lys Lys Tyr Pro Gln Met Leu Val Met
65                  70                  75                  80

Ala Pro Thr Arg Glu Leu Ala Ile Gln Val Ala Asp Ala Cys Glu His
                85                  90                  95

Phe Cys Lys Tyr Ala Lys Asn Thr Asn Ile Val Thr Leu Tyr Gly Gly
            100                 105                 110

Gln Arg Tyr Asp Ile Gln Leu Arg Ala Leu Arg Gln Gly Ala Gln Val
        115                 120                 125

Val Val Gly Thr Pro Gly Arg Ile Leu Asp His Ile Arg Arg Gly Thr
    130                 135                 140

Leu Asp Leu Ser Asn Leu Arg Phe Met Val Leu Asp Glu Ala Asp Glu
145                 150                 155                 160

Met Leu Arg Met Gly Phe Ile Asp Asp Val Glu Thr Val Met Ala Glu
                165                 170                 175

Leu Pro Glu Gln His Gln Thr Ala Leu Phe Ser Ala Thr Met Pro Asp
            180                 185                 190
```

```
Pro Ile Arg Arg Ile Thr Lys Arg Phe Met Lys Asp Pro Lys Glu Ile
        195                 200                 205

Lys Ile Lys Ser Thr Gln Thr Thr Asn Pro Asp Ile Thr Gln Ser Cys
        210                 215                 220

Trp Tyr Val His Gly Phe Arg Lys Asn Asp Ala Leu Leu Arg Phe Leu
225                 230                 235                 240

Glu Val Glu Lys Phe Asp Ala Ile Ile Phe Thr Arg Thr Lys Thr
                245                 250                 255

Gly Thr Leu Asp Val Thr Glu Leu Leu Glu Lys His Gly Phe Arg Ala
        260                 265                 270

Ala Ala Leu Asn Gly Asp Met Thr Gln Gln Leu Arg Glu Gln Thr Leu
        275                 280                 285

Asp Arg Leu Arg Asn Gly Ser Leu Asp Ile Leu Val Ala Thr Asp Val
        290                 295                 300

Ala Ala Arg Gly Leu Asp Val Glu Arg Ile Ser Leu Val Val Asn Tyr
305                 310                 315                 320

Asp Ile Pro Leu Asp Ala Glu Ser Tyr Val His Arg Ile Gly Arg Thr
                325                 330                 335

Gly Arg Ala Gly Arg Thr Gly Arg Ala Leu Leu Phe Val Glu Pro Arg
        340                 345                 350

Glu Arg Arg Leu Leu Arg Asn Ile Glu Gln Leu Thr Lys Lys Pro Ile
        355                 360                 365

Thr Glu Val Glu Val Pro Asn His Glu Val Leu Gln Ala Cys Arg Arg
        370                 375                 380

Glu Lys Phe Lys Ala Lys Ile Thr Val Gln Leu Glu His His Asp Leu
385                 390                 395                 400

Gly Leu Tyr Arg Ser Leu Leu Glu Asp Met Phe Thr Ala Asp Gln Asp
                405                 410                 415

Gln Glu Asp Ile Ala Ala Ala Met Leu Met Leu Leu Gln Gly Lys Gln
        420                 425                 430

Lys Leu Ile Leu Pro Ala Asp Pro Ile Ile Asp Arg Lys Thr Ser Arg
        435                 440                 445

Gly Asp Arg Gly Glu Arg Arg Glu Arg Gly Gly Arg Glu Asn Pro Arg
        450                 455                 460

Ser Ala Glu Arg Arg Gly Tyr Gly Thr Pro Gln Ala Met Asp Leu Tyr
465                 470                 475                 480

Arg Ile Glu Val Gly Arg Leu Asp Gly Ala Glu Val Arg His Ile Val
                485                 490                 495

Gly Ala Ile Ala Asn Glu Gly Asp Ile Asn Ser Arg Tyr Ile Gly His
        500                 505                 510

Ile Lys Leu Tyr Asp Asp Tyr Thr Thr Ile Glu Leu Pro Gln Gly Met
        515                 520                 525

Pro Lys Glu Leu Leu Gly Val Phe Ala Lys Thr Arg Val Met Asn Lys
        530                 535                 540

Gln Met Gln Met Ser Phe Val Gly Ala Ser Asn Ala Gly Ser Ser Arg
545                 550                 555                 560

Asp Arg Asp Asp Phe Ala Asp Arg Gly Gly Lys Arg Lys Gly Arg
                565                 570                 575

Gly Asp Glu Pro Arg Phe Gly Arg Glu Asp Arg Lys Phe Lys Glu Lys
        580                 585                 590

Ser Gln Arg Thr Phe Asn Asp Arg Pro Arg Arg Glu Arg Arg Glu Arg
        595                 600                 605
```

Gln Lys
    610

<210> SEQ ID NO 89
<211> LENGTH: 187
<212> TYPE: DNA
<213> ORGANISM: Pasteurella multocida

<400> SEQUENCE: 89

| tctacgttaa | cgccacccgt | tgtattaata | acattggcaa | agccagaagc | agcgatcatc | 60 |
| acaaaaccaa | tcatcgccat | taaacgtaag | ccttgttgga | aaatgtcatt | actttctttt | 120 |
| aatttgaaaa | taccacaaac | agcaaaaata | atcagaccgg | ctaatccacc | aataatagtt | 180 |
| gaactct | | | | | | 187 |

<210> SEQ ID NO 90
<211> LENGTH: 1359
<212> TYPE: DNA
<213> ORGANISM: Pasteurella multocida

<400> SEQUENCE: 90

| atgttattaa | ctaaccctgt | cgtgatttcc | attgtggttc | tacttgcgct | cagtttattg | 60 |
| cgtattaatg | ttgtcatcgc | actcgttatt | tccgcattag | tggcaggttt | aactggcaat | 120 |
| ttgggcgtca | gtgaaacaat | aaaaacgttt | acgaatggac | taggcggagg | tgcagaggtc | 180 |
| gccatgaatt | atgcgatttt | aggcgcgttt | gcggttgcca | tttcaaaatc | aggcattact | 240 |
| gatttacttg | cctataaagt | cattaaacgt | ttgggcaata | caccaagcag | tcgctcaatg | 300 |
| gcgggtttta | atatttat | cttaacaatc | ctcacgctgt | tgccgtttc | atcgcaaaac | 360 |
| ttattacctg | tccatatcgc | gtttattcct | attgtgattc | cccgcttct | tgcgattttc | 420 |
| aataaactaa | aattggatcg | tcgtgccgtt | gcttgtgttt | taacttttgg | tttaaccgcc | 480 |
| acttatatgt | tattaccagt | agggtttggg | aaaattttta | ttgaaagtat | cctcgttaag | 540 |
| aatatcaatc | aagccggcgc | gactttaggc | ttacagacat | ctgtggctga | agtgtcatta | 600 |
| gctatggcag | tccagtgat | tggcatgatt | cttggtttac | tgacagcgat | ctttattagc | 660 |
| tatcgtaaac | cgagagaata | tgccatgatg | cgcagcgaaa | tcagcacgca | agatattgaa | 720 |
| tcacatgttg | ctcaaatcaa | gccgttccat | gtcggcgcaa | gttagtggc | aatcattgtt | 780 |
| acttttgccc | ttcagctctt | taccagttca | accattattg | gtggattagc | cggtctgatt | 840 |
| attttgctg | tttgtggtat | tttcaaatta | aaagaaagta | atgacatttt | ccaacaaggc | 900 |
| ttacgtttaa | tggcgatgat | tggttttgtg | atgatcgctg | cttctggctt | tgccaatgtt | 960 |
| attaatacaa | cgggtggtgt | aacggcgtta | gttgaaaccct | tcagtcaagg | ttttggcgca | 1020 |
| gaaaataaag | ggattgcagc | ctttttaatg | ctgttagttg | gcttatttat | tactatgggg | 1080 |
| attggctcat | cattctcaac | ggtacctatt | attgcctcta | tttatgtacc | actttgtctt | 1140 |
| tctcttggtt | tctcacctt | agcaacggtt | tcgcttattg | gggtatccgc | tgcgcttggt | 1200 |
| gatgcgggtt | cgcctgcctc | tgactcaaca | ttaggaccaa | cctcgggttt | aaatgcagat | 1260 |
| ggtaaacatg | atcatatttg | ggattctgtc | gtcccaacat | ttatccatta | taatatccca | 1320 |
| ctcattcttt | tcggttggtt | agccgccatg | tatctgtaa | | | 1359 |

<210> SEQ ID NO 91
<211> LENGTH: 452
<212> TYPE: PRT
<213> ORGANISM: Pasteurella multocida

<400> SEQUENCE: 91

| | | | | | | | | | | | | | | |
|---|---|---|---|---|---|---|---|---|---|---|---|---|---|---|
|Met|Leu|Leu|Thr|Asn|Pro|Val|Val|Ile|Ser|Ile|Val|Leu|Leu|Ala|
|1| | | |5| | | |10| | | |15| | |

| | | | | | | | | | | | | | | |
|---|---|---|---|---|---|---|---|---|---|---|---|---|---|---|
|Leu|Ser|Leu|Leu|Arg|Ile|Asn|Val|Val|Ile|Ala|Leu|Val|Ile|Ser|Ala|
| | | | |20| | | |25| | | |30| | |

| | | | | | | | | | | | | | | |
|---|---|---|---|---|---|---|---|---|---|---|---|---|---|---|
|Leu|Val|Ala|Gly|Leu|Thr|Gly|Asn|Leu|Gly|Val|Ser|Glu|Thr|Ile|Lys|
| | | |35| | | |40| | | |45| | | |

Thr Phe Thr Asn Gly Leu Gly Gly Ala Glu Val Ala Met Asn Tyr
           50                  55                  60

Ala Ile Leu Gly Ala Phe Ala Val Ala Ile Ser Lys Ser Gly Ile Thr
65                  70                  75                  80

Asp Leu Leu Ala Tyr Lys Val Ile Lys Arg Leu Gly Asn Thr Pro Ser
                85                  90                  95

Ser Arg Ser Met Ala Gly Phe Lys Tyr Phe Ile Leu Thr Ile Leu Thr
            100                 105                 110

Leu Phe Ala Val Ser Ser Gln Asn Leu Leu Pro Val His Ile Ala Phe
            115                 120                 125

Ile Pro Ile Val Ile Pro Pro Leu Leu Ala Ile Phe Asn Lys Leu Lys
            130                 135                 140

Leu Asp Arg Arg Ala Val Ala Cys Val Leu Thr Phe Gly Leu Thr Ala
145                 150                 155                 160

Thr Tyr Met Leu Leu Pro Val Gly Phe Gly Lys Ile Phe Ile Glu Ser
                165                 170                 175

Ile Leu Val Lys Asn Ile Asn Gln Ala Gly Ala Thr Leu Gly Leu Gln
            180                 185                 190

Thr Ser Val Ala Glu Val Ser Leu Ala Met Ala Val Pro Val Ile Gly
            195                 200                 205

Met Ile Leu Gly Leu Leu Thr Ala Ile Phe Ile Ser Tyr Arg Lys Pro
210                 215                 220

Arg Glu Tyr Ala Met Met Arg Ser Glu Ile Ser Thr Gln Asp Ile Glu
225                 230                 235                 240

Ser His Val Ala Gln Ile Lys Pro Phe His Val Gly Ala Ser Leu Val
                245                 250                 255

Ala Ile Ile Val Thr Phe Ala Leu Gln Leu Phe Thr Ser Ser Thr Ile
            260                 265                 270

Ile Gly Gly Leu Ala Gly Leu Ile Ile Phe Ala Val Cys Gly Ile Phe
            275                 280                 285

Lys Leu Lys Glu Ser Asn Asp Ile Phe Gln Gln Gly Leu Arg Leu Met
290                 295                 300

Ala Met Ile Gly Phe Val Met Ile Ala Ala Ser Gly Phe Ala Asn Val
305                 310                 315                 320

Ile Asn Thr Thr Gly Gly Val Thr Ala Leu Val Glu Thr Phe Ser Gln
                325                 330                 335

Gly Phe Gly Ala Glu Asn Lys Gly Ile Ala Ala Phe Leu Met Leu Leu
            340                 345                 350

Val Gly Leu Phe Ile Thr Met Gly Ile Gly Ser Ser Phe Ser Thr Val
            355                 360                 365

Pro Ile Ile Ala Ser Ile Tyr Val Pro Leu Cys Leu Ser Leu Gly Phe
            370                 375                 380

Ser Pro Leu Ala Thr Val Ser Leu Ile Gly Val Ser Ala Ala Leu Gly
385                 390                 395                 400

Asp Ala Gly Ser Pro Ala Ser Asp Ser Thr Leu Gly Pro Thr Ser Gly
                405                 410                 415

Leu Asn Ala Asp Gly Lys His Asp His Ile Trp Asp Ser Val Val Pro
        420                 425                 430

Thr Phe Ile His Tyr Asn Ile Pro Leu Ile Leu Phe Gly Trp Leu Ala
        435                 440                 445

Ala Met Tyr Leu
    450

<210> SEQ ID NO 92
<211> LENGTH: 1391
<212> TYPE: DNA
<213> ORGANISM: Pasteurella multocida

<400> SEQUENCE: 92

| | | | | |
|---|---|---|---|---|
| ctctagatag | aggagcttat | atatttactt | aagaataagt | tgctggtaaa tattcgttgt | 60 |
| gtttctcttt | taagtactca | tcaacactat | tatgatcaac | gttataagac aattgttctt | 120 |
| tgtaaaaatc | taatcttgct | cttgcattat | taataaattc | agcccaagtc atcacaataa | 180 |
| cttctacatt | gtactctaga | tcgtctgata | ccacaccttt | acgctttcct cgttgattgg | 240 |
| attctcgttt | tgcgaattgg | tcaagctcat | ttgaaactgc | tataaatgtc cactttgttt | 300 |
| tactatgatc | gaatcgttca | tcagatgaca | ctgcgtaagc | atagttttta atttgagtaa | 360 |
| ttacttcaga | attaattttc | tgacttggac | gctttaattc | tacaactaaa tattctttat | 420 |
| aaccttggct | aggctttctt | gctttatgaa | aaaataaatc | aactcttcct tgttttccat | 480 |
| cagaaagaaa | tactggttta | tctgcatcaa | aactatcttt | atcataataa tctaaatgtg | 540 |
| ttgcatgaat | ctttaaaaca | tcatttagtg | tattttcact | tcctgaaaaa ttaaaatctt | 600 |
| ccataaaaac | ccaagtttca | ttttctaaga | ttttatgtaa | ctgatctctt tccaaaagag | 660 |
| cttttttatt | ctctttatca | aaagaagat | tttctaatcc | tttcaaaaaa ttaagtctat | 720 |
| ctgcaactat | ctttgaagaa | cggattatag | atgttagaga | tgtattctct aataatttag | 780 |
| aaaacatttc | cttctcgtta | tcattcaatt | ttaataacctc | ttccagaatt ctttgcattg | 840 |
| atgctggatt | ctcttttatc | gcattagata | gcaattggaa | agttaatctc tttgattcaa | 900 |
| tagaactaga | gctaaatcta | ggtaggttat | cctcaaccett | aacagctacg atcaaaaaa | 960 |
| gatttttttc | tatttttca | acggatgtat | attcgtttgc | tacatacgga taaatatcca | 1020 |
| aatctatcca | agatttattt | cttttttgcat | tttcttcttc | tctttgttgt ctaagatatt | 1080 |
| catttaattt | tgttattgct | tctgtaataa | gttttctcgc | attttcatcc atatcaacta | 1140 |
| tgctcaaatt | atcactttca | tttaagctgt | taatagtctc | tccacataaa tagacagtat | 1200 |
| agttatatcc | ttgctttcta | attctatttt | tagtgtcata | atcacaaatg aaggaataat | 1260 |
| tctctttgca | tagataaaaa | tctgaaacat | cttttcttatc | ccaaagaata attttcattt | 1320 |
| tcccatgaat | atcagactct | tcacctaaaa | taatttcagt | ttcagtgtta attaattctc | 1380 |
| gagggtctag | a | | | | 1391 |

<210> SEQ ID NO 93
<211> LENGTH: 1290
<212> TYPE: DNA
<213> ORGANISM: Pasteurella multocida

<400> SEQUENCE: 93

| | | | | |
|---|---|---|---|---|
| ttaagaataa | gttgctggta | aatattcgtt | gtgtttctct | tttaagtact catcaacact | 60 |
| attatgatca | acgttataag | acaattgttc | tttgtaaaaa | tctaatcttg ctcttgcatt | 120 |
| attaataatt | tcagcccaag | tcatcacaat | aacttctaca | ttgtactcta gatcgtctga | 180 |

-continued

```
taccacacct ttacgctttc ctcgttgatt ggattctcgt tttgcgaatt ggtcaagctc      240
atttgaaact gctataaatg tccactttgt tttactatga tcgaatcgtt catcagatga      300
cactgcgtaa gcatagtttt taatttgagt aattacttca gaattaattt tctgacttgg      360
acgctttaat tctacaacta atattcttt ataaccttgg ctaggctttc ttgctttatg       420
aaaaaataaa tcaactcttc cttgttttcc atcagaaaga aatactggtt tatctgcatc      480
aaaactatct ttatcataat aatctaaatg tgttgcatga atctttaaaa catcatttag      540
tgtattttca cttcctgaaa aattaaaatc ttccataaaa acccaagttt cattttctaa      600
gattttatgt aactgatctc tttccaaaag agcttttta ttctctttat caaaaagaag       660
attttctaat cctttcaaaa aattaagtct atctgcaact atctttgaag aacggattat      720
agatgttaga gatgtattct ctaataattt agaaaacatt tccttctcgt tatcattcaa      780
ttttaatacc tcttccagaa ttctttgcat tgatgctgga ttctctttta tcgcattaga      840
tagcaattgg aaagttaatc tctttgattc aatagaacta gagctaaatc taggtaggtt      900
atcctcaacc ttaacagcta cgatatcaaa aagattttt tctatttttt caacggatgt       960
atattcgttt gctacatacg gataaatatc caaatctatc caagattta ttcttttgc      1020 attttcttct tctctttgtt gtctaagata ttcatttaat tttgttattg cttctgtaat    1080 aagtttctc gcattttcat ccatatcaac tatgctcaaa ttatcacttt catttaagct    1140
gttaatagtc tctccacata aatagacagt atagttatat ccttgctttc taattctatt   1200
tttagtgtca aatcacaaa tgaaggaata attctctttg catagataaa aatctgaaac   1260
atctttctta tcccaaagaa taattttcat                                     1290
```

<210> SEQ ID NO 94
<211> LENGTH: 429
<212> TYPE: PRT
<213> ORGANISM: Pasteurella multocida

<400> SEQUENCE: 94

Met Lys Ile Ile Leu Trp Asp Lys Lys Asp Val Ser Asp Phe Tyr Leu
1               5                   10                  15

Cys Lys Glu Asn Tyr Ser Phe Ile Cys Asp Tyr Asp Thr Lys Asn Arg
            20                  25                  30

Ile Arg Lys Gln Gly Tyr Asn Tyr Thr Val Tyr Leu Cys Gly Glu Thr
        35                  40                  45

Ile Asn Ser Leu Asn Glu Ser Asp Asn Leu Ser Ile Val Asp Met Asp
    50                  55                  60

Glu Asn Ala Arg Lys Leu Ile Thr Glu Ala Ile Thr Lys Leu Asn Glu
65                  70                  75                  80

Tyr Leu Arg Gln Gln Arg Glu Glu Asn Ala Lys Arg Ile Lys Ser
                85                  90                  95

Trp Ile Asp Leu Asp Ile Tyr Pro Tyr Val Ala Asn Glu Tyr Thr Ser
            100                 105                 110

Val Glu Lys Ile Glu Lys Asn Leu Phe Asp Ile Ala Val Lys Val
        115                 120                 125

Glu Asp Asn Leu Pro Arg Phe Ser Ser Ser Ile Glu Ser Lys Arg
    130                 135                 140

Leu Thr Phe Gln Leu Leu Ser Asn Ala Ile Lys Glu Asn Pro Ala Ser
145                 150                 155                 160

Met Gln Arg Ile Leu Glu Glu Val Leu Lys Leu Asn Asp Asn Glu Lys
                165                 170                 175

```
Glu Met Phe Ser Lys Leu Leu Glu Asn Thr Ser Leu Thr Ser Ile Ile
            180                 185                 190

Arg Ser Ser Lys Ile Val Ala Asp Arg Leu Asn Phe Leu Lys Gly Leu
        195                 200                 205

Glu Asn Leu Leu Phe Asp Lys Glu Asn Lys Lys Ala Leu Leu Glu Arg
    210                 215                 220

Asp Gln Leu His Lys Ile Leu Glu Asn Glu Thr Trp Val Phe Met Glu
225                 230                 235                 240

Asp Phe Asn Phe Ser Gly Ser Glu Asn Thr Leu Asn Asp Val Leu Lys
                245                 250                 255

Ile His Ala Thr His Leu Asp Tyr Tyr Asp Lys Asp Ser Phe Asp Ala
            260                 265                 270

Asp Lys Pro Val Phe Leu Ser Asp Gly Lys Gln Gly Arg Val Asp Leu
        275                 280                 285

Phe Phe His Lys Ala Arg Lys Pro Ser Gln Gly Tyr Lys Glu Tyr Leu
    290                 295                 300

Val Val Glu Leu Lys Arg Pro Ser Gln Lys Ile Asn Ser Glu Val Ile
305                 310                 315                 320

Thr Gln Ile Lys Asn Tyr Ala Tyr Ala Val Ser Ser Asp Glu Arg Phe
                325                 330                 335

Asp His Ser Lys Thr Lys Trp Thr Phe Ile Ala Val Ser Asn Glu Leu
            340                 345                 350

Asp Gln Phe Ala Lys Arg Glu Ser Asn Gln Arg Gly Lys Arg Lys Gly
        355                 360                 365

Val Val Ser Asp Asp Leu Glu Tyr Asn Val Glu Val Ile Val Met Thr
    370                 375                 380

Trp Ala Glu Ile Ile Asn Asn Ala Arg Ala Arg Leu Asp Phe Tyr Lys
385                 390                 395                 400

Glu Gln Leu Ser Tyr Asn Val Asp His Asn Ser Val Asp Glu Tyr Leu
                405                 410                 415

Lys Glu Lys His Asn Glu Tyr Leu Pro Ala Thr Tyr Ser
            420                 425

<210> SEQ ID NO 95
<211> LENGTH: 101
<212> TYPE: DNA
<213> ORGANISM: Pasteurella multocida

<400> SEQUENCE: 95
cttatttaag cggttttttt acccaacgct tgaaaatgtt ctctccattt gtcacatgga      60
aaaaggagag aacatgtatt ttagaatggg gatataaagc a                        101

<210> SEQ ID NO 96
<211> LENGTH: 220
<212> TYPE: DNA
<213> ORGANISM: Pasteurella multocida

<400> SEQUENCE: 96
ctttttcctg aagtaataca tcttgagaaa gaattaagtt ttctaaacga gaaggctgat      60
tgatatcata ataaatacca atatcatcgt acactaatga gaaaggtgga tacccatcca     120
cacccagtcc aatagaacgt aaaaaaccat cttctatcgt cgcataaggt aaatcatgtt     180
gttgtgcaaa atgcctcgct ttctttgatg atgctttata                          220

<210> SEQ ID NO 97
```

```
<211> LENGTH: 546
<212> TYPE: DNA
<213> ORGANISM: Pasteurella multocida
<220> FEATURE:
<221> NAME/KEY: modified_base
<222> LOCATION: (529)
<223> OTHER INFORMATION: a, t, c, g, other or unknown
<220> FEATURE:
<221> NAME/KEY: modified_base
<222> LOCATION: (532)
<223> OTHER INFORMATION: a, t, c, g, other or unknown
<220> FEATURE:
<221> NAME/KEY: modified_base
<222> LOCATION: (535)
<223> OTHER INFORMATION: a, t, c, g, other or unknown
<220> FEATURE:
<221> NAME/KEY: modified_base
<222> LOCATION: (538)
<223> OTHER INFORMATION: a, t, c, g, other or unknown
<220> FEATURE:
<221> NAME/KEY: modified_base
<222> LOCATION: (543)
<223> OTHER INFORMATION: a, t, c, g, other or unknown

<400> SEQUENCE: 97
gactttgtca tcatcgcaac gccaacagac tataataccg aaacaggtta ttttaataca      60
tccactgttg aagctgtcat tgaacaaacc ctttcaatca atccacaagc aacgattatt     120
ataaaatcaa cgattcccgt tggttttacc gaaaaaatgc gtgagaaatt tcataccaag     180
aacattattt tttctcctga gttttaaga aaggaaaag cacttcatga caatttgttt       240
ccaagcagaa ttattgttgg cagtacttct tatcaagcaa aagtatttgc cgatatgttg     300
acacagtgtg ccagaaaaaa agatgtaact gttttattta cacacaatac tgaggctgaa    360
gctgttaaat tatttgcaaa tacgtatctc gcaatgcgag ttgccttttc taatgaatta    420
gatacttatg cgagtcttca ccatttaaat acaaaagaca ttatcaatgg tatttctact    480
gatcctcgca ttggtacaca ctacaataac ccaagtttcg gctatggcng tnatngtnta    540 ccnaag                                                                546

<210> SEQ ID NO 98
<211> LENGTH: 20
<212> TYPE: DNA
<213> ORGANISM: Pasteurella multocida

<400> SEQUENCE: 98
atctgatcct tcaactcagc                                                  20

<210> SEQ ID NO 99
<211> LENGTH: 19
<212> TYPE: DNA
<213> ORGANISM: Pasteurella multocida

<400> SEQUENCE: 99
cgcagggctt tattgattc                                                   19

<210> SEQ ID NO 100
<211> LENGTH: 27
<212> TYPE: DNA
<213> ORGANISM: Pasteurella multocida

<400> SEQUENCE: 100
gcggaattcg atgaatgttc cgttgcg                                          27

<210> SEQ ID NO 101
<211> LENGTH: 20
```

```
<212> TYPE: DNA
<213> ORGANISM: Pasteurella multocida

<400> SEQUENCE: 101
tttaccaaaa tcattagggg                                              20

<210> SEQ ID NO 102
<211> LENGTH: 19
<212> TYPE: DNA
<213> ORGANISM: Pasteurella multocida

<400> SEQUENCE: 102
gatcatatga caagatgtg                                               19

<210> SEQ ID NO 103
<211> LENGTH: 35
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)..(30)
<223> OTHER INFORMATION: a, t, c, g, other or unknown

<400> SEQUENCE: 103
ggccacgcgt cgactagtac nnnnnnnnnn gatat                             35

<210> SEQ ID NO 104
<211> LENGTH: 35
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)..(30)
<223> OTHER INFORMATION: a, t, c, g, other or unknown

<400> SEQUENCE: 104
ggccacgcgt cgactagtac nnnnnnnnnn cagcc                             35

<210> SEQ ID NO 105
<211> LENGTH: 20
<212> TYPE: DNA
<213> ORGANISM: Pasteurella multocida

<400> SEQUENCE: 105
ggccacgcgt cgactagtac                                              20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 106
tacgttaacg ccacccgttg                                              20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 107
gcttccatac cttgtgaacc                                          20

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 108
gggtgtacgc cttctgctg                                           19

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 109
attgcagtca ttgcggatgc                                          20

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 110
cgatatggta cgtgtcgac                                           19

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 111
aaaaggcgga cctaagtccg                                          20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 112
ccgacaacat gacaatggag                                          20

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 113
tttgcagtgg cttaccgtc                                           19

<210> SEQ ID NO 114
<211> LENGTH: 19
```

```
-continued

<212> TYPE: DNA
<213> ORGANISM: Artificial Sequence
<220> FEATURE:
<223> OTHER INFORMATION: Description of Artificial Sequence: Primer

<400> SEQUENCE: 114
cctgacgacc aatacggtg                                                    19

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 115
ggatggtctg atcctaatgc                                                   20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 116
cgttcatcag atgacactgc                                                   20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 117
gtgattacgg gattatcggg                                                   20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 118
tgaagtggta acgaggcttg                                                   20
```

What is claimed is:

1. A mutant of a gram negative bacterium belonging to the family Pasteurellaceae having a mutation in a nucleotide sequence, wherein the nucleotide sequence prior to mutation consists essentially of SEQ ID NO. 37 and encodes a polypeptide, and wherein the mutation attenuates virulence of the bacterium.

2. The mutant of claim 1, wherein the gram negative bacterium belongs to the genera *Pasteurella, Actinobacillus,* or *Haemophilus.*

3. The mutant of claim 2, wherein the gram negative bacterium is: *Pasteurella multocida, Pasteurella multocida P*-1059, *Pasteurella multocida* PM70, *Pasteurella haemolytica, Pasteurella anatipestifer* or *Actinobacillus pleuropneumoniae.*

4. The mutant of claim 3, wherein the gram negative bacterium is *Pasteurella multocida.*

5. The mutant of claim 1, wherein the mutation is obtained by transposon insertion into the nucleotide sequence, directed mutagenesis of the nucleotide sequence, or homologous recombination.

6. The mutant of claim 5, wherein the mutation obtained by directed mutagenesis or homologous recombination is a result of a deletion, insertion, or substitution of at least one nucleotide of the nucleotide sequence.

7. The mutant of claim 6, wherein the mutation is an insertion between nucleotides that correspond to positions 1411-1412 in SEQ ID NO. 37.

8. The mutant of claim 1, which further comprises at least one heterologous nucleic acid sequence.

9. The mutant of claim 8 wherein the at least one heterologous nucleic acid sequence codes for an immunogen, antigen or epitope from a pathogenic viral, parasitic or bacterial agent, a therapeutic protein, an allergen, a growth factor, a cytokine, an immunomodulator, or an immunostimulator.

10. An immunogenic composition or vaccine comprising the mutant according to claim 1, and a pharmaceutically or veterinarily acceptable diluent, carrier, vehicle or excipient.

11. The immunogenic composition or vaccine of claim 10 further comprising an adjuvant.

12. An immunogenic composition or vaccine comprising the mutant according to claim 9, and a pharmaceutically or veterinarily acceptable diluent, carrier, vehicle or excipient.

13. The immunogenic composition or vaccine of claim 12 further comprising an adjuvant.

14. The mutant of claim 1, wherein the mutant is mutant 4G11 available under the accession number CNCM I-2999 or is a bacterium having all the identifying characteristics thereof, wherein mutant 4G11 comprises a mutation in SEQ ID NO: 37.

15. A mutant gram negative bacterium having a mutation in a nucleotide sequence wherein the nucleotide sequence prior to mutation is identified as SEQ ID NO: 37 and encodes a polypeptide, and wherein the bacterium further comprises at least one heterolgous nucleic acid sequence.

16. The mutant of claim 15 which is a gram negative bacterium belonging to the family Pasteurellaceae.

17. The mutant of claim 15, wherein the gram negative bacterium is: *Pasteurella multocida, Pasteurella haemolytica, Pasteurella anatipestifer* or *Actinobacillus pleuropneumoniae.*

18. The mutant of claim 15, wherein the gram negative bacterium is *Pasteurella multocida.*

19. The mutant of claim 15 wherein the at least one heterologous nucleic acid sequence codes for an immunogen, antigen or epitope from a pathogenic viral, parasitic or bacterial agent, a therapeutic protein, an allergen, a growth factor a cytokine, an immunomodulator, or an immunostimulator.

20. An immunogenic composition or vaccine comprising the mutant according to claim 15, and a pharmaceutically or veterinarily acceptable diluent, carrier, vehicle or excipient.

21. The immunogenic composition or vaccine of claim 20 further comprising an adjuvant.

22. The mutant of claim 1, wherein the mutation occurs in a regulatory sequence that controls the expression of the nucleotide sequence, wherein the regulatory sequence is selected from the group consisting of a transcription initiation region, a translation control region, transcription termination region, a promoter, a ribosome binding region, an intergenic region, and a regulatory region associated with an operon.

23. The mutant of claim 5, wherein the mutation is obtained by directed mutagenesis and comprises a deletion of the entire nucleotide sequence.

24. A mutant of a gram negative bacterium belonging to the family Pasteurellaceae, having a mutation in a nucleotide sequence, wherein the nucleotide sequence prior to mutation encodes a polypeptide essentially consisting of SEQ ID NO. 38, wherein the gram negative bacterium is: *Pasteurella multocida, Pasteurella multocida P*-1059, *Pasteurella multocida PM70, Pasteurella haemolytica, Pasteurella anatipestifer* or *Actinobacillus pleuropneumoniae*, and wherein the mutation attenuates virulence of the bacterium.

25. An immunogenic composition or vaccine comprising the mutant according to claim 24, and a pharmaceutically or veterinarily acceptable diluent, carrier, vehicle or excipient and optionally an adjuvant.

26. An immunogenic composition or vaccine comprising the mutant according to claim 22, and a pharmaceutically or veterinarily acceptable diluent, carrier, vehicle or excipient, wherein the composition or vaccine optionally comprises an adjuvant.

\* \* \* \* \*